(12) United States Patent
Henke et al.

(10) Patent No.: US 8,834,346 B2
(45) Date of Patent: Sep. 16, 2014

(54) STIMULUS SEQUENCER FOR A CLOSED LOOP NEUROMODULATOR

(75) Inventors: Reinhold Henke, Plymouth, MN (US); Evan S. Johnston, Blaine, MN (US); Peter Stasz, Mounds View, MN (US)

(73) Assignee: Dymedix Corporation, Shoreview, MN (US)

( * ) Notice: Subject to any disclaimer, the term of this patent is extended or adjusted under 35 U.S.C. 154(b) by 1185 days.

(21) Appl. No.: 12/583,582

(22) Filed: Aug. 21, 2009

(65) Prior Publication Data

US 2010/0063348 A1 Mar. 11, 2010

Related U.S. Application Data

(60) Provisional application No. 61/090,966, filed on Aug. 22, 2008, provisional application No. 61/090,968, filed on Aug. 22, 2008, provisional application No. 61/091,118, filed on Aug. 22, 2008, provisional application No. 61/091,112, filed on Aug. 22, 2008, provisional application No. 61/091,105, filed on Aug. 22, 2008, provisional application No. 61/091,101, filed on Aug. 22, 2008, provisional application No. 61/091,099, filed on Aug. 22, 2008, provisional application No. 61/091,094, filed on Aug. 22, 2008, provisional application No. 61/091,087, filed on Aug. 22, 2008, provisional application No. 61/091,082, filed on Aug. 22, 2008, provisional application No. 61/091,078, filed on Aug. 22, 2008, provisional application No. 61/091,074, filed on Aug. 22, 2008.

(51) Int. Cl.
*A61M 21/00* (2006.01)
*A61M 21/02* (2006.01)

(52) U.S. Cl.
CPC .................................. *A61M 21/02* (2013.01)
USPC ............................................ 600/27; 600/534

(58) Field of Classification Search
USPC .......... 600/529, 532–542; 128/848, 897, 898; 607/2, 3, 42, 59, 61, 62, 72, 73, 76
See application file for complete search history.

(56) References Cited

U.S. PATENT DOCUMENTS

| 3,478,344 A | 11/1969 | Schwitzgebel et al. |
| 3,483,861 A | 12/1969 | Tiep |

(Continued)

FOREIGN PATENT DOCUMENTS

| EP | 0014693 B1 | 6/1983 |
| EP | 1745742 A1 | 1/2007 |

(Continued)

OTHER PUBLICATIONS

U.S. Appl. No. 12/434,042, Non Final Office Action mailed May 31, 2011, 18 pgs.

(Continued)

*Primary Examiner* — Samuel Gilbert
*Assistant Examiner* — Carrie R Dorna
(74) *Attorney, Agent, or Firm* — Schwegman Lundberg & Woessner, P.A.

(57) ABSTRACT

This document discusses, among other things, a system and method for generating a sleep therapy stimulus waveform for a patient. Stimulus sequence information can be selected from a sequence memory array, and stimulus sequence information can be received from the sequence memory array at a stimulus generator selector. A generator select signal can be provided to a stimulus generator of a closed loop neuromodulator using the stimulus sequence information and a stimulus duration signal, wherein the generator select signal can include stimulus type information related to stimulus pulses generated using the closed loop neuromodulator.

16 Claims, 55 Drawing Sheets

(56) References Cited

U.S. PATENT DOCUMENTS

| | | |
|---|---|---|
| 3,530,494 A | 9/1970 | Baratta |
| 3,572,316 A | 3/1971 | Vogelman et al. |
| 3,593,703 A | 7/1971 | Gunn et al. |
| 3,696,377 A | 10/1972 | Wall |
| 3,782,368 A | 1/1974 | Reibold |
| 3,802,417 A | 4/1974 | Lang |
| 3,827,301 A | 8/1974 | Parker |
| 3,998,209 A | 12/1976 | Macvaugh |
| 4,072,145 A | 2/1978 | Silva |
| 4,169,462 A | 10/1979 | Strube |
| 4,185,621 A | 1/1980 | Morrow |
| 4,220,142 A | 9/1980 | Rosen et al. |
| 4,267,845 A | 5/1981 | Robertson, Jr. et al. |
| 4,304,227 A | 12/1981 | Samelson |
| 4,308,872 A | 1/1982 | Watson et al. |
| 4,373,534 A | 2/1983 | Watson |
| 4,378,808 A | 4/1983 | Lichtenstein |
| 4,440,160 A | 4/1984 | Fischell et al. |
| 4,443,730 A | 4/1984 | Kitamura et al. |
| 4,452,252 A | 6/1984 | Sackner |
| 4,456,015 A | 6/1984 | Sackner |
| 4,499,394 A | 2/1985 | Koal |
| 4,503,862 A | 3/1985 | Baessler |
| 4,509,527 A | 4/1985 | Fraden |
| 4,576,179 A | 3/1986 | Manus et al. |
| 4,577,510 A | 3/1986 | Bur et al. |
| 4,593,686 A | 6/1986 | Lloyd et al. |
| 4,600,855 A | 7/1986 | Strachan |
| 4,644,330 A | 2/1987 | Dowling |
| 4,666,198 A | 5/1987 | Heiserman |
| 4,669,477 A | 6/1987 | Ober |
| 4,700,203 A | 10/1987 | Yamamuro et al. |
| 4,715,367 A | 12/1987 | Crossley |
| 4,747,413 A | 5/1988 | Bloch |
| 4,748,672 A | 5/1988 | Nevill, Jr. et al. |
| 4,788,533 A | 11/1988 | Mequignon |
| 4,791,933 A | 12/1988 | Asai et al. |
| 4,813,427 A | 3/1989 | Schlaefke et al. |
| 4,814,661 A | 3/1989 | Ratzlaff et al. |
| 4,817,625 A | 4/1989 | Miles |
| 4,819,860 A | 4/1989 | Hargrove et al. |
| 4,823,802 A | 4/1989 | Romanovskaya |
| 4,827,943 A | 5/1989 | Bornn et al. |
| 4,830,008 A | 5/1989 | Meer |
| 4,834,109 A | 5/1989 | Watson |
| 4,836,219 A | 6/1989 | Hobson et al. |
| 4,895,160 A | 1/1990 | Reents |
| 4,909,260 A | 3/1990 | Salem et al. |
| 4,958,645 A | 9/1990 | Cadell et al. |
| 4,960,118 A | 10/1990 | Pennock |
| 4,971,065 A | 11/1990 | Pearce |
| 4,986,277 A | 1/1991 | Sackner |
| 4,989,612 A | 2/1991 | Fore |
| 5,038,785 A | 8/1991 | Blakeley et al. |
| 5,069,221 A | 12/1991 | Smith et al. |
| 5,088,501 A | 2/1992 | Niewisch |
| 5,099,702 A | 3/1992 | French |
| 5,113,566 A | 5/1992 | Weekamp et al. |
| 5,123,425 A | 6/1992 | Shannon, Jr. et al. |
| 5,161,541 A | 11/1992 | Bowman et al. |
| 5,178,156 A | 1/1993 | Takishima et al. |
| 5,201,322 A | 4/1993 | Henry et al. |
| 5,207,230 A | 5/1993 | Bowers |
| D338,413 S | 8/1993 | Ciambella |
| 5,277,193 A | 1/1994 | Takishima et al. |
| 5,295,490 A | 3/1994 | Dodakian |
| 5,311,875 A | 5/1994 | Stasz |
| 5,329,931 A | 7/1994 | Clauson et al. |
| 5,331,968 A | 7/1994 | Williams et al. |
| 5,335,657 A | 8/1994 | Terry, Jr. et al. |
| 5,348,008 A | 9/1994 | Bornn et al. |
| 5,365,937 A | 11/1994 | Reeves et al. |
| 5,413,111 A | 5/1995 | Wilkinson |
| 5,477,867 A | 12/1995 | Balkanyi |
| 5,515,738 A | 5/1996 | Tamori |
| 5,540,733 A | 7/1996 | Testerman et al. |
| 5,549,655 A | 8/1996 | Erickson |
| 5,555,891 A | 9/1996 | Eisenfeld |
| 5,558,099 A | 9/1996 | Bowman et al. |
| 5,684,460 A | 11/1997 | Scanlon |
| 5,748,103 A | 5/1998 | Flach et al. |
| 5,762,583 A | 6/1998 | Adams et al. |
| 5,765,563 A | 6/1998 | Schaaf |
| 5,767,791 A | 6/1998 | Stoop et al. |
| 5,797,849 A | 8/1998 | Vesely et al. |
| 5,825,119 A | 10/1998 | Shibata et al. |
| 5,825,293 A | 10/1998 | Ahmed et al. |
| 5,827,198 A | 10/1998 | Kassal |
| 5,832,592 A | 11/1998 | Bowman et al. |
| 5,853,005 A | 12/1998 | Scanlon |
| 5,895,360 A | 4/1999 | Christopherson et al. |
| D410,584 S | 6/1999 | Stasz et al. |
| 5,913,815 A | 6/1999 | Ball et al. |
| 5,913,829 A | 6/1999 | Reeves et al. |
| 5,924,979 A | 7/1999 | Swedlow et al. |
| 5,963,650 A | 10/1999 | Simionescu et al. |
| D417,161 S | 11/1999 | Stasz et al. |
| 5,996,418 A | 12/1999 | Rector et al. |
| 6,004,269 A | 12/1999 | Crowley et al. |
| 6,059,111 A | 5/2000 | Davila et al. |
| 6,070,098 A | 5/2000 | Moore-Ede et al. |
| 6,091,973 A | 7/2000 | Colla et al. |
| 6,093,158 A | 7/2000 | Morris |
| 6,142,950 A | 11/2000 | Allen et al. |
| 6,185,452 B1 | 2/2001 | Schulman et al. |
| 6,213,942 B1 | 4/2001 | Flach et al. |
| 6,213,955 B1 | 4/2001 | Karakasoglu et al. |
| 6,240,316 B1 | 5/2001 | Richmond et al. |
| 6,240,323 B1 | 5/2001 | Calenzo, Sr. et al. |
| 6,251,126 B1 | 6/2001 | Ottenhoff et al. |
| 6,254,545 B1 | 7/2001 | Stasz et al. |
| 6,269,269 B1 | 7/2001 | Ottenhoff et al. |
| 6,287,264 B1 | 9/2001 | Hoffman |
| 6,306,088 B1 | 10/2001 | Krausman et al. |
| 6,312,703 B1 | 11/2001 | Orthoefer |
| 6,341,230 B1 | 1/2002 | Koike et al. |
| 6,345,202 B2 | 2/2002 | Richmond et al. |
| 6,363,270 B1 | 3/2002 | Colla et al. |
| 6,364,834 B1 | 4/2002 | Reuss et al. |
| 6,368,287 B1 | 4/2002 | Hadas |
| 6,383,143 B1 | 5/2002 | Rost |
| 6,456,887 B1 | 9/2002 | Dudding et al. |
| 6,485,432 B1 | 11/2002 | Stasz et al. |
| 6,491,642 B1 | 12/2002 | Stasz |
| 6,496,705 B1 | 12/2002 | Ng et al. |
| 6,544,192 B2 | 4/2003 | Starr et al. |
| 6,544,199 B1 | 4/2003 | Morris |
| 6,551,256 B1 | 4/2003 | Stasz et al. |
| 6,561,987 B2 | 5/2003 | Pail |
| 6,702,755 B1 | 3/2004 | Stasz et al. |
| 6,734,802 B2 | 5/2004 | Halleck et al. |
| 6,762,687 B2 | 7/2004 | Perlman |
| 6,811,538 B2 | 11/2004 | Westbrook et al. |
| 6,840,907 B1 | 1/2005 | Brydon |
| 6,894,427 B2 | 5/2005 | Alfini |
| 6,935,335 B1 | 8/2005 | Lehrman et al. |
| 7,007,177 B2 | 2/2006 | Cannon et al. |
| 7,089,932 B2 | 8/2006 | Dodds |
| 7,115,097 B2 | 10/2006 | Johnson |
| 7,134,435 B2 | 11/2006 | Scott |
| 7,206,639 B2 | 4/2007 | Jacobsen et al. |
| 7,267,652 B2 | 9/2007 | Coyle et al. |
| 7,277,749 B2 | 10/2007 | Gordon et al. |
| 7,322,356 B2 | 1/2008 | Critzer et al. |
| 7,336,991 B2 | 2/2008 | Yanagihara et al. |
| 7,363,926 B2 | 4/2008 | Pflueger et al. |
| 7,367,935 B2 | 5/2008 | Mechlenburg et al. |
| 7,422,014 B1 | 9/2008 | Smith |
| 7,426,412 B1 | 9/2008 | Schecter |
| 7,427,270 B2 | 9/2008 | Izumi et al. |
| 7,524,279 B2 | 4/2009 | Auphan |
| 7,942,822 B1 | 5/2011 | Koh |
| 8,008,997 B2 | 8/2011 | Cho |
| 8,579,794 B2 | 11/2013 | Henke |

(56) References Cited

U.S. PATENT DOCUMENTS

| | | |
|---|---|---|
| 2001/0018547 A1 | 8/2001 | Mechlenburg et al. |
| 2002/0057202 A1 | 5/2002 | Luzon |
| 2002/0123692 A1 | 9/2002 | Pail |
| 2003/0100843 A1 | 5/2003 | Hoffman |
| 2003/0187356 A1 | 10/2003 | Wakabayashi et al. |
| 2003/0195588 A1 | 10/2003 | Fischell et al. |
| 2003/0204225 A1* | 10/2003 | Heathershaw et al. ......... 607/48 |
| 2003/0236467 A1 | 12/2003 | Alfini |
| 2004/0039419 A1 | 2/2004 | Stickney et al. |
| 2004/0113771 A1 | 6/2004 | Ozaki et al. |
| 2004/0151757 A1 | 8/2004 | Heirler |
| 2004/0182386 A1 | 9/2004 | Meier |
| 2004/0193003 A1 | 9/2004 | Mechlenburg et al. |
| 2005/0061315 A1 | 3/2005 | Lee et al. |
| 2005/0075669 A1 | 4/2005 | King |
| 2005/0113646 A1 | 5/2005 | Sotos et al. |
| 2005/0124864 A1 | 6/2005 | Mack et al. |
| 2005/0137464 A1 | 6/2005 | Bomba |
| 2005/0261559 A1 | 11/2005 | Mumford et al. |
| 2005/0283039 A1 | 12/2005 | Cornel |
| 2006/0000472 A1 | 1/2006 | Fenton |
| 2006/0034348 A1 | 2/2006 | Schaefer et al. |
| 2006/0069320 A1 | 3/2006 | Wolff et al. |
| 2006/0102171 A1 | 5/2006 | Gavish |
| 2006/0145878 A1 | 7/2006 | Lehrman et al. |
| 2006/0206014 A1 | 9/2006 | Ariav |
| 2006/0212273 A1 | 9/2006 | Krausman et al. |
| 2006/0212745 A1 | 9/2006 | Zansky et al. |
| 2006/0214507 A1 | 9/2006 | Suzuki |
| 2006/0241708 A1 | 10/2006 | Boute |
| 2006/0282001 A1 | 12/2006 | Noel et al. |
| 2006/0283446 A1 | 12/2006 | Chua et al. |
| 2007/0012089 A1 | 1/2007 | Stasz |
| 2007/0016089 A1 | 1/2007 | Fischell et al. |
| 2007/0023044 A1 | 2/2007 | Kwok et al. |
| 2007/0049842 A1 | 3/2007 | Hill et al. |
| 2007/0123758 A1 | 5/2007 | Miesel et al. |
| 2007/0129644 A1 | 6/2007 | Richards et al. |
| 2007/0131231 A1 | 6/2007 | Sharp |
| 2007/0154022 A1 | 7/2007 | Iketani et al. |
| 2007/0161903 A1 | 7/2007 | Yamashita et al. |
| 2007/0172029 A1 | 7/2007 | Felmlee et al. |
| 2007/0249952 A1 | 10/2007 | Rubin et al. |
| 2007/0255161 A1 | 11/2007 | De Backer |
| 2007/0282212 A1 | 12/2007 | Sierra et al. |
| 2007/0282215 A1 | 12/2007 | Ni et al. |
| 2008/0004904 A1 | 1/2008 | Tran |
| 2008/0009915 A1 | 1/2008 | Moses et al. |
| 2008/0021506 A1 | 1/2008 | Grocela |
| 2008/0035158 A1 | 2/2008 | Pflueger et al. |
| 2008/0048882 A1 | 2/2008 | Paugh et al. |
| 2008/0066753 A1 | 3/2008 | Martin et al. |
| 2008/0082018 A1 | 4/2008 | Sackner et al. |
| 2008/0092898 A1 | 4/2008 | Schneider et al. |
| 2008/0103407 A1 | 5/2008 | Bolea et al. |
| 2008/0103545 A1 | 5/2008 | Bolea et al. |
| 2008/0221468 A1 | 9/2008 | Stahmann et al. |
| 2008/0234780 A1 | 9/2008 | Smith et al. |
| 2008/0236597 A1 | 10/2008 | Bergersen |
| 2008/0243014 A1 | 10/2008 | Moussavi et al. |
| 2008/0243017 A1 | 10/2008 | Moussavi et al. |
| 2008/0243023 A1 | 10/2008 | Valkhof et al. |
| 2008/0275356 A1 | 11/2008 | Stasz et al. |
| 2009/0050154 A1 | 2/2009 | Strothmann et al. |
| 2009/0076405 A1 | 3/2009 | Amurthur et al. |
| 2009/0105125 A1 | 4/2009 | Zhao et al. |
| 2009/0158425 A1 | 6/2009 | Chan et al. |
| 2009/0287265 A1 | 11/2009 | Henke |
| 2009/0306528 A1 | 12/2009 | Curti et al. |
| 2010/0048985 A1 | 2/2010 | Henke et al. |
| 2010/0048986 A1 | 2/2010 | Henke et al. |
| 2010/0049264 A1 | 2/2010 | Henke et al. |
| 2010/0049265 A1 | 2/2010 | Henke et al. |
| 2010/0056852 A1 | 3/2010 | Henke et al. |
| 2010/0056853 A1 | 3/2010 | Henke et al. |
| 2010/0056855 A1 | 3/2010 | Henke et al. |
| 2010/0056941 A1 | 3/2010 | Henke et al. |
| 2010/0057148 A1 | 3/2010 | Henke et al. |
| 2010/0063348 A1 | 3/2010 | Henke et al. |
| 2010/0063350 A1 | 3/2010 | Henke et al. |
| 2010/0069769 A1 | 3/2010 | Henke et al. |
| 2010/0069771 A1 | 3/2010 | Henke et al. |
| 2010/0069772 A1 | 3/2010 | Henke et al. |
| 2010/0069773 A1 | 3/2010 | Henke et al. |
| 2010/0076251 A1 | 3/2010 | Stasz et al. |
| 2010/0076252 A1 | 3/2010 | Henke et al. |

FOREIGN PATENT DOCUMENTS

| | | |
|---|---|---|
| JP | 5112220 A | 1/1976 |
| JP | 59140796 A | 8/1984 |
| JP | 60100961 A | 6/1985 |
| JP | 60127091 A | 7/1985 |
| JP | 60127092 A | 7/1985 |
| JP | 01107294 A | 4/1989 |
| JP | 02218997 A | 8/1990 |
| JP | 2000504913 A | 4/2000 |
| JP | 2001326985 A | 11/2001 |
| JP | 2005175985 A | 6/2005 |
| JP | 2005328125 A | 11/2005 |
| JP | 2006211317 A | 8/2006 |
| JP | 2007007433 A | 1/2007 |
| WO | WO-9705824 A1 | 2/1997 |
| WO | WO-9934864 A1 | 7/1999 |
| WO | WO-01043804 A1 | 6/2001 |
| WO | WO-03022149 A2 | 3/2003 |
| WO | WO-03082108 A1 | 10/2003 |
| WO | WO-2004112606 A1 | 12/2004 |
| WO | WO-2006066337 A1 | 6/2006 |
| WO | WO-2006116469 A3 | 11/2006 |
| WO | WO-2006138069 A1 | 12/2006 |
| WO | WO-2007008706 A3 | 1/2007 |
| WO | WO-2007013054 A1 | 2/2007 |
| WO | WO-2007071180 A1 | 6/2007 |
| WO | WO-2007100958 A1 | 9/2007 |
| WO | WO-2008037820 A1 | 4/2008 |
| WO | WO-2009134434 A1 | 11/2009 |
| WO | WO-2009158425 A1 | 12/2009 |
| WO | WO-2010021730 A1 | 2/2010 |
| WO | WO-2010025137 A1 | 3/2010 |
| WO | WO-2010030909 A1 | 3/2010 |
| WO | WO-2010033819 A1 | 3/2010 |
| WO | WO-2010033849 A1 | 3/2010 |

OTHER PUBLICATIONS

U.S. Appl. No. 12/434,042, Response filed Oct. 31, 2011 to Non Final Office Action mailed May 31, 2011, 11 pgs.

U.S. Appl. No. 12/491,068, Notice of Allowance mailed Nov. 28, 2011, 17 pgs.

U.S. Appl. No. 12/547,167, Non Final Office Action mailed Nov. 7, 2011, 5 pgs.

U.S. Appl. No. 12/547,167, Notice of Allowance mailed Dec. 28, 2011, 5 pgs.

U.S. Appl. No. 12/547,167, Response filed Nov. 8, 2011 to Non Final Office Action mailed Nov. 7, 2011, 11 pgs.

U.S. Appl. No. 12/557,765, Restriction Requirement mailed Dec. 23, 2011, 5 pgs.

U.S. Appl. No. 12/557,777, Non Final Office Action mailed Feb. 2, 2012, 19 pgs.

U.S. Appl. No. 12/557,790, Non Final Office Action mailed Dec. 22, 2011, 11 pgs.

U.S. Appl. No. 12/558,104, Non Final Office Action Mailed Feb. 3, 2012, 17 pgs.

U.S. Appl. No. 12/583,589, Restriction Requirements mailed Feb. 6, 2012, 8 pgs.

European Application Serial No. 09739237.7, Amended Claims Response filed Mar. 31, 2011, 12 pgs.

European Application Serial No. 09739237.7, Examination Notification Art. 94(3) mailed Jun. 20, 2011, 5 pgs.

International Application Serial No. PCT/US2009/002230, International Search Report mailed Jul. 3, 2009, 6 pgs.

(56) References Cited

OTHER PUBLICATIONS

International Application Serial No. PCT/US2009/002230, Written Opinion mailed Jul. 3, 2009, 6 pgs.
International Application Serial No. PCT/US2009/002408, Search Report mailed Aug. 13, 2009, 7 pgs.
International Application Serial No. PCT/US2009/002408, Written Opinion mailed Aug. 13, 2009, 6 pgs.
International Application Serial No. PCT/US2009/002705, Search Report mailed Oct. 1, 2009, 7 pgs.
International Application Serial No. PCT/US2009/002705, Written Opinion mailed Oct. 1, 2009, 5 pgs.
International Application Serial No. PCT/US2009/004766, International Report on Patentability mailed Mar. 3, 2011, 8 pgs.
International Application Serial No. PCT/US2009/004766, Search Report mailed Jan. 26, 2010, 7 pgs.
International Application Serial No. PCT/US2009/004766, Written Opinion mailed Jan. 26, 2010, 6 pgs.
International Application Serial No. PCT/US2009/056697, International Preliminary Report on Patentability mailed Mar. 24, 2011, 7 pgs.
International Application Serial No. PCT/US2009/056697, Search Report mailed Nov. 25, 2009, 4 pgs.
International Application Serial No. PCT/US2009/056697, Written Opinion mailed Nov. 25, 2009, 5 pgs.
International Application Serial No. PCT/US2009/057499, Search Report mailed Feb. 8, 2009, 8 pgs.
International Application Serial No. PCT/US2009/057499, Written Opinion mailed Feb. 8, 2010, 9 pgs.
International Application Serial No. PCT/US2009/057546, International Preliminary Report on Patentability mailed Mar. 31, 2011, 9 pgs.
International Application Serial No. PCT/US2009/057546, Search Report mailed Dec. 30, 2009, 8 pgs.
International Application Serial No. PCT/US2009/057546, Written Opinion mailed Dec. 30, 2009, 8 pgs.
"Piezo Film Sensors Technical Manual passage", Piezo Film Sensors Technical Manual, Measurement Specialties inc. No. 1005663-1 Rev. B, XP007906698 p. 11, line 1-line 31, (Apr. 2, 1999), 89 pgs.
Jovanov, E., et al., "Patient monitoring using personal area networks of wireless intelligent sensors", Bio-medical Sciences Instrumentation; vol. 37, XP002554091 ISSN: 0067-8856, (2001), 6 pgs.
Jovanov, E., et al., "Thermistor-based breathing sensor for circadian rhythm evaluation", Bio-medical Sciences Instrumentation; vol. 37, XP002554092 ISSN: 0067-8856, (2001), 5 pgs.
U.S. Appl. No. 12/434,042, Notice of Allowance mailed Jul. 9, 2013, 8 pgs.
U.S. Appl. No. 12/558,104, Non Final Office Action mailed Oct. 24, 2013, 11 pgs.
U.S. Appl. No. 12/558,104, Response filed Sep. 16, 2013 to Final Office Action mailed Mar. 14, 2013, 6 pgs.
U.S. Appl. No. 12/583,580, Non Final Office Action mailed Oct. 2, 2013, 24 pgs.
U.S. Appl. No. 12/583,581, Non Final Office Action mailed Sep. 25, 2013, 11 pgs.
U.S. Appl. No. 12/583,585, Non Final Office Action mailed Oct. 4, 2013, 14 pgs.
U.S. Appl. No. 12/583,585, Response filed Apr. 4, 2014 to Non Final Office Action mailed Oct. 4, 2013, 9 pgs.
U.S. Appl. No. 12/583,592, Non Final Office Action mailed Sep. 27, 2013, 11 pgs.
European Application Serial No. 09789182.4, Response filed Sep. 3, 2013 to Examination Notification Art. 94(3) mailed Feb. 22, 2013, 24 pgs.
Japanese Application Serial No. 2011-507465, Office Action mailed Sep. 17, 2013, 6 pgs.
U.S. Appl. No. 12/434,042, Advisory Action mailed May 17, 2012, 3 pgs.
U.S. Appl. No. 12/434,042, Final Office Action mailed Feb. 28, 2012, 19 pgs.
U.S. Appl. No. 12/434,042, Final Office Action mailed Apr. 18, 2013, 14 pgs.
U.S. Appl. No. 12/434,042, Non Final Office Action mailed Jun. 22, 2012, 12 pgs.
U.S. Appl. No. 12/434,042, Response filed Apr. 30, 2012 to Final Office Action mailed Feb. 28, 2012, 10 pgs.
U.S. Appl. No. 12/434,042, Response filed Jun. 19, 2013 to Final Office Action mailed Apr. 18, 2013, 6 pgs.
U.S. Appl. No. 12/434,042, Response filed Dec. 20, 2012 to Non Final Office Action mailed Jun. 22, 2012, 10 pgs.
U.S. Appl. No. 12/557,765, Final Office Action mailed Aug. 2, 2012, 17 pgs.
U.S. Appl. No. 12/557,765, Non Final Office Action mailed Mar. 9, 2012, 16 pgs.
U.S. Appl. No. 12/557,765, Response filed Feb. 23, 2012 to Restriction Requirement mailed Dec. 23, 2011, 8 pgs.
U.S. Appl. No. 12/557,765, Response filed Jul. 9, 2012 to Non Final Office Action mailed Mar. 9, 2012, 14 pgs.
U.S. Appl. No. 12/557,777, Final Office Action mailed Aug. 8, 2012, 21 pgs.
U.S. Appl. No. 12/557,777, Response filed Jul. 2, 2012 to Non Final Office Action mailed Feb. 2, 2012, 13 pgs.
U.S. Appl. No. 12/557,790, Final Office Action mailed Jun. 7, 2012, 12 pgs.
U.S. Appl. No. 12/557,790, Response filed May 22, 2012 to Non Final Office Action mailed Dec. 22, 2011, 8 pgs.
U.S. Appl. No. 12/558,104, Final Office Action mailed Mar. 14, 2013, 16 pgs.
U.S. Appl. No. 12/558,104, Response filed Jul. 31, 2012 to Non Final Office Action mailed Feb. 3, 2012, 12 pgs.
U.S. Appl. No. 12/562,669, Non Final Office Action mailed Aug. 28, 2012, 8 pgs.
U.S. Appl. No. 12/562,669, Response filed Jul. 9, 2012 to Restriction Requirement mailed Jun. 7, 2012, 6 pgs.
U.S. Appl. No. 12/562,669, Restriction Requirement mailed Jun. 7, 2012, 5 pgs.
U.S. Appl. No. 12/562,959, Non Final Office Action mailed Aug. 23, 2012, 8 pgs.
U.S. Appl. No. 12/562,959, Response filed May 21, 2012 to Restriction Requirement mailed Apr. 19, 2012, 6 pgs.
U.S. Appl. No. 12/562,959, Restriction Requirement mailed Apr. 19, 2012, 5 pgs.
U.S. Appl. No. 12/583,580, Response filed Jun. 17, 2013 to Restriction Requirement mailed Dec. 17, 2012, 11 pgs.
U.S. Appl. No. 12/583,580, Restriction Requirement mailed Dec. 17, 2012, 7 pgs.
U.S. Appl. No. 12/583,581, Response filed Jun. 19, 2013 to Restriction Requirement mailed Jan. 24, 2013, 7 pgs.
U.S. Appl. No. 12/583,581, Restriction Requirement mailed Jan. 24, 2013, 6 pgs.
U.S. Appl. No. 12/583,585, Response filed Jun. 19, 2013 to Restriction Requirement mailed Mar. 22, 2013, 8 pgs.
U.S. Appl. No. 12/583,585, Restriction Requirement mailed Mar. 22, 2013, 6 pgs.
U.S. Appl. No. 12/583,586, Restriction Requirement mailed Jan. 24, 2013, 6 pgs.
U.S. Appl. No. 12/583,587, Restriction Requirement mailed Feb. 27, 2013, 6 pgs.
U.S. Appl. No. 12/583,588, Non Final Office Action mailed Jun. 29, 2012, 9 pgs.
U.S. Appl. No. 12/583,589, Non Final Office Action mailed Jun. 7, 2012, 10 pgs.
U.S. Appl. No. 12/583,589, Response filed Apr. 5, 2012 to Restriction Requirement mailed Feb. 6, 2012, 7 pgs.
U.S. Appl. No. 12/583,590, Restriction Requirement mailed Jan. 24, 2013, 6 pgs.
U.S. Appl. No. 12/583,591, Final Office Action mailed Dec. 14, 2012, 11 pgs.
U.S. Appl. No. 12/583,591, Non Final Office Action mailed Mar. 30, 2012, 11 pgs.
U.S. Appl. No. 12/583,591, Response filed Aug. 30, 2012 to Non Final Office Action mailed Mar. 30, 2012, 14 pgs.

(56) References Cited

OTHER PUBLICATIONS

U.S. Appl. No. 12/583,592, Restriction Requirement mailed Feb. 26, 2013, 6 pgs.
U.S. Appl. No. 12/583,592, Restriction Requirement mailed Jun. 25, 2013, 8 pgs.
U.S. Appl. No. 12/583,593, Restriction Requirement mailed Feb. 26, 2013, 6 pgs.
European Application Serial No. 09739237.7, Response filed Apr. 18, 2012 to Office Action mailed Jun. 20, 2011, 4 pgs.
European Application Serial No. 09789182.4, Examination Notification Art. 94(3) mailed Feb. 22, 2013, 7 pgs.
International Application Serial No. PCT/US2009/002705, International Preliminary Report on Patentability mailed, 7 pgs, Mailed Nov. 11, 2010.
International Application Serial No. PCT/US2009/048491, International Preliminary Report on Patentability mailed Jan. 5, 2011, 8 pgs.
International Application Serial No. PCT/US2009/048491, International Search Report and Written Opinion mailed Sep. 28, 2009, 11 pgs.
International Application Serial No. PCT/US2009/048496, International Preliminary Report on Patentability mailed Jan. 5, 2011, 6 pgs.
International Application Serial No. PCT/US2009/048496, International Search Report and Written Opinion mailed Sep. 7, 2009, 7 pgs.
International Application Serial No. PCT/US2009/054892, International Preliminary Report on Patentability mailed Mar. 1, 2011, 7 pgs.
International Application Serial No. PCT/US2009/054892, International Search Report and Written Opinion mailed Dec. 15, 2009, 8 pgs.
International Application Serial No. PCT/US2009/057499, International Preliminary Report on Patentability mailed Mar. 31, 2011, 10 pgs.

* cited by examiner

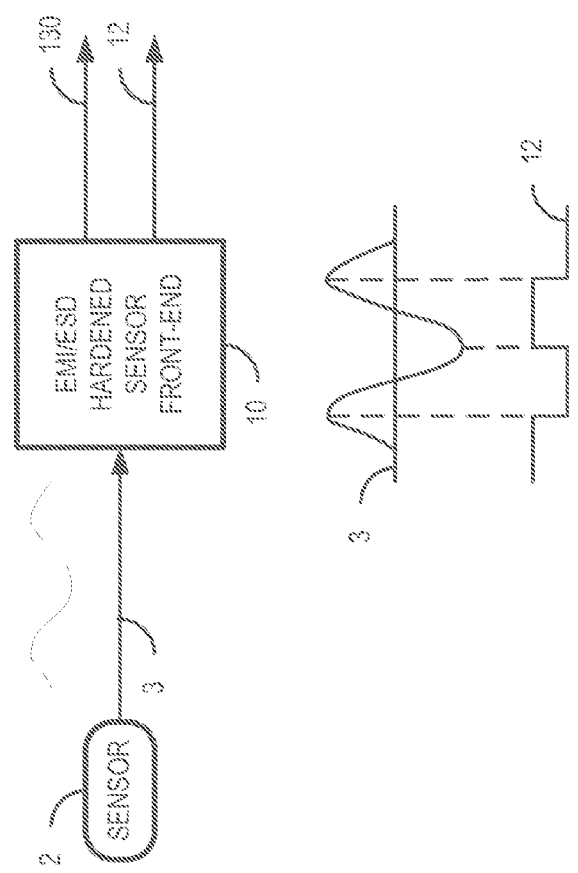

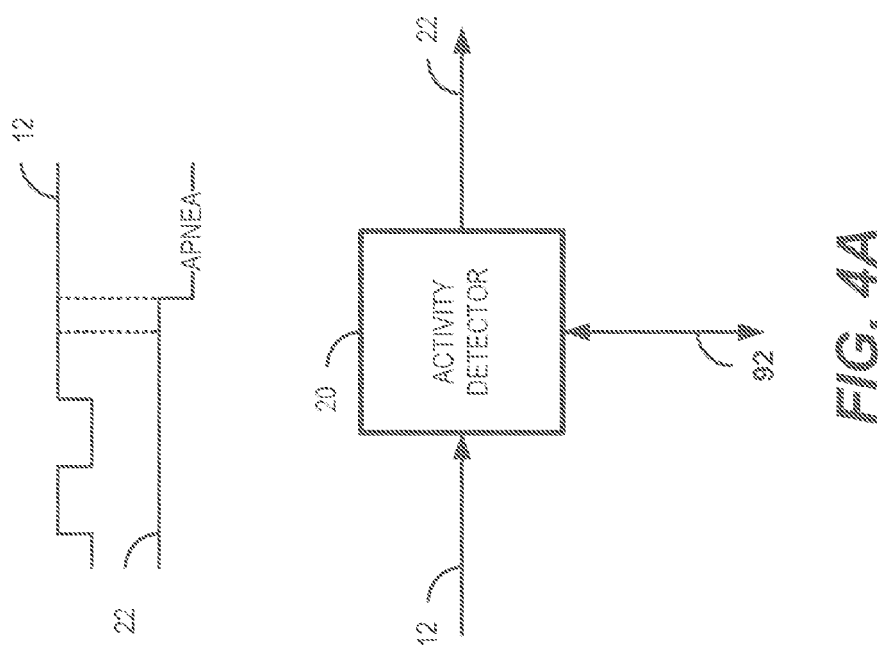

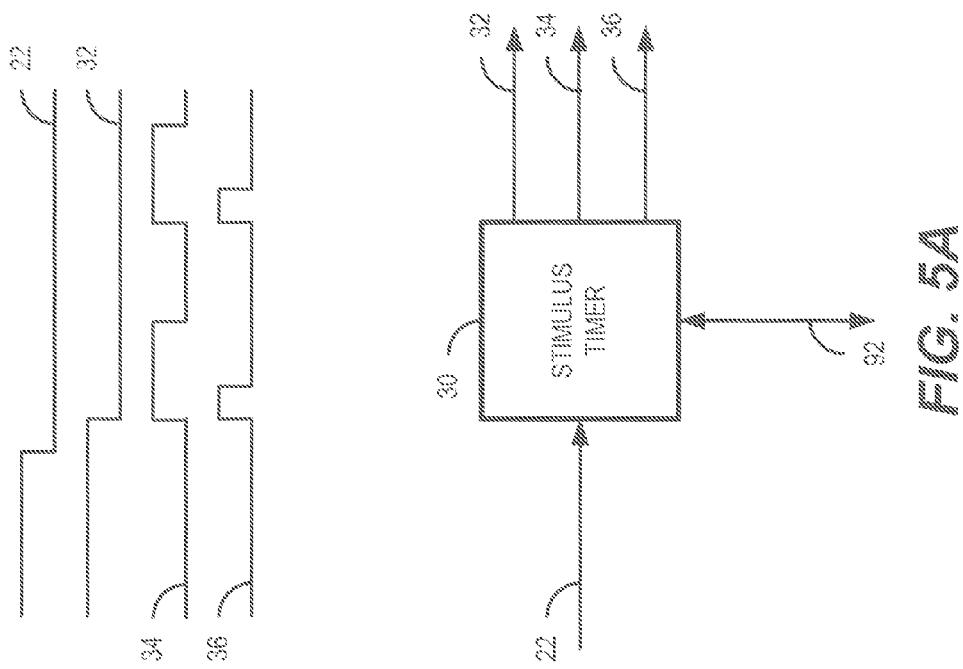

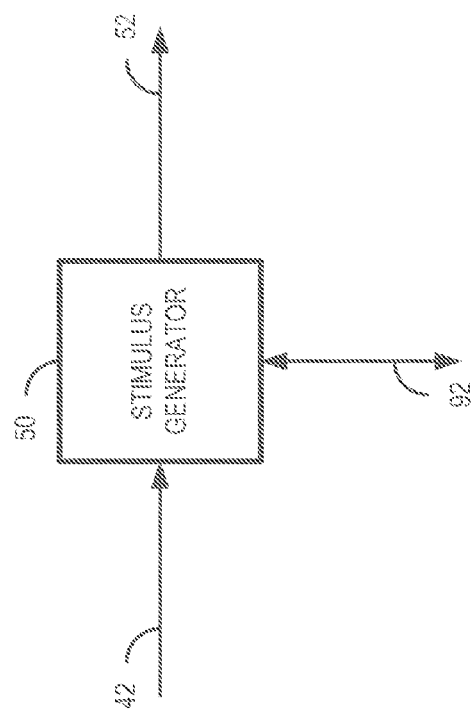

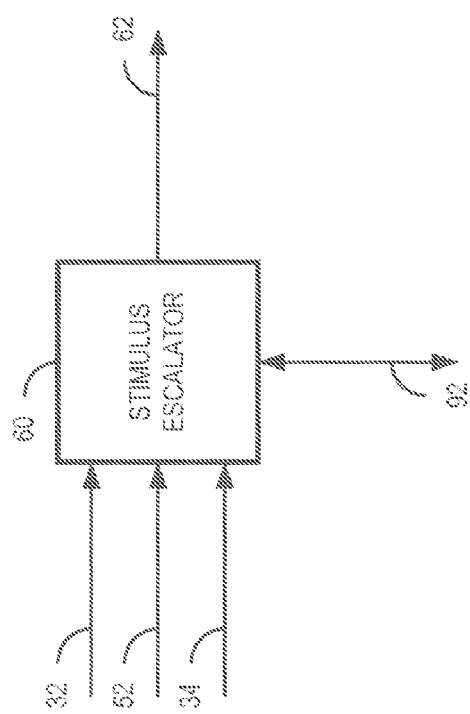

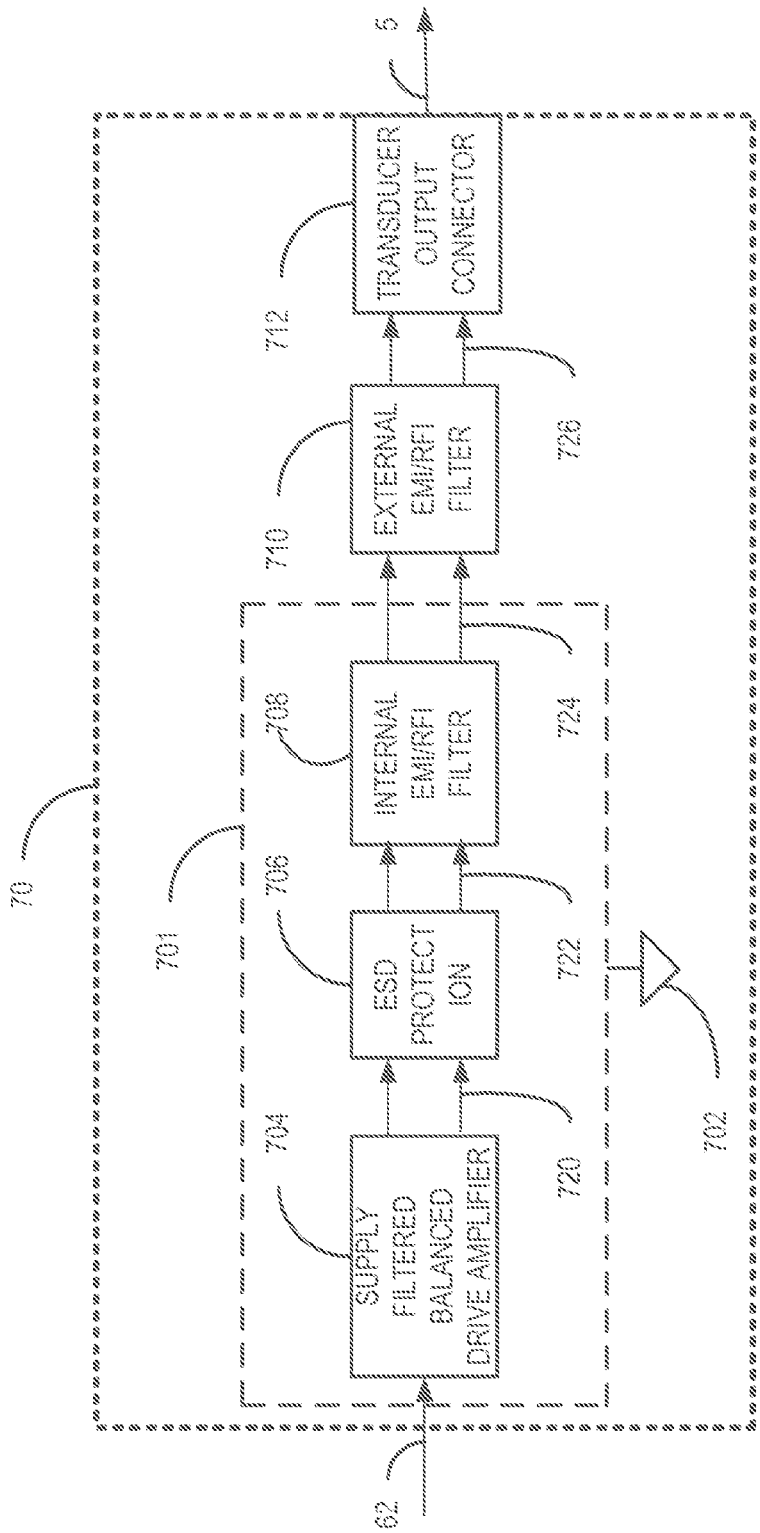

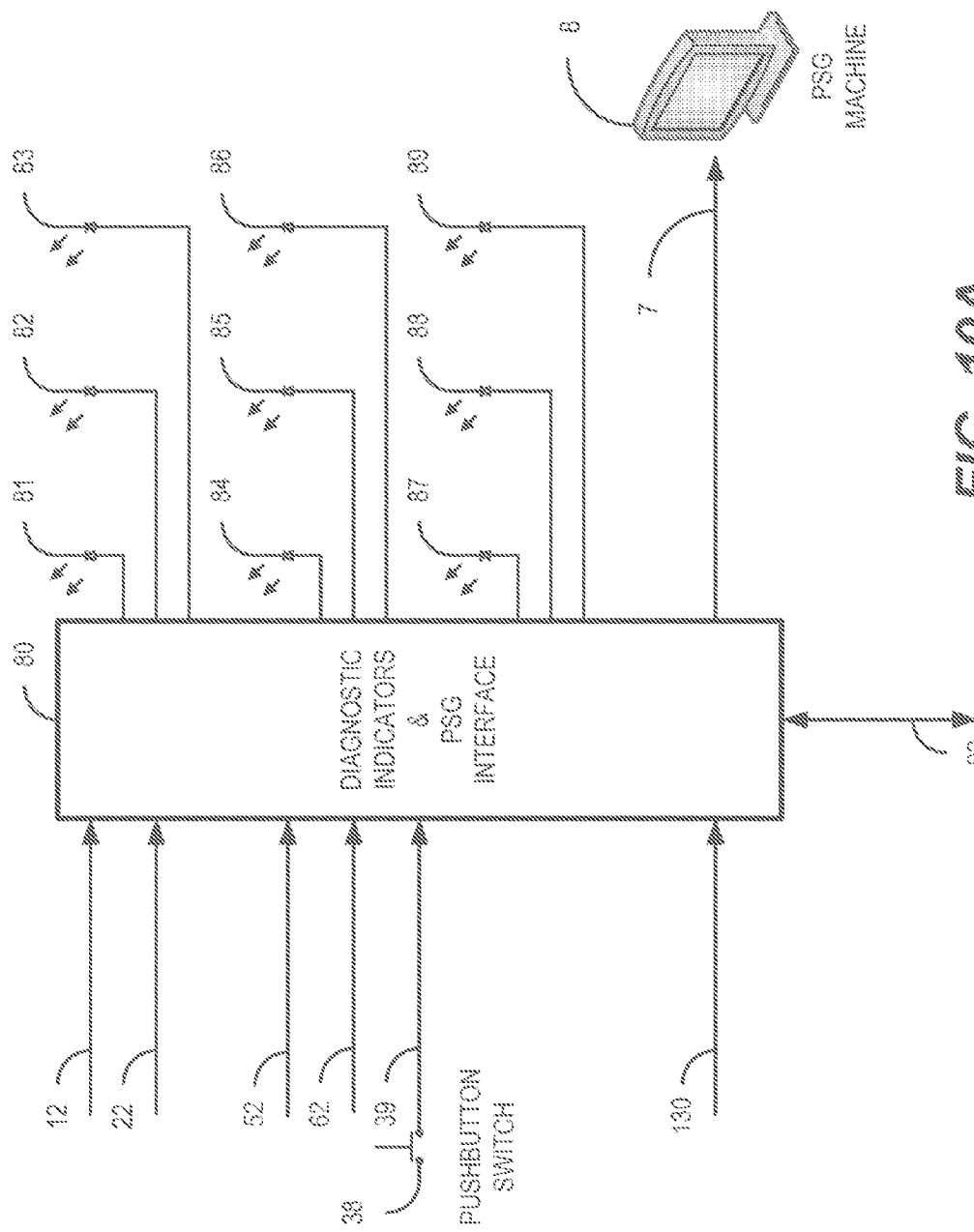

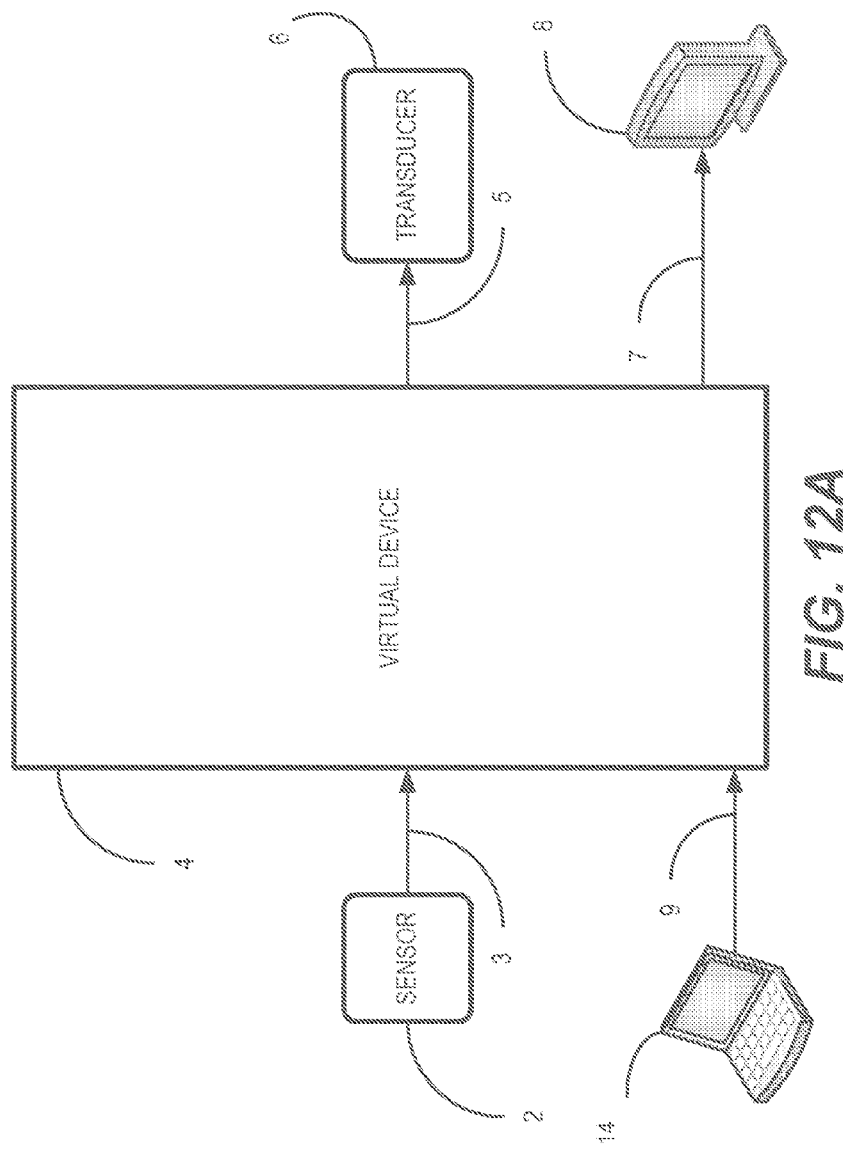

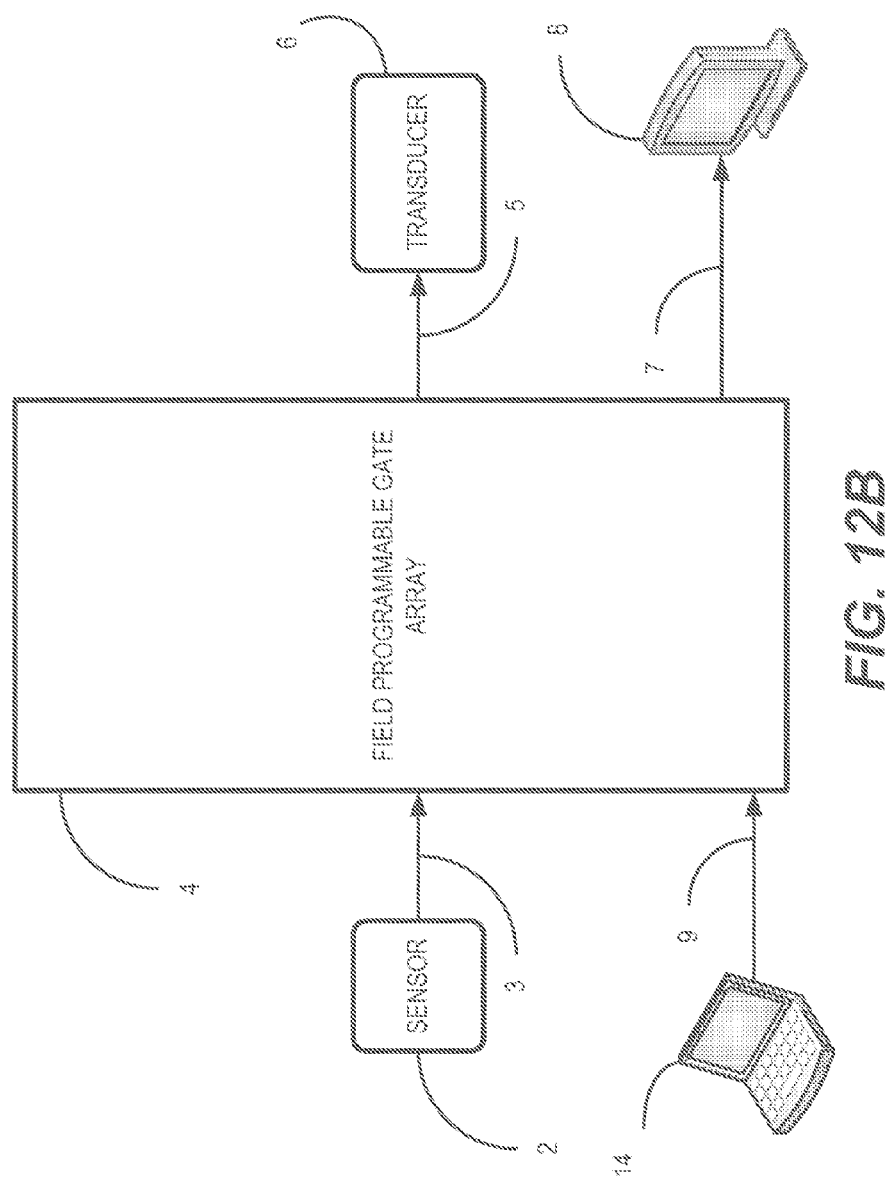

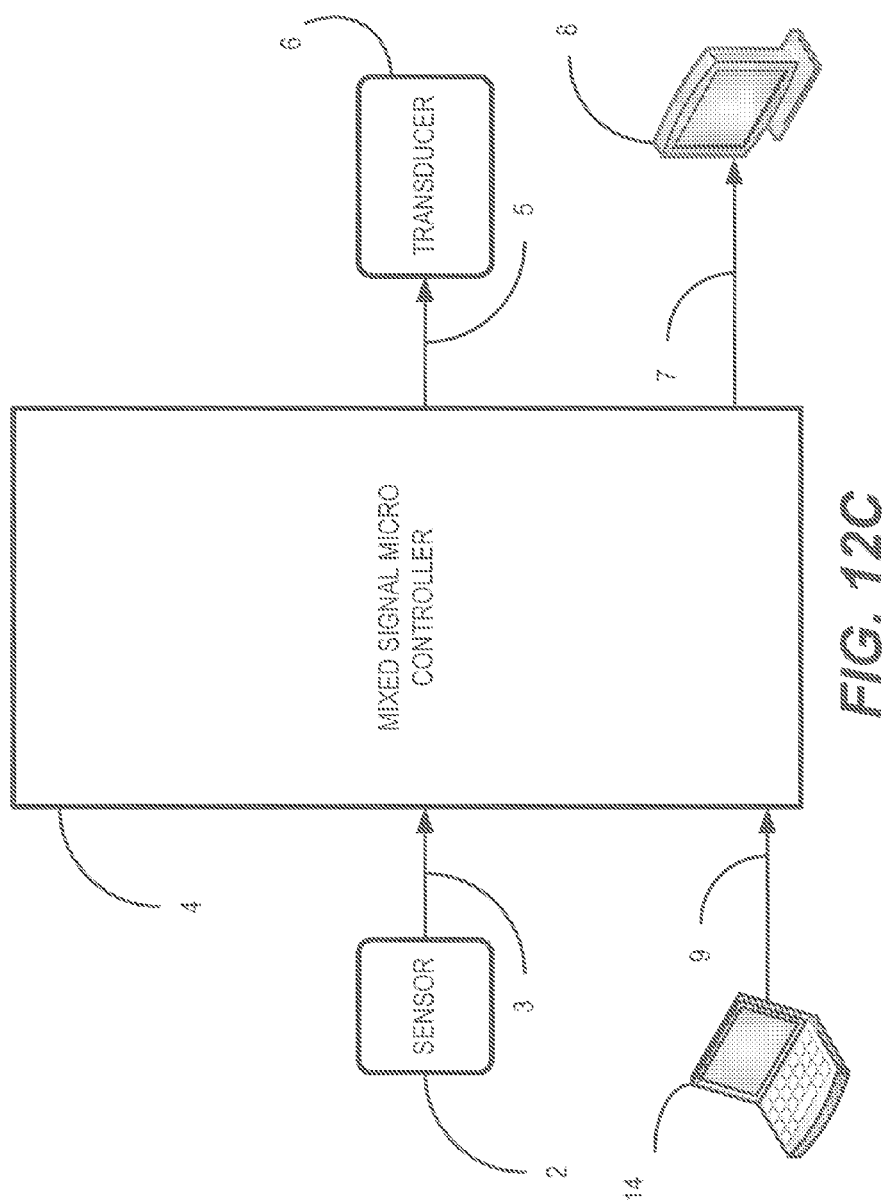

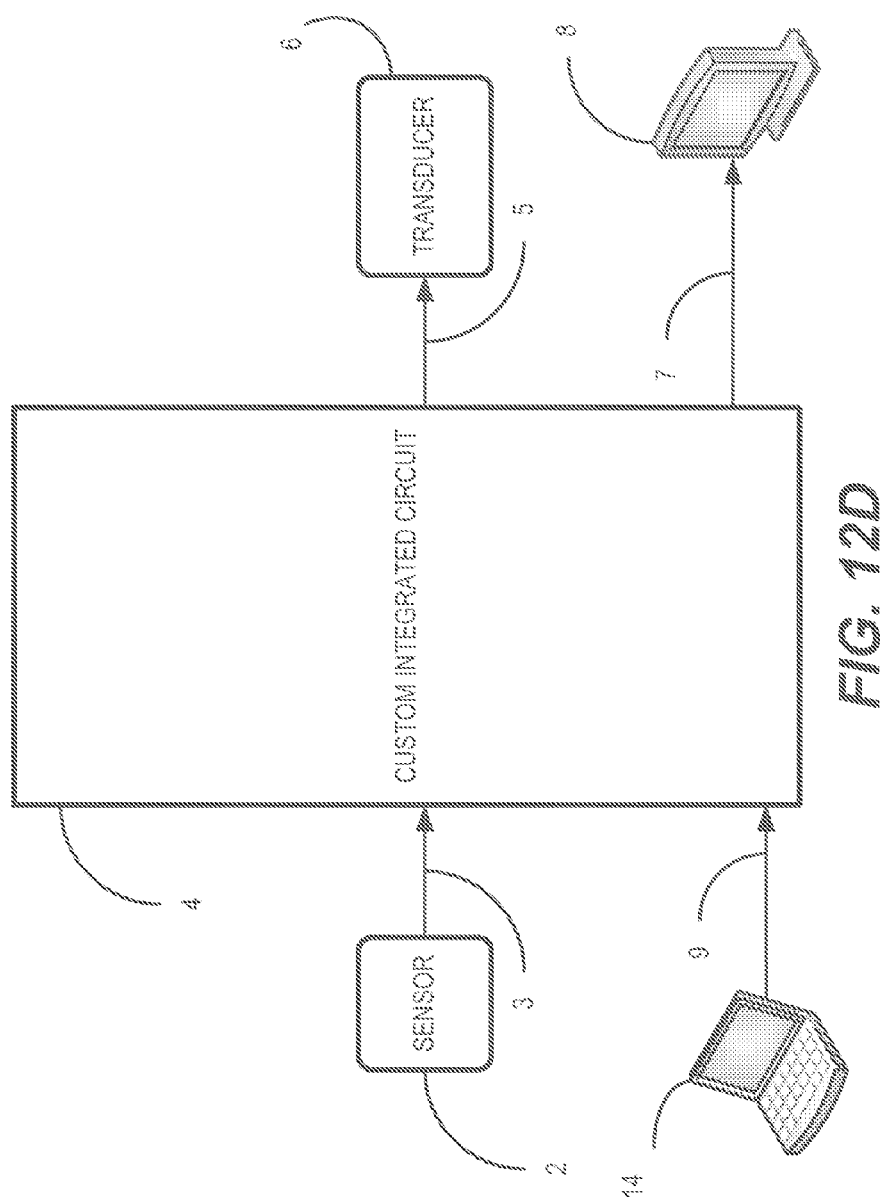

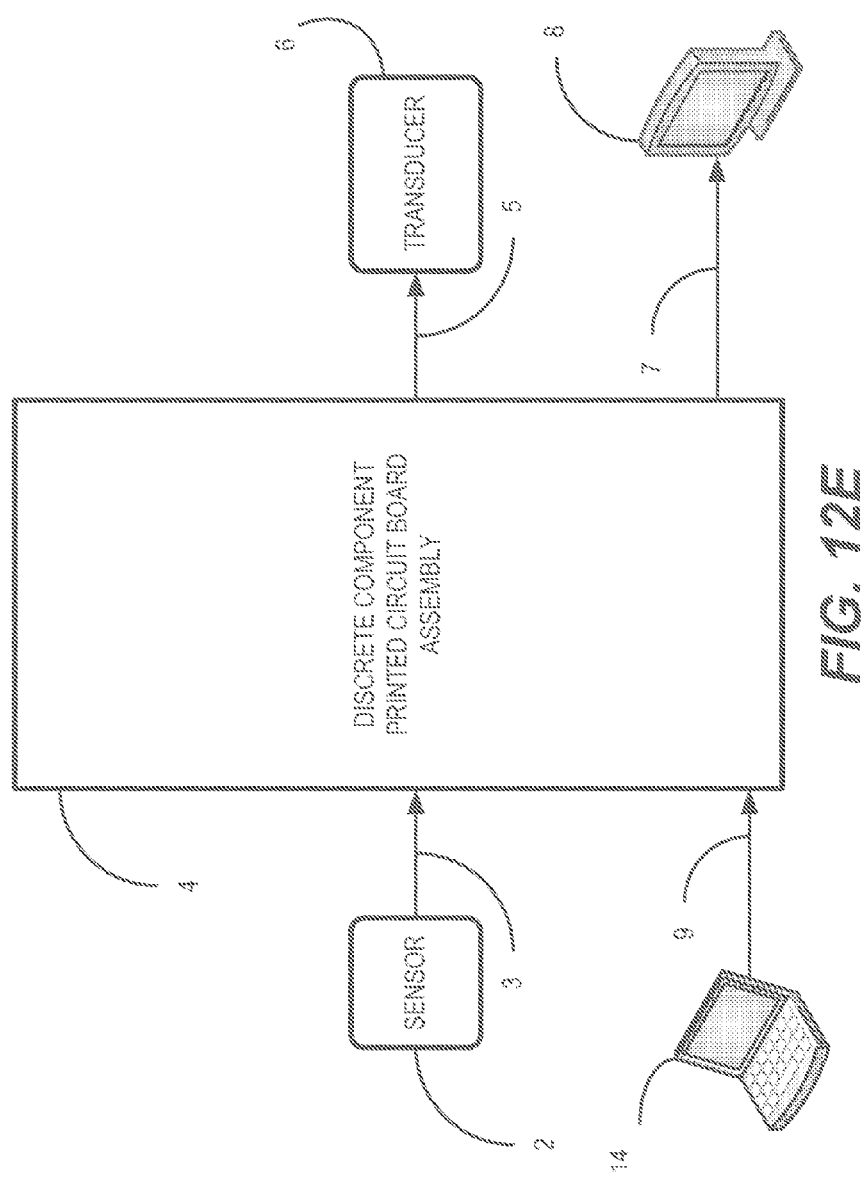

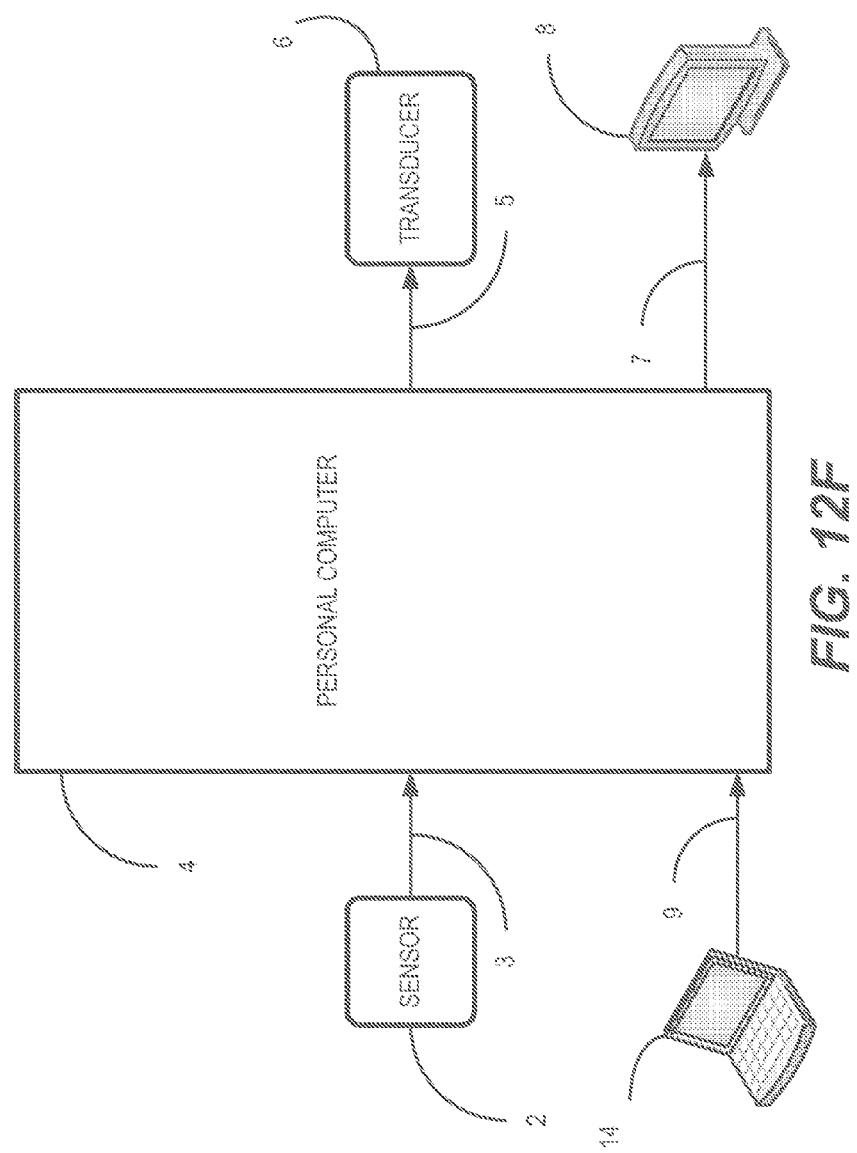

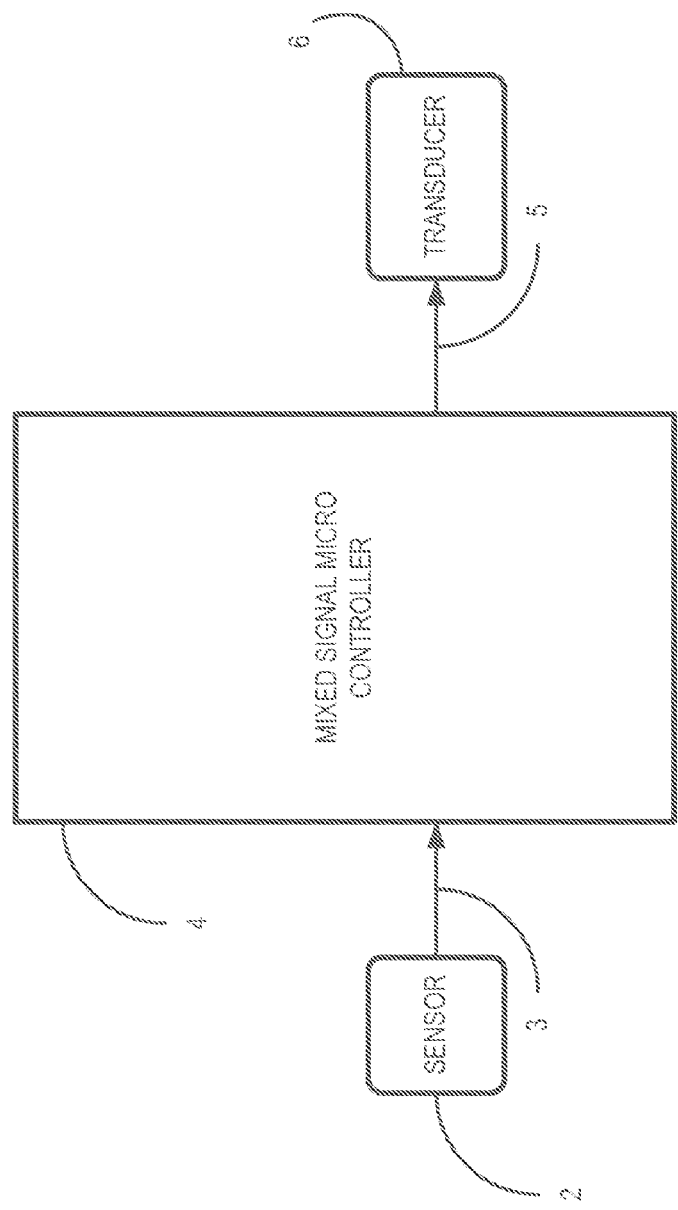

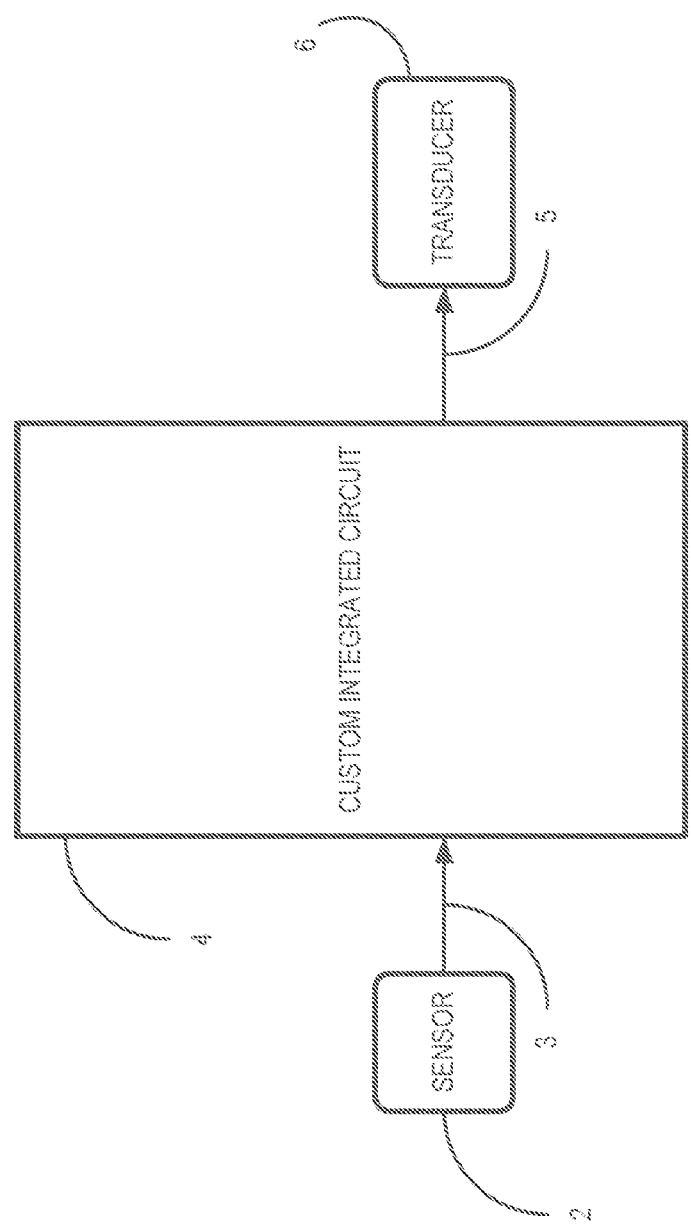

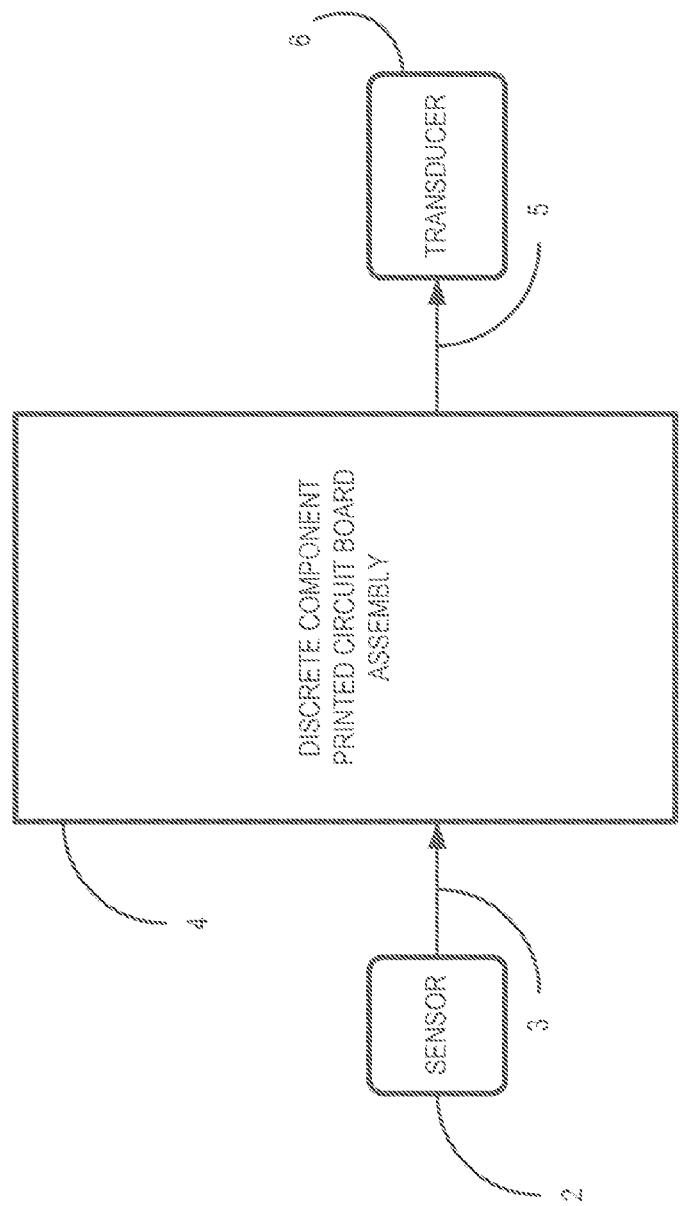

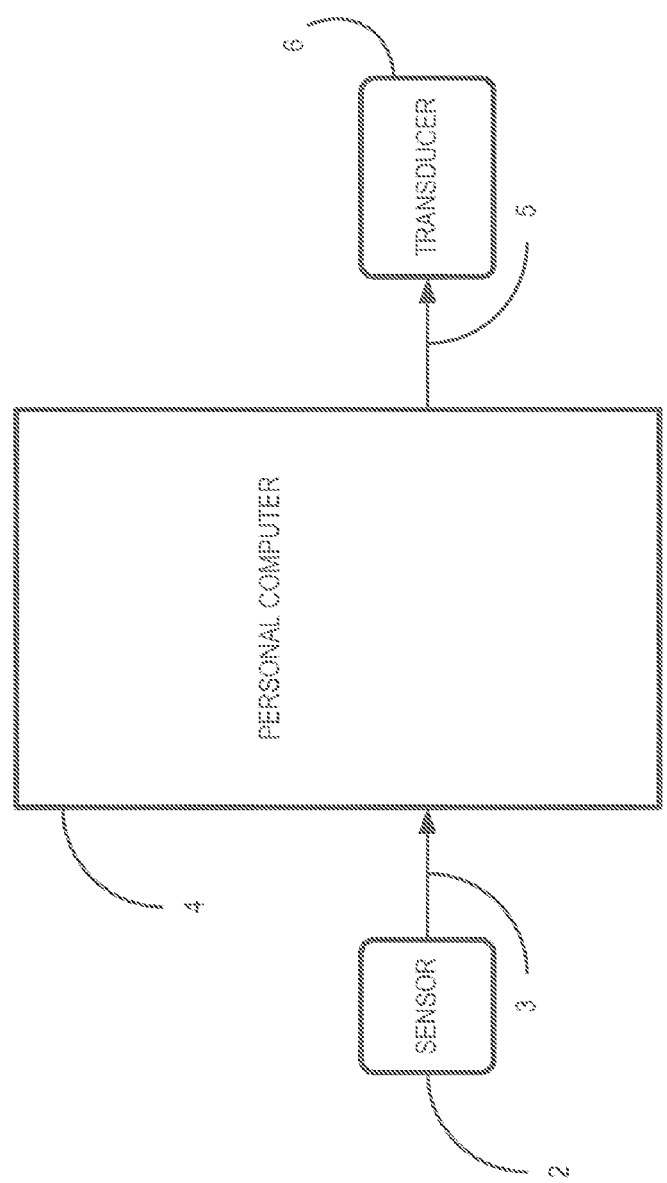

STIMULUS SEQUENCER FOR A CLOSED LOOP NEUROMODULATOR

PRIORITY AND RELATED APPLICATIONS

This application claims the benefit under 35 U.S.C 119(e) of the following United States Provisional Patent Applications, the contents of which are incorporated herein by reference in their entirety: U.S. Provisional Patent Application Ser. No. 61/090,966 filed Aug. 22, 2008, U.S. Provisional Patent Application Ser. No. 61/090,968 filed Aug. 22, 2008, U.S. Provisional Patent Application Ser. No. 61/091,118 filed Aug. 22, 2008, U.S. Provisional Patent Application Ser. No. 61/091,112 filed Aug. 22, 2008, U.S. Provisional Patent Application Ser. No. 61/091,105 filed Aug. 22, 2008, U.S. Provisional Patent Application Ser. No. 61/091,101 filed Aug. 22, 2008, U.S. Provisional Patent Application Ser. No. 61/091,099 filed Aug. 22, 2008, U.S. Provisional Patent Application Ser. No. 61/091,094 filed Aug. 22, 2008, U.S. Provisional Patent Application Ser. No. 61/091,087 filed Aug. 22, 2008, U.S. Provisional Patent Application Ser. No. 61/091,082 filed Aug. 22, 2008, U.S. Provisional Patent Application Ser. No. 61/091,078 filed Aug. 22, 2008, and U.S. Provisional Patent Application Ser. No. 61/091,074 filed Aug. 22, 2008.

TECHNICAL FIELD

The present subject matter relates generally to sleep therapy and more specifically to a stimulus sequencer for a closed loop neuromodulator.

BACKGROUND

Sleep disorders have recently become the focus of a growing number of physicians. Sleep disorders include obstructive sleep apnea, central sleep apnea, complex sleep apnea, snoring, restless leg syndrome (RLS), periodic limb movement (PLM), sudden infant death syndrome (SIDS), and related neurological and physiological events or conditions occurring during sleep. Many hospitals and clinics have established sleep laboratories (sleep labs) to diagnose and treat sleep disorders. In the sleep laboratories, practitioners use instrumentation to monitor and record a patient's sleep states, stages and behaviors during sleep. Practitioners rely on these recordings to diagnose patients and prescribe proper therapies.

A goal of addressing sleep disorders is to help a person sleep better. Another goal of addressing sleep disorders is to help a person live longer. It is well known that various undesirable behaviors often occur during sleep such as snoring, apneas, abnormal breathing, Bruxism (teeth clenching and grinding) and the like. It is further known that these disorders and other undesirable behaviors can not only lead to insufficient amounts of sleep or fatigue but are also linked to co-morbidities such as obesity, diabetes, hypertension, cardiac diseases, stroke and SIDS, all of which can lead to a premature death. Serious efforts are being made to reduce or eliminate these undesirable disorders and behaviors in part because of these co-morbidity concerns.

Various stimulation controllers/systems are available in the art for altering undesirable behavior during sleep. These controllers/systems may be used to control a stimulation device. U.S. Pat. No. 5,540,733 to Testerman et al. discloses "[a] method for treating obstructive sleep apnea in a patient by electrical stimulation of muscles in the upper airway." In U.S. Pat. No. 7,115,097 to Johnson, "[a] notification system monitors changes in air flow channeled between a positive air pressure generator and a CPAP mask supplying positive airway pressure to a patient during treatment of sleep apnea." In U.S. Pat. No. 6,544,199 to Morris, "[a] system is provided for monitoring an undesired behavioral disorder such as Bruxism, jaw clenching, or snoring." In another example, U.S. Patent Publication No. US2006/0145878 to Lehrman et al. discloses "[a] System and method for treating obstructive sleep apnea by terminating an obstructive sleep apnea event before the cessation of breathing occurs."

It is well known that several states of sleep exist and involve varying levels of consciousness. It is further well known that the beneficial effects of sleep improve when it is uninterrupted. To the extent that the above controllers/systems and associated stimulation devices alter a patient's sleep state or in a worst-case scenario actually awaken a patient, the devices have gone too far. While they may have stopped the undesirable behavior, they have neither helped a person sleep better nor have they helped a person to live longer.

SUMMARY

There is a need to provide an apparatus and method that controls the stimulation of the central nervous system sufficiently to interrupt an undesirable neurological and/or sleep behavior by a means universally sensed by most patients where the device avoids significantly changing sleep states and certainly avoids waking a patient.

With the present subject matter, sleep therapy devices may be used in the absence of sleep lab personnel and practitioners who often make the adjustments to the devices on an ongoing basis. These adjustments include the initial patient setup, the intensity of stimulation, and the type of stimulation. Additional adjustment is necessary when the type of stimulation is varied to assure that the controlling device is correctly configured. Certain optimization adjustments are also made by practitioners. Thus, there is a need for an apparatus and method that automatically and autonomously optimizes its operation, as discussed in more detail below, so that there is no need for periodic patient or physician intervention.

The initial setup of the patient involves configuring the device based on an assessment of the patient with regard to the neurological and physiological condition of the patient. This process is somewhat of a big picture accuracy adjustment that makes sure the device is configured to properly address the correct sleep disorder taking into consideration the physical attributes and condition of the patient. In the absence of a practitioner, there is a need for a device with automatic and autonomous setup capabilities so the device can be correctly configured at the outset of treatment and begin to properly treat the patient.

A better understanding of the present subject matter may be gained from the following discussion regarding the adjustments relating to the intensity and type of stimulation. If the types of stimuli are applied with the same intensity, timing and duration on a repeated basis, there is a natural tendency to become habituated to them and then there is no reasonable assurance that the next stimulus is going to be effective to cause the patient to start resuming normal respiration. In a similar fashion, if the same type of stimulus is repeatedly applied, there is also a tendency to become habituated. In light of the precision needed in treating patients to avoid cortical arousal, there is a need to periodically, frequently or constantly vary the stimuli intensity and type in order for the stimuli to be noticed by the patient's central nervous system. In the absence of a practitioner, there is a need for the device to provide auto-adjusting, auto-optimizing and auto-dosing.

As different types of stimuli are used in sleep labs and in patient's homes, practitioners may use different controllers for different stimuli. Where a single controller is used, adjustments assure proper signals are sent to the stimulating device. As discussed above, in the absence of a practitioner, there is a need for auto-optimizing and thus a need for a device to be able to vary the stimuli provided. As such, there is also a need for a controller that is auto-adjusting so that the controller automatically adjusts for the different types and sensitivities of sensors and transducers that are being connected to a closed loop neuromodulator.

As also mentioned, practitioners often make certain optimizing adjustments to a controller to optimize the treatment being provided. In the absence of a practitioner, there is also a need for an apparatus and method that is auto-optimizing so that the controller automatically and immediately optimizes the application of therapy when physiological patient conditions change from day-to-day or between applications of individual therapies during each night sleep or session.

As sleep therapy devices continue to be used in the homes of patients, issues of "electronic smog" and electrostatic shock become a concern as patients handle and wear the devices, especially in dry climates and during the winter. Additionally, there is an increasing use of wireless technology such as wireless telephone transmissions, wireless routers, cordless phone systems, remote control burglar alarm devices, remote control toys, etc that could interfere with a sleep therapy device. Thus, there is also a need to provide an apparatus that is electronically hardened against the electronically harsh and hostile environments often encountered in modern life, modern homes and modern sleeping environments.

Additionally, patients' homes and sleeping environments are non-controlled environments. In a sleep lab or clinic, the same stimulus may be applied. In a home environment the sleeping patient may be subjected to external stimulus, passing trains, noisy bugs and kids, TV running while sleeping, snoring bed partner, noisy neighbors, honking cars, conversations by non sleeping people, high speed trains, car traffic, etc. the possibilities for sleeping patient arousal are countless. In certain predictable environments, the patents' central nervous system (CNS) has already gotten used to certain stimulus and has learned over time to tune them out consciously and subconsciously. However, other stimulus, both intermittent and chronic stimulus, are difficult to overcome including changes in individual patients based on physiology, mental state (mood etc), sensitivity to air pressure and other atmospheric parameters, sickness, disease, room decorations and bedding (sound dampening measures make the room quieter thus one can hear the stimulus better), time of day, season (people with allergies and hay fever will have different sensitivities to the stimulus dosages depending on their level of allergies or hay fever), noisy bed partners . . . etc.

A robust dosage optimization system works reliably and repeatedly on different patients, with different patient conditions, different moods, sickness, disease, different environments, time of day, locations (on average, the city of New York is louder than the city of Bismarck, N. Dak. and the device and the invention has to work equally well in either city), and over many years of use, preferably the entire lifespan of a human being once they start treatment using this apparatus and method.

Subjects that have an influence on patient's needs to, current and immediate dosing requirements:
Environmental (sound, noise, etc)
Health (disease, sickness, disability, etc)
Physical condition (earwax in the ear canal, stress, etc)
Physiological (hearing loss, etc)
Neurological (tinnitus, fibromyalgia, etc)
Seasonal (allergies, seasonal noise, etc)
Atmospheric (pressure, heat, humidity, etc)

Thus, there is a need for an apparatus and method that is capable of periodically, constantly and prescriptively changing (varying) an applied stimulus to interrupt a sleep disorder event. For example changing a stimulus type, stimulus level, stimulus rate, stimulus duration, stimulus sequence, level escalation, rate escalation duration escalation, or combination thereof.

There is a need to provide an apparatus and method to further ensure patient compliance with physicians prescribed treatments.

There is a need to provide an apparatus and method that controls the stimulation of the central nervous system sufficiently to interrupt an undesirable neurological and/or sleep behavior by a means universally sensed by most patients where the device avoids significantly changing sleep states and certainly avoids waking a patient. There is a need in the art to provide precise dosing of patients.

There is a need to provide an apparatus and method that controls the stimulation of the central nervous system sufficiently to interrupt an undesirable neurological and/or sleep behavior by a means universally sensed by most patients where the device avoids significantly changing sleep states and certainly avoids waking a patient.

There is a need to provide an apparatus that is capable of being used with a wide range of transducers. Additionally, there is a need for this device to be protected against electronically hostile environments involving EMI and ESD commonly found in homes.

There is a need to provide an apparatus and method that controls the stimulation of the central nervous system sufficiently to interrupt an undesirable neurological and/or sleep behavior by a means universally sensed by most patients where the device avoids significantly changing sleep states and certainly avoids waking a patient.

Also, as sleep therapy becomes more common, the devices used to treat it are beginning to extend beyond use in sleep labs and are often used right in a patient's own home. The sleep therapy devices are thus used in the absence of sleep lab personnel and practitioners who can read and interpret the device. Thus, there is a need for a device that indicates the input it is receiving, the functions it is performing, and the output it is transmitting. Moreover, devices that are used in homes may need to be initially set to function properly for given patient parameters. In these situations, a practitioner may need to use a sleep device in conjunction with a more sophisticated polysomnograph machine (PSG) in order to ensure that it is properly set. Thus, there is a need for the device to be compatible with a polysomnograph machine.

There is a need to provide an apparatus and method that controls the stimulation of the central nervous system sufficiently to interrupt an undesirable neurological and/or sleep behavior by a means universally sensed by most patients where the device avoids significantly changing sleep states and certainly avoids waking a patient.

Also, as sleep therapy becomes more common, the devices used to treat it are beginning to extend beyond use in sleep labs and are often used right in a patient's own home. The sleep therapy devices are thus used in the absence of sleep lab personnel and practitioners who often make the adjustments to the devices on an ongoing basis. Thus, there is a need in the art for a device that can properly operate and control a closed loop neuromodulator.

Finally, there is a need to provide an apparatus that is comfortable to wear, easy to set-up, and simple to use to further its ability to avoid alteration of sleep states.

Certain embodiments of the present subject matter provide a closed loop neuromodulator that by means of detecting the presence or absence of certain biological sensor signals provides dynamically and precisely dosed stimulation of the central nervous system in general and to the human central nervous system in specific by means of immediate biological feedback and appropriate stimulation of one or more of the five human senses.

In one embodiment, a closed loop neuromodulator includes an EMI/ESD hardened sensor interface, an activity detector, a stimulus timer, a stimulus escalator a stimulus generator, a stimulus sequencer, and an EMI/ESD hardened transducer driver.

In one embodiment, a method for dosage optimization in a closed loop neuromodulator includes monitoring a patient for an activity indicating a sleep disorder, applying a first stimulus based on a stored stimulus parameter to a patient once a sleep disorder is detected, rechecking the patient for continued activity indicating a sleep disorder, determining if the stimulus was an over stimulation or an under stimulation, and decreasing, increasing, or maintaining the stimulus parameter.

In another embodiment, determining whether the stimulus was an over stimulation or an under stimulation includes querying whether the patient has continued activity and if not, whether the stimulus was a first stimulus. In another embodiment, the method includes decreasing the stimulus parameter when the stimulus was an over stimulus and recording and storing a new stimulus parameter. In yet another embodiment, the method includes increasing the stimulus parameter when the stimulus was an under stimulus and recording and storing a new stimulus parameter. In still another embodiment, the method includes bypassing the increasing or decreasing of the stimulus parameter when the stimulus was an optimal stimulus.

In another embodiment, a diagnostic method of use of a stimulation controller includes connecting a closed loop neuromodulator to a patient, connecting a PSG machine to the stimulation controller, connecting a remote terminal to the stimulation controller, receiving information regarding the patient and the controller from a diagnostic interface and a PSG machine, and adjusting the parameters of the closed loop neuromodulator to optimize the controller for stimulating a patient or range of patients.

In another embodiment, a therapeutic method of use of a stimulation controller includes connecting a closed loop neuromodulator to a patient wherein the controller auto-adjusts and proceeds to optimize dosage based on a limited range of available parameters provided by a sleep professional.

In one embodiment, a virtual device development system like National Instruments CompactRIO running code that has been developed using National Instruments LabVIEW virtual development system including the wire terminations for the sensor and for the transducer is provided.

In another embodiment, a field programmable gate array (FPGA) with an internal processor, read-only memory (ROM), random access memory (RAM), reset management, an oscillator, an analog-to-digital converter, a digital-to-analog converter, configuration string, and wire terminals for the sensor and for the transducer is provided.

In another embodiment, a mixed signal micro controller like one of the ColdFire product line available from Freescale Semiconductors is executing code, command and algorithms developed with an appropriate software compiler is provided.

In another embodiment, a discrete circuit assembly consisting of a printed circuit board (PCB) populated with electronic components including the wire terminations for the sensor and for the transducer is provided.

In another embodiment, software residing inside a personal computer (PC) is executing code, command and algorithms developed with an appropriate software development system like C, C+ or C++, with an attached data acquisition system including the wire terminations for the sensor and for the transducer are provided.

In another embodiment, a custom integrated circuit like the one that is available from semiconductor houses is executing code, commands and algorithms developed on a silicon computer aided design (CAD) platform including the wire terminations for the sensor and for the transducer is provided.

In Example 1, a stimulus sequencer for generating a sleep therapy stimulus waveform for a patient includes a sequence address generator configured to receive a stimulus start signal from a timer of a closed loop neuromodulator and to provide an address related to a stimulus sequence of the sleep therapy, a sequence memory array coupled to the sequence address generator, the sequence memory array configured to select stimulus sequence information related to the address, a stimulus generator selector coupled to the sequence memory array, the stimulus generator selector configured to receive the stimulus sequence information from the sequence memory array, to receive a stimulus duration signal from the timer of the closed loop neuromodulator, and to provide a generator select signal to a stimulus generator of the closed loop neuromodulator using the stimulus sequence information and the stimulus duration signal, the generator select signal including stimulus type information related to stimulus pulses generated using the closed loop neuromodulator, and wherein the sleep therapy stimulus waveform includes a sequence of one or more stimulus types.

In Example 2, the closed loop neuromodulator of Example 1 is optionally configured to provide, in response to the stimulus start signal, a first stimulus to the patient using information from the stimulus sequencer, the first stimulus configured to not interrupt a detected sleep disorder event, and the closed loop neuromodulator of Example 1 is optionally configured to provide, following the first stimulus, a second stimulus to the patient using information from the stimulus sequencer, the second stimulus having more energy than the first stimulus and configured to interrupt the detected sleep disorder event.

In Example 3, the stimulus sequencer of any one or more of Examples 1-2 optionally includes a sequence address register configured to receive or provide stimulus address information using a control bus of the closed loop neuromodulator.

In Example 4, the stimulus sequencer of any one or more of Examples 1-3 optionally includes a sequence load control register configured to receive or provide a sequence load control command using a control bus of the closed loop neuromodulator.

In Example 5, the stimulus sequencer of any one or more of Examples 1-4 optionally includes a sequence load address register configured to receive or provide a sequence address load command using a control bus of the closed loop neuromodulator.

In Example 6, the stimulus sequencer of any one or more of Examples 1-5 optionally includes a sequence load data register configured to receive or provide a sequence data load command using a control bus of the closed loop neuromodulator.

In Example 7, the sequence memory array of any one or more of Examples 1-6 is optionally configured to select a stimulus sequence from a group comprising at least one of a fixed sequence, a sequential sequence, a circular sequence, a random sequence, a periodic sequence, a custom sequence, a patterned sequence, or a continuous sequence.

In Example 8, a system, for generating a sleep therapy stimulus waveform for a patient, of any one or more of Examples 1-7 optionally includes a sensor configured to detect information indicative of respiration from a patient, a closed loop neuromodulator configured to optimize sleep therapy for the patient, the closed loop neuromodulator including a stimulus sequencer configured to provide a generator select signal to a stimulus generator of the closed loop neuromodulator, the stimulus sequencer including a sequence address generator configured to receive a stimulus start signal from a timer of a closed loop neuromodulator and to provide an address related to a stimulus sequence of the sleep therapy, a sequence memory array coupled to the sequence address generator, the sequence memory array configured to select stimulus sequence information related to the address, a stimulus generator selector coupled to the sequence memory array, the stimulus generator selector configured to receive the stimulus sequence information from the sequence memory array, to receive a stimulus duration signal from the timer of the closed loop neuromodulator, and to provide a generator select signal to a stimulus generator of the closed loop neuromodulator using the stimulus sequence information and the stimulus duration signal, the generator select signal including stimulus type information related to stimulus pulses generated using the closed loop neuromodulator, wherein the sleep therapy stimulus waveform includes a sequence of one or more stimulus types, and a sequence address register configured to receive or provide stimulus address information using a control bus of the closed loop neuromodulator, a sequence load control register configured to receive or provide a sequence load control command using a control bus of the closed loop neuromodulator, a sequence load address register configured to receive or provide a sequence address load command using a control bus of the closed loop neuromodulator, and a sequence load data register configured to receive or provide a sequence data load command using a control bus of the closed loop neuromodulator, wherein the sequence memory array is configured to select a stimulus sequence from a group comprising at least one of a fixed sequence, a sequential sequence, a circular sequence, a random sequence, a periodic sequence, a custom sequence, a patterned sequence, or a continuous sequence, wherein the closed loop neuromodulator is configured to provide, in response to the stimulus start signal, a first stimulus to a transducer using information from the stimulus sequencer, the first stimulus configured to not interrupt a detected sleep disorder event, wherein the closed loop neuromodulator is configured to provide, following the first stimulus, a second stimulus to the transducer using information from the stimulus sequencer, the second stimulus having more energy than the first stimulus and configured to interrupt the detected sleep disorder event, and wherein the transducer is configured to deliver the first and second stimuli to the patient.

In Example 9, the sensor of any one or more of Examples 1-8 optionally includes at least one of a thermocouple, a thermistor, an air pressure transducer, an electrode, a respiratory effort belt, or a pyro/piezoelectric sensor, and the transducer of any one or more of Examples 1-8 optionally includes at least one of an acoustic transducer, a tactile mechanical agitator, an ocular stimulator, an electrical stimulator, a thermal stimulator, or an ultrasonic stimulator configured to modulate an audible signal onto an ultrasonic sound carrier.

In Example 10, a method, for generating a sleep therapy stimulus waveform for a patient, of any one or more of Examples 1-9 optionally includes receiving a stimulus start signal from a timer of a closed loop neuromodulator, providing an address related to a stimulus sequence of the sleep therapy, selecting stimulus sequence information related to the address from a sequence memory array, receiving the stimulus sequence information from the sequence memory array at a stimulus generator selector, receiving a stimulus duration signal from the timer of the closed loop neuromodulator at the stimulus generator selector, providing a generator select signal to a stimulus generator of the closed loop neuromodulator using the stimulus sequence information and the stimulus duration signal, the generator select signal including stimulus type information related to stimulus pulses generated using the closed loop neuromodulator, and wherein the sleep therapy stimulus waveform includes a sequence of one or more stimulus types.

In Example 11, the method of any one or more of Examples 1-10 optionally includes providing, in response to the stimulus start signal, a first stimulus to the patient using the generator select signal, the first stimulus configured to not interrupt a detected sleep disorder event; and providing, following the first stimulus, a second stimulus to the patient using the generator select signal, the second stimulus having more energy than the first stimulus and configured to interrupt the detected sleep disorder event.

In Example 12, the method of any one or more of Examples 1-11 optionally includes receiving or providing stimulus address information using a sequence address register coupled to a control bus of the closed loop neuromodulator.

In Example 13, the receiving or providing of any one or more of Examples 1-12 optionally includes receiving stimulus address information from a user or providing stimulus address information to the user.

In Example 14, the method of any one or more of Examples 1-13 optionally includes receiving or providing a sequence load control command using a sequence load control register coupled to a control bus of the closed loop neuromodulator.

In Example 15, the receiving or providing of any one or more of Examples 1-14 optionally includes receiving a sequence load control command from a user or providing a sequence load control command to a user.

In Example 16, the method of any one or more of Examples 1-15 optionally includes receiving or providing a sequence address load command using a sequence load address register coupled to a control bus of the closed loop neuromodulator.

In Example 17, the receiving or providing of any one or more of Examples 1-16 optionally includes receiving a sequence address load command from a user or providing a sequence address load command to a user.

In Example 18, the method of any one or more of Examples 1-17 optionally includes receiving or providing a sequence data load command using a sequence load data register coupled to a control bus of the closed loop neuromodulator.

In Example 19, the receiving or providing of any one or more of Examples 1-18 optionally includes receiving a sequence data load command from a user or providing a sequence data load command to a user.

In Example 20, the selecting stimulus sequence information related to the address of any one or more of Examples 1-19 optionally includes selecting a stimulus sequence from a group optionally includes at least one of a fixed sequence, a sequential sequence, a circular sequence, a random sequence, a periodic sequence, a custom sequence, a patterned sequence, or a continuous sequence.

Auto adjusting is the method by which the apparatus automatically and autonomously adjusts itself to the patient and to different sensor and transducer sensitivities.

Auto optimizing is the method by which the apparatus automatically and constantly optimizes its operation constantly during operation to the immediate and sometimes different patient conditions.

Auto dosing is the method by which the apparatus automatically and autonomously doses the right amount of therapeutic stimuli according to the needs of the individual patient for optimal comfort and performance.

The apparatus issues specific doses and types of stimuli to the patient until the resumption of breathing has been detected.

A neuromodulator includes a controller that applies stimuli and where a patient's central nervous system forms a feedback loop to assist in the modulation or adjustment of the stimuli.

While the present disclosure is directed toward treatment of sleep disorders, further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The forgoing features, objects and advantages of the invention will become apparent to those skilled in the art from the following detailed description, especially when considered in conjunction with the accompanying drawings in which like the numerals in the several views refer to the corresponding parts:

FIG. 3A illustrates generally an electrical block diagram of an EMI/ESD Hardened Sensor Interface.

FIG. 4A illustrates generally an electrical block diagram of an Activity Detector.

FIG. 5A illustrates generally an electrical block diagram of a Stimulus Timer.

FIG. 7A illustrates generally an electrical block diagram of a Stimulus Generator.

FIG. 8A illustrates generally an electrical block diagram of a Stimulus Escalator.

FIG. 9B is a detailed electrical block diagram of an EMI/ESD Hardened Transducer Driver according to one example of the present subject matter.

FIG. 10A illustrates generally an electrical block diagram of a Diagnostic Indicators and PSG Interface.

FIG. 12A illustrates generally an electrical block diagram for implementation in a virtual product development platform of a sleep diagnostic closed loop neuromodulator according to one example of the present subject matter.

FIG. 12B illustrates generally an electrical block diagram for implementation in a Field Programmable Gate Array (FPGA) of a sleep diagnostic closed loop neuromodulator according to one example of the present subject matter.

FIG. 12C illustrates generally an electrical block diagram for implementation in a Mixed Signal Micro Controller of a sleep diagnostic closed loop neuromodulator according to one example of the present subject matter.

FIG. 12D illustrates generally an electrical block diagram for implementation in a Custom Integrated Circuit (IC) of a sleep diagnostic closed loop neuromodulator according to one example of the present subject matter.

FIG. 12E illustrates generally an electrical block diagram for implementation in a Discrete Component Printed Circuit Board Assembly (PCB) of a sleep diagnostic closed loop neuromodulator according to one example of the present subject matter.

FIG. 12F illustrates generally an electrical block diagram for software based implementation in a Personal Computer of a sleep diagnostic closed loop neuromodulator according to one example of the present subject matter.

FIG. 12I illustrates generally an electrical block diagram for implementation in a Mixed Signal Micro Controller of a sleep therapy closed loop neuromodulator according to one example of the present subject matter.

FIG. 12J illustrates generally an electrical block diagram for implementation in a Custom Integrated Circuit (IC) of a sleep therapy closed loop neuromodulator according to one example of the present subject matter.

FIG. 12K illustrates generally an electrical block diagram for implementation in a Discrete Component Printed Circuit Board Assembly (PCB) of a sleep therapy closed loop neuromodulator according to one example of the present subject matter.

FIG. 12L illustrates generally an electrical block diagram for software based implementation in a Personal Computer (PC) of a sleep therapy closed loop neuromodulator according to one example of the present subject matter.

DETAILED DESCRIPTION

The following detailed description relates to a closed loop neuromodulator directed toward treating patients with sleep disorders. The closed loop neuromodulator is more particularly directed at stimulating a patient to interrupt and terminate an undesired sleep behavior or condition such as snoring, obstructive sleep apnea, central sleep apnea, complex sleep apnea, snoring, restless leg syndrome (RLS), periodic limb movement (PLM), Bruxism (teeth grinding and clenching), sudden infant death syndrome (SIDS) and other neurological disorders not necessarily related to sleep. The closed loop neuromodulator may be used in conjunction with a sensor and a transducer affixed to a patient. The sensor transmits respiratory information to the closed loop neuromodulator that analyzes the information, adjusts to the patient during a first use, applies a proper and precise stimulation type and dosage, and optimizes its operation and transducer output dosing depending on the past and present sensor information received. The dosage may be adjusted based on at least the following parameters: 1. Stimulus Type, 2. Stimulus Rate, 3. Stimulus Duration, 4. Stimulus Level, 5. Stimulus Escalation, 6. Stimulus Sequence.

The controller counts the amount of applied pulses and measures the time observed to cause the resumption of breathing in a sleeping person. The number of pulses and amount of time elapsed until the resumption of breathing is a direct measure for the effectiveness of the applied pulse stimuli. The number of pulses, intensity of stimulation and time observed to cause the resumption of breathing must be at a minimum in order to obtain optimal results. When the number of stimuli pulses exceeds a limit, then the signal level of the new stimuli for the next breathing cessation event increases automatically. When the number of stimuli pulses falls below a lower limit, then the signal level of the new stimuli for the next breathing cessation event reduces automatically.

The following detailed description includes discussion of sensors and transducers affixed to patients. Additionally, elements of a closed loop neuromodulator are discussed including an electromagnetic interference/electrostatic discharge (EMI/ESD) hardened sensor Interface, an Activity Detector, a stimulus timer, a stimulus escalator; a stimulus generator, a stimulus sequencer, and an EMI/ESD hardened transducer driver. Information regarding the waveforms and timing signals received and generated are also included.

The present invention can be readily understood from FIGS. 1 through 19.

Figure 1A:
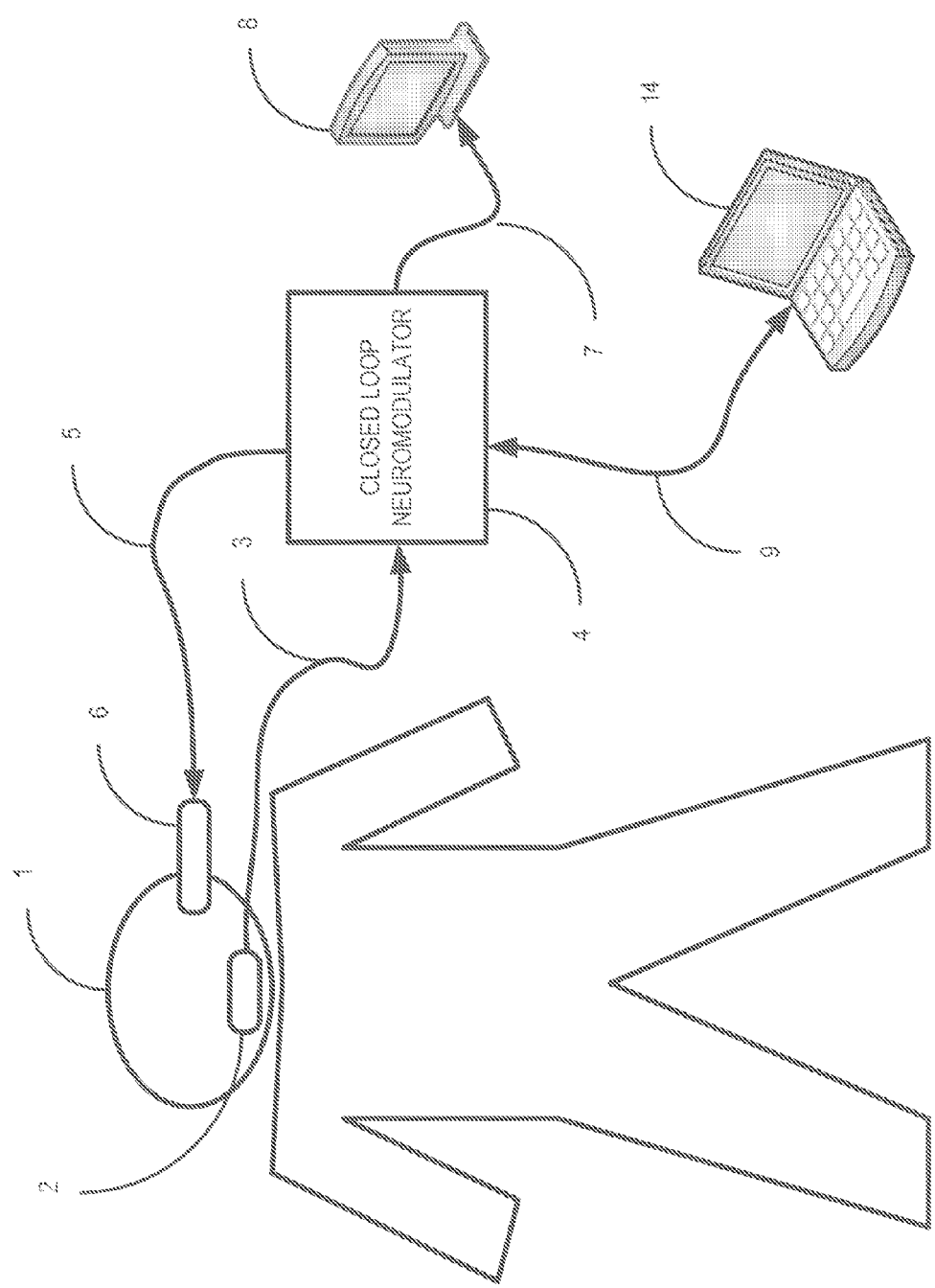
FIG. 1A is a configuration diagram of a sleep diagnostic closed loop neuromodulator in place on a sleep patient according to one example of the present subject matter.

FIG. 1A shows an overall use and configuration of a sleep diagnostic closed loop neuromodulator according to one example of the present subject matter. A typical sleep diagnostic patient 1 suffering from a sleep disorder has been outfitted with a sensor 2 to measure respiratory effort. A pair of sensor output wire leads 3 connects the sensor to the input of the controller device 4. The output of the controller 4 connects via a pair of wire leads 5 to the transducer 6. Another output of the controller 4 connects via a set of wire leads 7 to a sleep lab PSG machine 8. A remote diagnostic input/output port of the controller 4 connects via a set of wire leads 9 to a remote diagnostic terminal 14.

Preferably, the sensor 2 of FIG. 1A is a piezoelectric sensor constructed in accordance with the teachings of U.S. Pat. Nos. 5,311,875 and 6,254,545 to Stasz, the teachings of which are hereby incorporated by reference as if fully set forth herein. Those skilled in the art will understand and appreciate that various sensors are known including, but not limited to thermocouples, thermistors, air pressure transducers, electrodes and respiratory plethysmography inductance (RIP) belts and that these sensors are within the scope of the invention.

The transducer shown in FIG. 1A is preferably an aural ear-bud type transducer, a tactile mechanical agitator, an ocular stimulator, or an ultrasonic stimulator based on modulating an audible signal onto an ultrasonic sound carrier. For example, the transducer may be an agitator as described in the U.S. Provisional Patent Application titled Agitator to Stimulate the Central Nervous System, filed on May 2, 2008 with Ser. No. 61/049,802, the contents of which are hereby incorporated by reference herein. Those skilled in the art will understand and appreciate that various transducers exist for stimulating central nervous systems and are thus within the scope of the present invention.

Figure 1B:
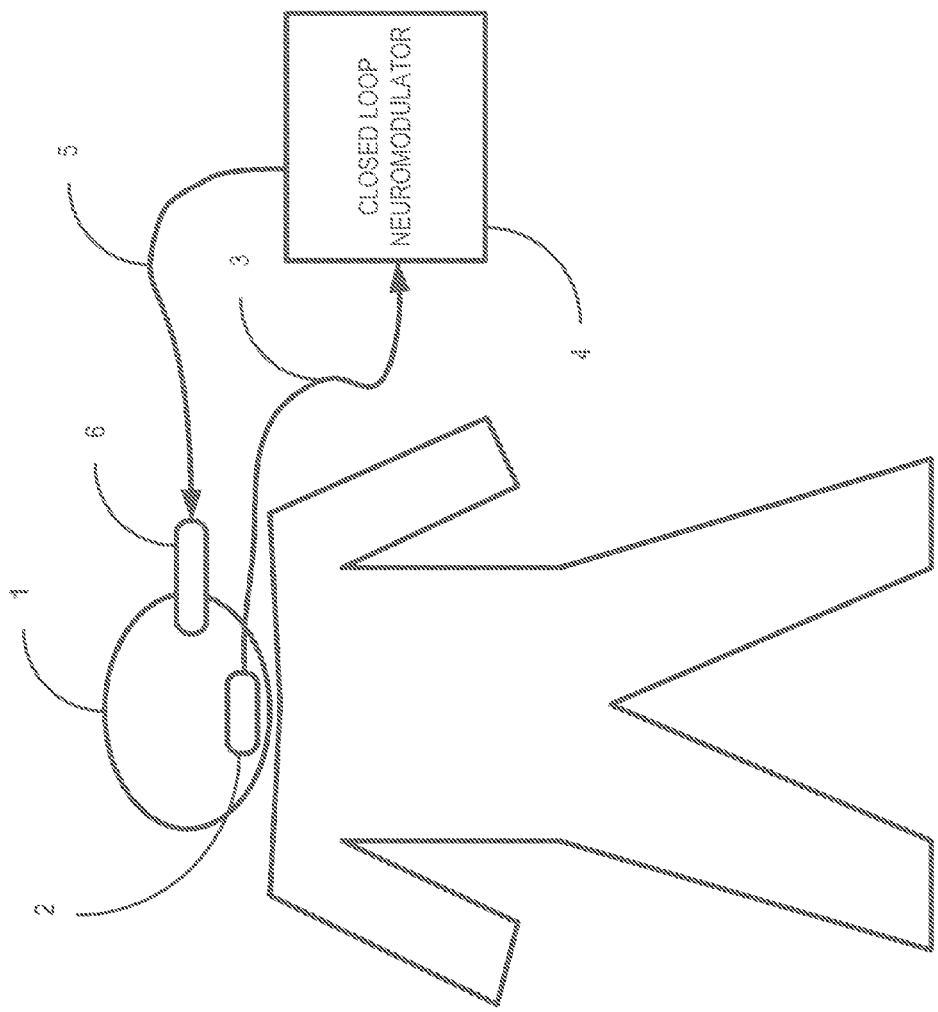
FIG. 1B is a configuration diagram of a sleep therapy closed loop neuromodulator in place on a sleep patient according to one example of the present subject matter.

FIG. 1B shows an overall use and configuration of a sleep therapy closed loop neuromodulator according to one example of the present subject matter. A sleep therapy patient 1 suffering from a sleep disorder has been outfitted with a sensor 2 to measure respiratory effort. A pair of sensor output wire leads 3 connects the sensor to the input of the controller device 4. The output of the controller 4 connects via a pair of wire leads 5 to the transducer 6.

Preferably, the sensor 2 of FIG. 1B is a piezoelectric sensor constructed in accordance with the teachings of U.S. Pat. Nos. 5,311,875 and 6,254,545 to Stasz, the teachings of which are hereby incorporated by reference as if fully set forth herein. Those skilled in the art will understand and appreciate that various sensors are known including, but not limited to thermocouples, thermistors, air pressure transducers, electrodes and respiratory effort belts, pyro/piezoelectric sensors and that these sensors are within the scope of the invention.

The transducer shown in FIG. 1B is preferably an aural ear-bud type transducer, a tactile mechanical agitator, an ocular stimulator, or an ultrasonic stimulator based on modulating an audible signal onto an ultrasonic sound carrier. For example, the transducer may be an agitator as described in the U.S. Provisional Patent Application titled Agitator to Stimulate the Central Nervous System, filed on May 2, 2008 with Ser. No. 61/049,802, the contents of which are hereby incorporated by reference herein. Those skilled in the art will understand and appreciate that various transducers exist for stimulating central nervous systems and are thus within the scope of the present invention.

Figure 2A:
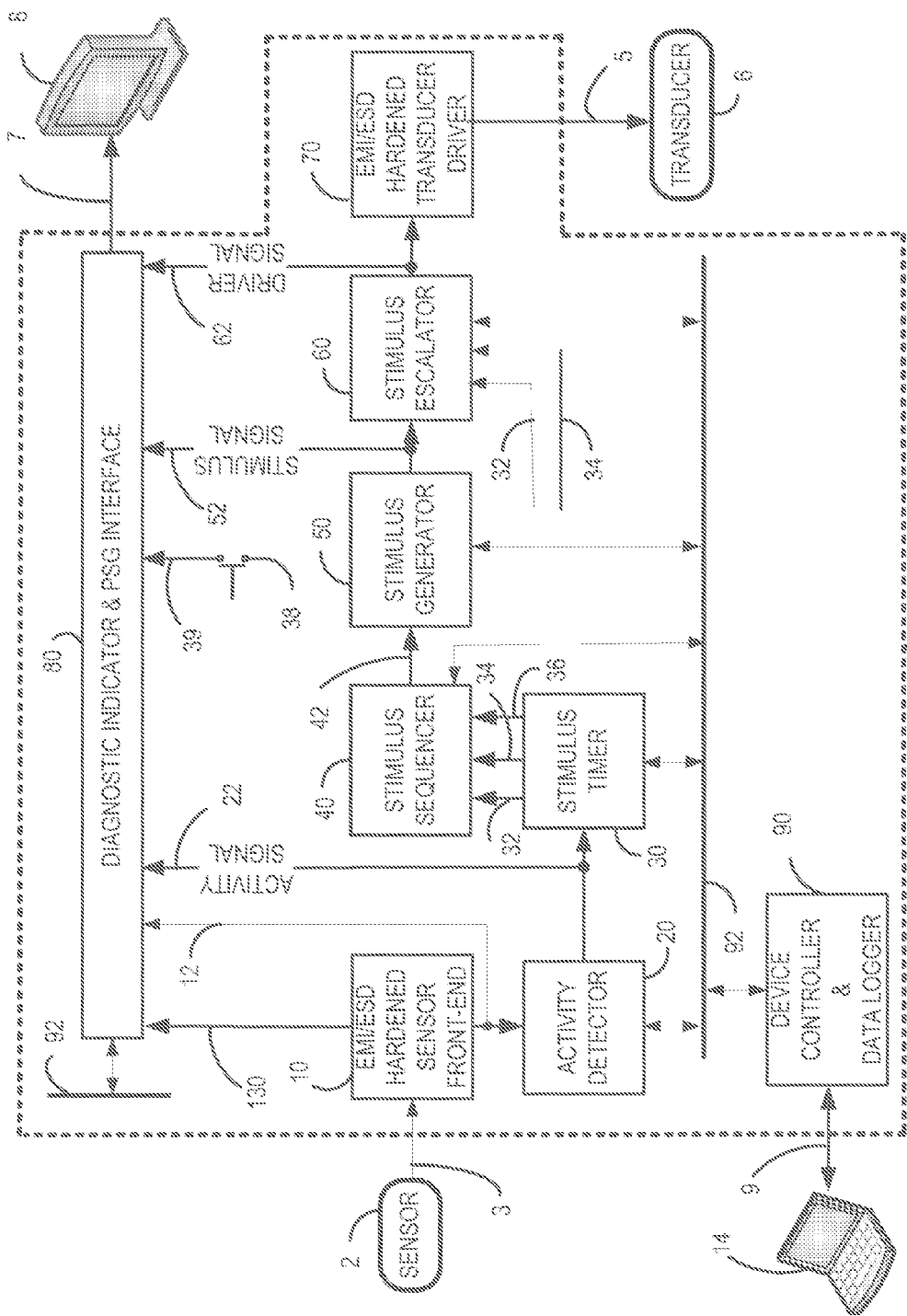
FIG. 2A illustrates generally an electrical block diagram of a sleep diagnostic closed loop neuromodulator.

Referring to FIG. 2A, there is indicated generally by numeral 4 a block diagram of the sleep diagnostic closed loop neuromodulator along with a sensor 2 and a transducer 6. Attached to the sensor and sleep diagnostic closed loop neuromodulator is a pair of wire terminations 3 via which the sleep diagnostic closed loop neuromodulator receives the sensor output. Attached to the transducer and sleep diagnostic closed loop neuromodulator is a pair of wire terminations 5 via which the sleep diagnostic closed loop neuromodulator transmits the transducer input. A sleep lab PSG machine 8 connects to the controller 4 connects via a set of wire leads 7. A remote diagnostic terminal 14 connects to the controller 4 via a set of wire leads 9. Furthermore the sleep diagnostic closed loop neuromodulator indicated generally by numeral 4 contains an EMI/ESD hardened sensor Interface 10, an activity detector 20, a stimulus timer 30, a stimulus sequencer 40, a stimulus generator 50, a stimulus escalator 60, an EMI/ESD hardened transducer driver 70, a diagnostic indicator and PSG interface 80, and a device controller and data logger 90.

Figure 2B:
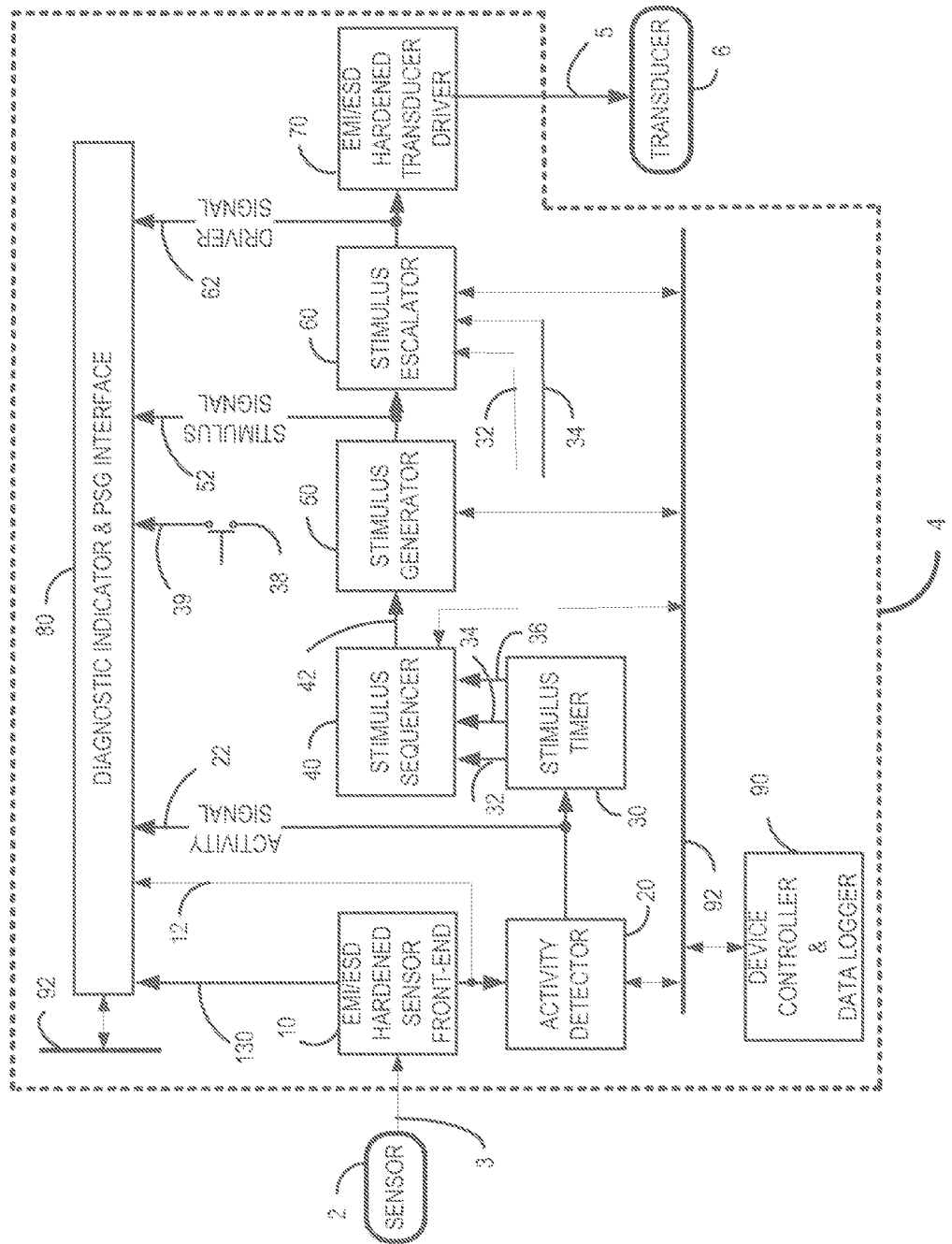
FIG. 2B is an electrical block diagram of the sleep therapy closed loop neuromodulator according to one example of the present subject matter.

Referring to FIG. 2B, there is indicated generally by numeral 4 a block diagram of the sleep therapy closed loop neuromodulator along with a sensor 2 and a transducer 6. Attached to the sensor and sleep therapy closed loop neuromodulator is a pair of wire terminations 3 via which the sleep therapy closed loop neuromodulator receives the sensor output. Attached to the transducer and sleep therapy closed loop neuromodulator is a pair of wire terminations 5 via which the sleep therapy closed loop neuromodulator transmits the transducer input. Furthermore the sleep therapy closed loop neuromodulator indicated generally by numeral 4 contains an EMI/ESD hardened sensor Interface 10, an activity detector 20, a stimulus timer 30, a stimulus sequencer 40, a stimulus generator 50, a stimulus escalator 60, an EMI/ESD hardened transducer driver 70, a diagnostic indicator and PSG interface 80, and a device controller and data logger 90.

EMI/ESD Hardened Sensor Interface

Even though most countries have legal requirements that mandate EMC compliance, electronic devices must still work correctly when subjected to certain amounts of electromagnetic interference (EMI), and should not emit EMI, which could interfere with other equipment. This issue is known in the industry as self-compatibility and this fact is crucial to the operation of the invention because of the very low analog biomedical signals involved.

A robust sleep therapy system works reliably in a modern harsh and hostile environment in close proximity to cell phone transmissions, wireless internet transmitters, wireless phone system transmitters, etc. Modern environments, even home environments have high concentration of EMI and RFI especially in the 60 Hz/120 Hz due to home power wiring and fluorescent, compact fluorescent lighting and switch mode power supplies operating in home appliances. Additionally, wireless technology such as wireless telephone transmissions, wireless routers, cordless phone systems, remote control burglar alarm devices, remote control toys, and the like may emit EMI. Issues of self-compatibility are also a concern and involve minimizing the emission of EMI that could interfere with other portions of the device or other equipment. Thus, EMI that could interfere with a sleep device is a concern, but the EMI emitted by the device is also a concern. ESD hardening protects sensitive electronics due to common and regular handling of the product containing the sensitive electronics in a standard home environment where static discharges are common, especially during the winter seasons in colder climate zones and during the dry seasons in warmer climate zones.

EMI/ESD hardening against the aforementioned offenders not only satisfies domestic and international requirements on emissions and susceptibility but also results in robust operation, cleaner internal signals, improved signal to noise ratio (SNR) and greater dynamic range.

In one embodiment, an EMI/ESD hardened sensor interface includes a sensor input connector, at least one EMI/RFI filter, a grounded metal shield, an ESD protection device, a supply filtered balanced signal amplifier, a supply filtered signal filter, and a supply filtered analog to digital converter.

In another embodiment, the EMI/ESD hardened sensor interface the EMI/RFI filter includes an external EMI/RFI filter and an internal EMI/RFI filter. In another embodiment, the external EMI/RFI filter is situated along the signal path outside the grounded metal shield. In yet another embodiment, the internal EMI/RFI filter is situated along the signal path inside the grounded metal shield. In yet another embodiment, each of the elements of the interface are arranged series and the grounded metal shield encloses the internal EMI/RFI filter, the ESD protection device, the balanced signal amplifier, the signal filter, and the analog to digital converter.

In another embodiment, a method is provided including sensing a behavior of a patient and filtering, amplifying, and converting the signal from an analog to a digital signal is also provided. In this embodiment, the signal may also be output to a diagnostic indicator and PSG interface.

Referring to FIG. 3A, there is indicated more specifically by numeral 10 an EMI/ESD hardened Sensor Interface. The EMI/ESD hardened sensor Interface 10 is designed to interface with a multitude of different types of respiratory sensors 2. For example, but not limited to, polyvinylidene fluoride film (PVDF) sensors, thermocouples, thermistors, air pressure transducers, electrodes and respiratory effort belts, and pyro/piezoelectric sensors all could be used and connected via the pair of sensor wire terminations 3 to the EMI/ESD hardened sensor Interface 10 in order to detect respiratory flow. The term, the causes and the subject of EMI/ESD are well known to someone skilled in the art. The EMI/ESD hardened sensor Interface 10 comprises a multitude of EMI/ESD countermeasures in order to ensure that the sensor signal 3 will be detected, processed and decoded correctly by this invention without suffering from the adverse affects of EMI and ESD. The EMI/ESD hardened sensor Interface 10 connects via the digital airflow signal 12 to the activity detector. Furthermore, the EMI/ESD hardened sensor Interface 10 connects via the analog airflow signal 130 to the Diagnostic Indicator and PSG Interface. A detailed description of the EMI/ESD hardened sensor Interface 10 is provided below and in a separately filed U.S. Provisional Patent Application titled EMI/ESD Hardened Sensor Interface for a closed loop neuromodulator, filed on Aug. 22, 2008, the contents of which are hereby incorporated by reference herein.

The relationship between the analog airflow signal and digital airflow signal is shown near the bottom of FIG. 3A, where the positive sloping portion of the analog signal is converted to inhalation in the digital signal and the negative sloping portion of the analog signal is converted to exhalation in the digital signal. As discussed above, an analog airflow activity signal indicating the inhalation and exhalation duration and waveforms may allow a sleep lab practitioner to process the signal further with a PSG in order to make a more detailed diagnosis. A digital airflow activity signal indicating the inhalation and exhalation duration may allow a sleep lab practitioner to see directly on the machine, via LED's or other indicators, the patient's respiratory activity and possibly at which point of the respiration cycle the patient has stopped breathing.

An analog airflow activity signal is provided indicating the inhalation duration and exhalation waveforms so that the sleep lab practitioner can process the signal further with a PSG in order to make a more detailed diagnosis.

A digital airflow activity indicator is provided indicating the inhalation duration and exhalation duration so that the sleep lab practitioner can see directly on the machine the patient's respiratory activity and possibly at which point of the respiration cycle the patient has stopped breathing.

Figure 3B:
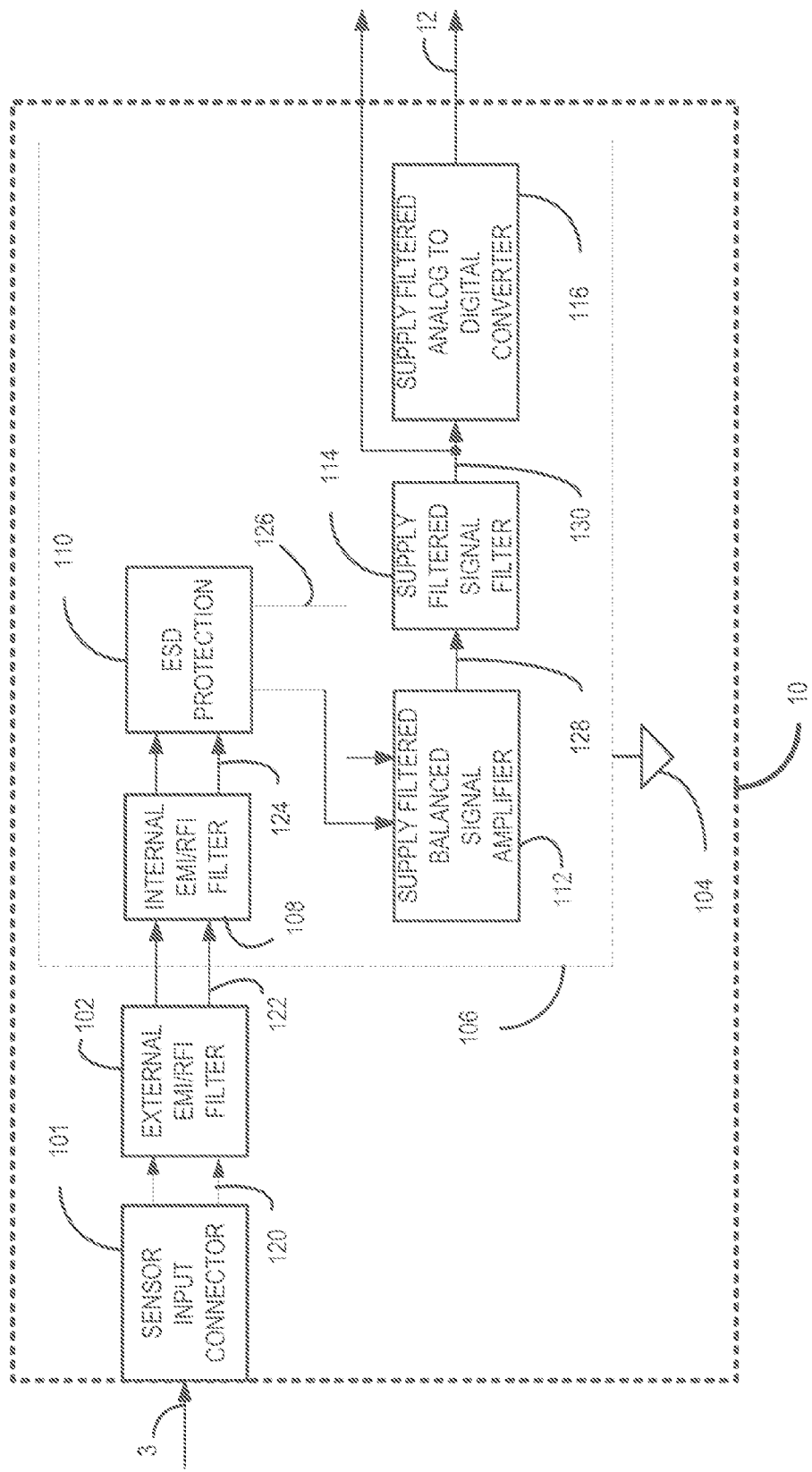
FIG. 3B is a detailed electrical block diagram of an EMI/ESD Hardened Sensor Interface according to one example of the present subject matter.

Referring to FIG. 3B, there is indicated more specifically by numeral 10 a detailed block diagram of an EMI/ESD hardened sensor interface according to certain embodiments. The sensor interface includes a sensor input connector 101, external and internal EMI/RFI filters 102, 108, ESD protection 110, a supply filtered balanced signal amplifier 112, a supply filtered signal filter 114, and a supply filtered analog to digital converter 116. Also included is a metal shield 106.

The sensor input connector 101 provides an input termination for a pair of wire leads 3 extending from an external sensor 2. The sensor input connector may consist of an outlet for plugging in the wire leads 3. The sensor input connector 101 may be connected to an external EMI/RFI Filter via its signal wire pairs 120.

The external EMI/RFI filter 102 provides an initial level of EMI/RFI protection by filtering out high frequency EMI and RFI. This may include, but is not limited to, EMI and RFI from electronic devices such as pagers, wireless internet connections, cordless phones, cellular phones, and the like. The external EMI/RFI may be configured to filter out interference ranging from approximately 100 MHz to 10 GHz. The external EMI/RFI filter may be connected to an internal EMI/RFI filter via wire pairs 122.

The wire pairs 122 extending from the external EMI/RFI filter may penetrate the wall of a metal shield 106 and further extend to the internal EMI/RFI filter. The circuit covering metal shield 106 may surround several elements of the device including the internal EMI/RFI filter 108, the ESD protection 110, the supply filtered balanced signal amplifier 112, supply filtered signal filter 114, and supply filtered analog to digital converter 116. The metal shield 106 may provide an internal environment shielded against interference. The metal shield 106 is connected to a multitude of ¼" spaced ground connections 104 for providing a good and solid ground connection even at extremely high frequencies.

The wire pairs 122 extending from the external EMI/RFI filter may penetrate the wall of the metal box 106 and may further extend to the internal EMI/RFI filter. As such, the wire pairs 122 may act as a conduit for interference to enter the protective metal box 106. Thus, the internal EMI/RFI filter 108 may act as a second level of protection against interference and may be directed at filtering conducted emissions and common mode emissions. This filter 108 may be configured to filter out interference ranging from about 2 KHZ to 500 MHz. The internal EMI/RFI filter 108 may be connected to the ESD protection 110 via wire pairs 124.

The ESD protection 110 may provide a barrier to electrostatic shock. By dissipating high levels of energy entering the device, the ESD protection 110 may protect the device from damage due to such surges of energy. The ESD protection 110 may be connected to a supply filtered balanced signal amplifier 112 with wire pair 126.

The supply filtered balanced signal amplifier 112 may be configured to filter out any internal interference emitted by internal elements of the device. In fact, each of the remaining elements of the EMI/ESD Hardened sensor interface including the balanced signal amplifier 112, signal filter 114, and analog to digital conversion may all be configured to filter out this internal interference further adding to the self-compatibility of the device.

The supply filtered balanced signal amplifier 112 may be further configured to amplify the incoming signal. The biological signals received from a patient are commonly low energy signals. Having filtered out most of the interference, the signal may be amplified without also amplifying associated noise. As such, the signal may be made more identifiable and more appropriate for analysis. The supply filtered balanced signal amplifier 112 may be connected to the supply filtered signal filter 114 via single wire 128.

It is noted here that wire pairs 3, 120, 122, 124, and 126 may be configured, as is well known in the art, to rely on each other to cancel out certain amounts of interference. The current connection 128 may be a single wire connection because of the internal environment provided by metal shield 106 and the upstream filters.

The supply filtered signal filter 114 may receive the amplified signal from the supply filtered balanced signal amplifier 112 via the connection 128. As mentioned above, the supply filtered signal filter 114 may also be configured to filter out internal interference. In addition, the supply filtered signal filter is configured to filter out artifacts of the biological signal. These artifacts may include signals picked up by the sensor 2 and included in the signal transmitted to the stimulation controller. These artifacts may be an associated heart rate of a patient, other noises or movements in a room, or other signals picked up by the sensor in addition to the signal intended. With knowledge of the range of frequencies expected to be received from a particular sensor, based on the condition being monitored, the supply filtered signal filter 114 may filter out those frequencies not pertinent to the analysis. For example, if breathing is being monitored, a range of the expected frequency of breathing can be used to eliminate signals outside that range. The supply filtered signal filter may be connected to a supply filtered analog to digital converter via wire 130.

The supply filtered analog to digital converter 116 may be configured, like the balanced signal amplifier 112 and the signal filter 114, to filter out internal interference. In addition, the analog to digital converter 116 may convert the signal from an analog signal to a digital signal by converting positive sloping portions of a breathing curve to a digital inhalation signal and by converting negative sloping portions of a breathing curve to a digital exhalation signal.

It is noted here that connection 130, extending from the signal filter 114 to the analog to digital converter 116, may be split so as to provide an output of the fully filtered analog signal to a diagnostic indicator and PSG interface prior to converting the signal to a digital signal. The digital signal then, may be output via connection 112 to the diagnostic indicator and PSG interface and also to additional elements of a stimulation controller.

Figure 3C:
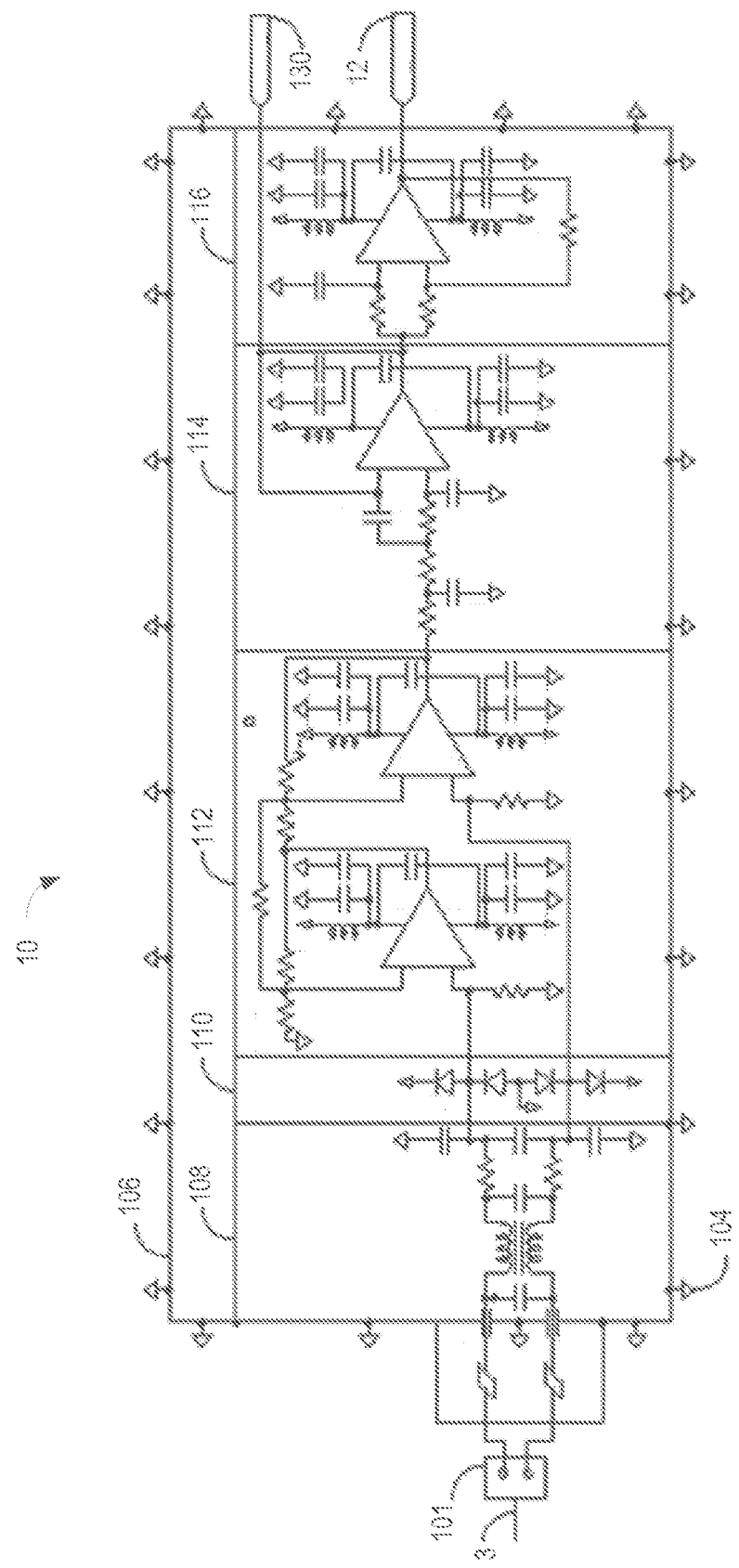
FIG. 3C is an electrical schematic diagram of an EMI/ESD Hardened Sensor Interface according to one example of the present subject matter.

Referring to FIG. 3C there is indicated more specifically by numeral 10 a detailed schematic diagram of the EMI/ESD hardened sensor Interface. The sensor input connector 101 comprises of connector J1 with the two-signal wire pair leads designated as pin 1 and pin 2 respectively. The external EMI/RFI 102 filter comprises of a pair of ferrite beads FB1 and FB2 acting as the filter series element, and of a pair of metal shield penetrating feed-through capacitors C1 and C2 as the parallel element to ground for common mode filtering. The metal shield 106 covers the sensitive signal carrying analog signal circuit and is connected to a multitude of ¼" spaced ground connections 104 for providing a very low impedance connection to circuit ground even at extremely high frequencies. The metal shield 106 in connection with the printed circuit ground plane on the opposite side of the PCB and with an RF tight picket fence constructed of interleaved vias that connect the ground plane to the ground flooded top component copper layer forms a continuous electrostatic shield around the entire volume of the EMI/ESD hardened sensor Interface 10. The internal EMI/RFI filter 108 comprises a differential mode filtering capacitor C3 connected to C1 and C2. Also connected to C1 and C2 is the input wire pair of a high frequency common mode choke L1. The output wire pair of the high frequency common mode choke L1 is connected to the input of the two ESD energy absorbing series resistors R1 and R2 and to a second filter capacitor C4. The output wire pair of the energy absorbing resistors R1 and R2 is connected to another set of EMI suppressing filter capacitors C5, C6 and C7. The ESD protection 110 comprises primarily of diodes D1, D2, D3 and D4. The cathode of D1 is connected to the positive supply terminal. The anode of D1 is connected to the non-inverting input terminal 3 of opamp U1. The anode of D2 is connected to the negative supply terminal. The cathode of D2 is connected to the non-inverting input terminal 3 of opamp U1. The cathode of D4 is connected to the positive supply terminal. The anode of D4 is connected to the non-inverting input terminal 3 of opamp U2. The anode of D3 is connected to the negative supply terminal. The cathode of D3 is connected to the non-inverting input terminal 3 of opamp U2. D1 through D4 present the parallel clamping element of the ESD protected opamp input terminal. Resistors R1 and R2 in connection with the Diodes D1, D2, D3 and D4 form an ESD suppression circuit. Resistors R1 and R2 form the series ESD power absorbing elements. It is clearly shown that the input terminal 3 node of the operational amplifier U1 and U2 of the supply filtered balanced signal amplifier 112 are thus EMI and ESD protected. The supply filtered balanced signal amplifiers 112 comprise of operational amplifiers (opamps) U1 and U2. Both opamps U1 and U2 are connected in a two-amplifier instrumentation amplifier configuration. The four gain setting resistors RP1:A, RP1:B, RP1:C and RP1:D are closely matched (typically to 0.1%) within the same single resistor package so to provide the maximum amount of common mode rejection. Resistor R4 by means of connection to signal ground provides the input signal load for the J1.1 signal. Resistor R8 by means of connection to signal ground provides the input signal load for the J1.2 signal. Negative supply filtering of the operational amplifier U1 comprises of a conducted RF power absorbing inductor L2 and a conducted RF power suppressing cascaded capacitor bank consisting of C8 and C10 in parallel to ground. The conducted RF power absorbing inductor L2 is connected in series with the negative supply power terminal V− and the negative power supply terminal 2 of the operational amplifier U1. Positive supply filtering of the operational amplifier U1 comprises of a conducted RF power absorbing inductor L3 and a conducted RF power suppressing cascaded capacitor bank consisting of C9 and C12 in parallel to ground. The conducted RF power absorbing inductor L3 is connected in series with the positive supply power terminal V+ and the positive power supply terminal 5 of the operational amplifier U1. Furthermore, conducted emissions bypassing capacitor C11 is connected across the U1 operational amplifier power pin 2 and pin 5. Negative supply filtering of the operational amplifier U2 comprises of a conducted RF power absorbing inductor L4 and a conducted RF power suppressing cascaded capacitor bank consisting of C13 and C15 in parallel to ground. The conducted RF power absorbing inductor L4 is connected in series with the negative supply power terminal V− and the negative power supply terminal 2 of the operational amplifier U2. Positive supply filtering of the operational amplifier U2 comprises of a conducted RF power absorbing inductor L5 and a conducted RF power suppressing cascaded capacitor bank consisting of C14 and C17 in parallel to ground. The conducted RF power absorbing inductor L5 is connected in series with the positive supply power terminal V+ and the positive power supply terminal 5 of the operational amplifier U2. Furthermore, conducted emissions bypassing capacitor C16 is connected across the U2 operational amplifier power pin 2 and pin 5. The single ended output of the supply filtered balanced signal amplifier 112 is available at the pin 1 of operational amplifier U2. The output of the supply filtered balanced signal amplifier 112 connects to the input of the supply filtered signal filter 114. The supply filtered signal filter 114 is configured as a $3^{rd}$ order Butterworth low pass filter by means of filter series element resistors R10, R11 and R12 and by means of filter parallel elements C18, C19 and C20. Negative supply filtering of the operational amplifier U3 comprises of a conducted RF power absorbing inductor L6 and a conducted RF power suppressing cascaded capacitor bank consisting of C21 and C23 in parallel to ground. The conducted RF power absorbing inductor L6 is connected in series with the negative supply power terminal V− and the negative power supply terminal 2 of the operational amplifier U3. Positive supply filtering of the operational amplifier U3 comprises of a conducted RF power absorbing inductor L7 and a conducted RF power suppressing cascaded capacitor bank consisting of C22 and C25 in parallel to ground. The conducted RF power absorbing inductor L7 is connected in series with the positive supply power terminal V+ and the positive power supply terminal 5 of the operational amplifier U3. Furthermore, conducted emissions bypassing capacitor C24 is connected across the U3 operational amplifier power pin 2 and pin 5. The single ended output of the supply filtered signal filter 114 is available at the pin 1 of operational amplifier U3. The output of the supply filtered signal filter 114 connects to the input of the supply filtered analog to digital converter 116. The supply filtered analog to digital converter 116 is configured as a self-referencing phase detector by means of phase shifting series element resistors R13 and by means of phase shifting parallel element C26 feeding into the inverting and non-inverting inputs of opamp U4. The signal detection threshold of the self-referencing phase detector is set by the ratio of resistor R15 to R14. A ratio of 0.01 has been found to be working optimally in this application. Negative supply filtering of the operational amplifier U4 comprises of a conducted RF power absorbing inductor L8 and a conducted RF power suppressing cascaded capacitor bank consisting of C27 and C29 in parallel to ground. The conducted RF power absorbing inductor L8 is connected in series with the negative supply power terminal V− and the negative power supply terminal 2 of the operational amplifier U4. Positive supply filtering of the operational amplifier U4 comprises of a conducted RF power absorbing inductor L9 and a conducted RF power suppressing cascaded capacitor bank consisting of C28 and C31 in parallel to ground. The conducted RF power absorbing inductor L9 is connected in series with the positive supply power terminal V+ and the positive power supply terminal 5 of the operational amplifier U4. Furthermore, conducted emissions bypassing capacitor C30 is connected across the U4 operational amplifier power pin 2 and pin 5. The single ended output of the supply filtered analog to digital converter 116 is available at the pin 1 of operational amplifier U4. The single ended output 12 of the supply-filtered analog to digital converter 116 connects to the input of the Activity Detector 20.

Figure 3D:
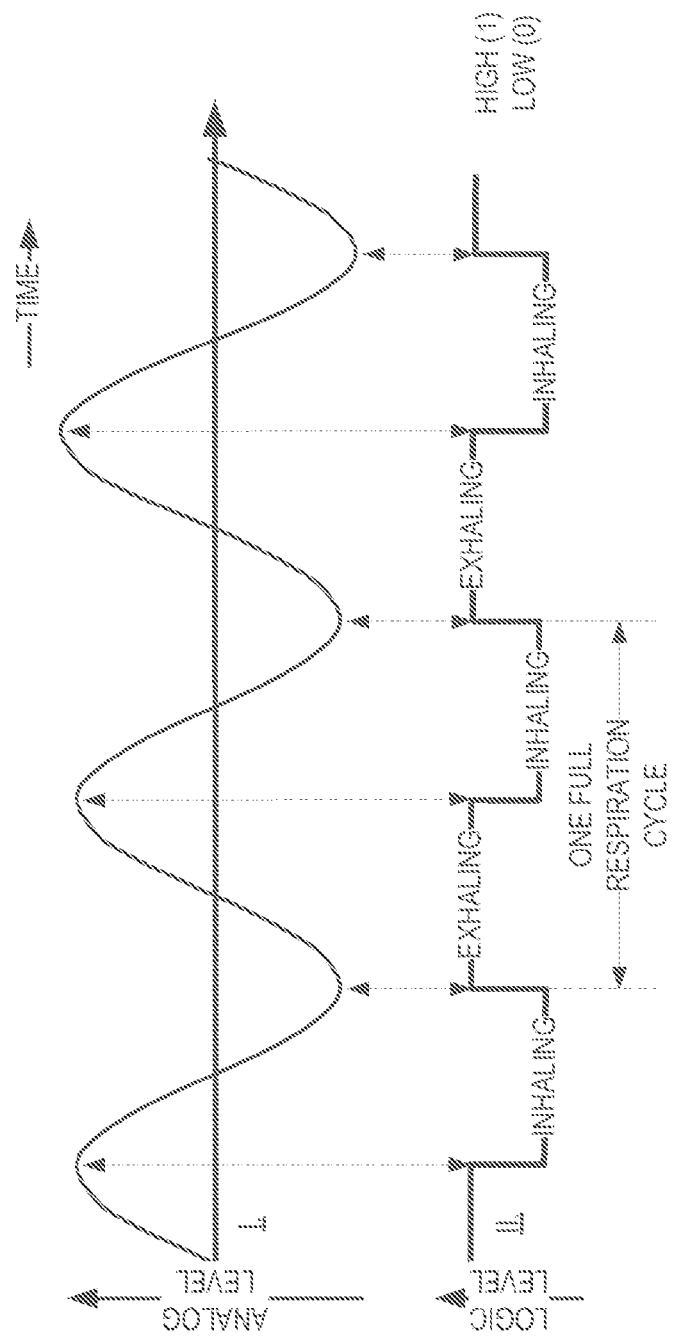
FIG. 3D is an electrical timing diagram of an analog to digital conversion of an airflow sensor signal by an EMI/ESD Hardened Sensor Interface.

Referring to FIG. 3D, there is indicated a timing diagram of the analog to digital conversion function of the EMI/ESD hardened Sensor Interface 10. The top graph indicated by roman numeral I. depicts the analog waveform representation of the respiratory signal coming from the airflow sensor. The bottom graph indicated by Roman numeral II. Depicts the digital representation of the respiratory signal to the Activity Detector. A positive slope of the analog waveform represents inhaling. A negative slope of the analog waveform represents exhaling. The output of the supply filtered analog to digital converter 116 of FIG. 25 changes its output to a low level as soon as the analog waveform of graph I. changes its slope from positive to negative indicating exhaling. The output waveform of the supply filtered analog to digital converter 116 in graph II. changes its output to a high level as soon as the analog waveform of graph I. changes its slope from negative to positive indicating inhaling.

Due to the nature of the device application, through its typical long sensor and transducer wires, exposure of the output to ESD may potentially destroy the transducer driver circuitry. Thus, special ESD countermeasures have to be put in place in order to prevent damage or total destruction of the sensitive, low power circuitry.

The EMI/ESD hardened sensor interface 10 may comprise a multitude of EMI/ESD countermeasures in order to ensure that the sensor signal 3 will be detected, processed and decoded correctly by this invention without suffering from the adverse affects of EMI and ESD. The following is a list of EMC component level countermeasures for the EMI/ESD hardened sensor interface:

The following is a list of EMC component level countermeasures for the EMI/ESD hardened sensor Interface:
1. Feed-through capacitors
2. Instrumentation amplifier
3. Matched gain setting resistor network to maintaining high CMRR
4. Ferrite beads, series EMI suppression element
5. Filter capacitors, parallel EMI suppression element
6. Common mode RF filter, parallel EMI suppression element
7. Common mode RF choke, series EMI suppression element
8. Power supply rail filtering
9. Signal decoupling, parallel EMI suppression element
10. Signal lead filtering, series EMI suppression element
11. Component location
12. PCB routing
13. Close proximity
14. Short and wide traces are better than long and skinny ones
15. Schottky diodes, EMI suppression parallel element
16. Resistors, series EMI suppression element
17. Inductors, series EMI suppression element
18. Cascaded capacitor banks, 0.01 uf and 10 uF
19. Inductors in V+ and V− feeds before capacitor cascade, power feed output For the purpose of EMI/RFI shielding of the EMI/ESD hardened sensor Interface 10, a metal case is mounted on to of the picket fenced PCB circuit boundary with ground pane and ground flooded signal layers.

The use of the following PCB based EMC countermeasures:
1. Power and ground planes
2. Layer flooding
3. Picket fencing
4. Short and narrow signal traces
5. Short and wide power traces The following operational parameters are adjustable
1. Filter response (Butterworth, Bessel, Chebyshev, Elliptic, etc.)
2. High pass cut-off frequency (0.01 Hz to 100.00 Hz)
3. Low pass cut-off frequency (0.01 Hz to 100.00 Hz)
4. Signal Amplifier gain (−70 dB to +40 dB)
5. Signal detection threshold (0.01% to 10%)

EMI/ESD hardening against the aforementioned offenders not only satisfies domestic and international requirements on emissions and susceptibility but also results in robust operation, cleaner internal signals, improved signal to noise ratio (SNR) and greater dynamic range. The sensor interface 10 described herein allows for a stimulation controller to be used with various sensors including those to be developed in the future. Moreover, the sensor interface described allows for a practitioner to view an analog and digital version of a patient signal and further allows for additional analysis and processing of each signal.

A method of using the sensor interface may involve positioning a sensor on a patient and connecting the sensor to the sensor interface. The method may further involve receiving a signal from the sensor positioned on the patient and filtering the signal to remove EMI/RFI interference, further treating the signal to prevent transmission of ESD, filtering out internal interference, amplifying the signal, further filtering the signal to remove signal artifacts resulting from the sensor sensitivity, converting the signal from an analog to a digital signal and outputting either an analog signal, a digital signal, or both.

Activity Detector

An activity detector may receive a previously converted digital signal from a sensor interface as shown in FIGS. 2A and 2B. The received signal may, for example, indicate when a person is inhaling and when they are exhaling. The activity detector may interpret that signal based on certain stored information. For example, the activity detector may be calibrated based on a patient's status as an adult and may define an upper limit of one inhalation/exhalation cycle as being 6 seconds long. By monitoring the incoming digital inhalation/exhalation signal the activity detector may determine if a cycle is abnormal. The activity detector may then notify other elements of a stimulation controller.

There is a need for a device that can monitor a patient for basic indications of a sleep disorder to allow other portions of an apparatus to standby on less than full power unless and until they are needed.

Referring to FIG. 4A, there is indicated more specifically by numeral 20 an Activity Detector. AN ACTIVITY IS NOT LIMITED TO APNEA IT MAY ANY EVENT SUCH AS SNORING, LEG MOVEMENT, LIMB MOVEMENT, JAW MOVEMENT, POTENTIAL SIDS EVENT (BABY NOT BREATHING), ETC. The Activity Detector 20 receives its input via the digital signal 12 from the output of the EMI/ESD hardened sensor Interface 10. The Activity Detector 20 connects via the activity signal 22 to the Stimulus Timer 30. For the purpose of inter-device communication, command and control, the Activity Detector 20 connects to the Device Controller Bus 92. A detailed description of the Activity Detector 20 is provided below and in a separately filed U.S. Provisional Patent Application titled Activity Detector for a closed loop neuromodulator, filed on Aug. 22, 2008, the contents of which are hereby incorporated by reference herein.

The decision of whether a patient is experiencing an apnea or is breathing normally is made in the Activity Detector.

An activity detector 20 is shown receiving a digital airflow signal 12 from an EMI/ESD hardened sensor interface 10. The Activity Detector 20 may transmit an activity signal 22 to a stimulus timer or other elements of a stimulation controller. Additionally, for purposes of inter-device communication, command, and control, the activity detector 20 may also be connected to a device controller bus 92. Also shown in FIG. 4A is a diagram of inhalation and exhalation as it relates to normal and abnormal breathing. It is noted here, that an activity can be any activity relevant to a neurological condition. In many cases, as in the case of sleep apnea, the relevant activity will be breathing activity. For purposes of discussion, a majority of following relates to inhalation and exhalation as it relates to sleep apnea, but those skilled in the art will understand and appreciate that the activity could also be snoring, leg movement, limb movement, jaw movement, or any other activity relevant to a neurological condition or sleep disorder.

The Activity Detector 20 may convert the digital airflow signal 12, or other relevant signal, into a digital activity signal 22. As shown in FIG. 4A, the digital airflow signal 12 is high when the patient is inhaling and is low when the patient is exhaling. In contrast, the digital activity signal 22 is high when the patient is breathing normally and is low when the patient is breathing abnormally. The activity detector 22 may determine the difference between normal and abnormal based on previously set or calibrated standards. For example, the typical breathing range for a sleep patient may be between 10 to 20 breaths per minute reflecting a 3 to 6 second breathing cycle. Thus, the activity detector may be calibrated to indicate abnormal breathing when the patient fails to breath for more than 6 seconds. The available range, however, can be set to any range relevant to the activity being monitored and may even be calibrated to detect continuity of activity rather than absence of activity. For example, leg movement disorders may involve setting the activity detector to trigger the remaining elements of the stimulation controller when the activity continues for a given amount of time.

The Activity Detector 20 converts the digital airflow signal 12 into a digital activity signal 22. The digital airflow signal 12 is high when the patient is inhaling and is low when the patient is exhaling. The digital activity signal 22 is high when the patient is breathing normally and is low when the patient is breathing not normally. The typical breathing range for a sleep patient is between 10 to 20 breaths per minute. The invention goes well above and below this rate to accommodate other events in other CNS disorders.

A purpose of the Activity Detector 20 is to detect obstructive sleep apnea, central sleep apnea, complex sleep apnea, but also snore, snore and apneas, leg movement, limb movement, jaw movement etc.

Figure 4B:
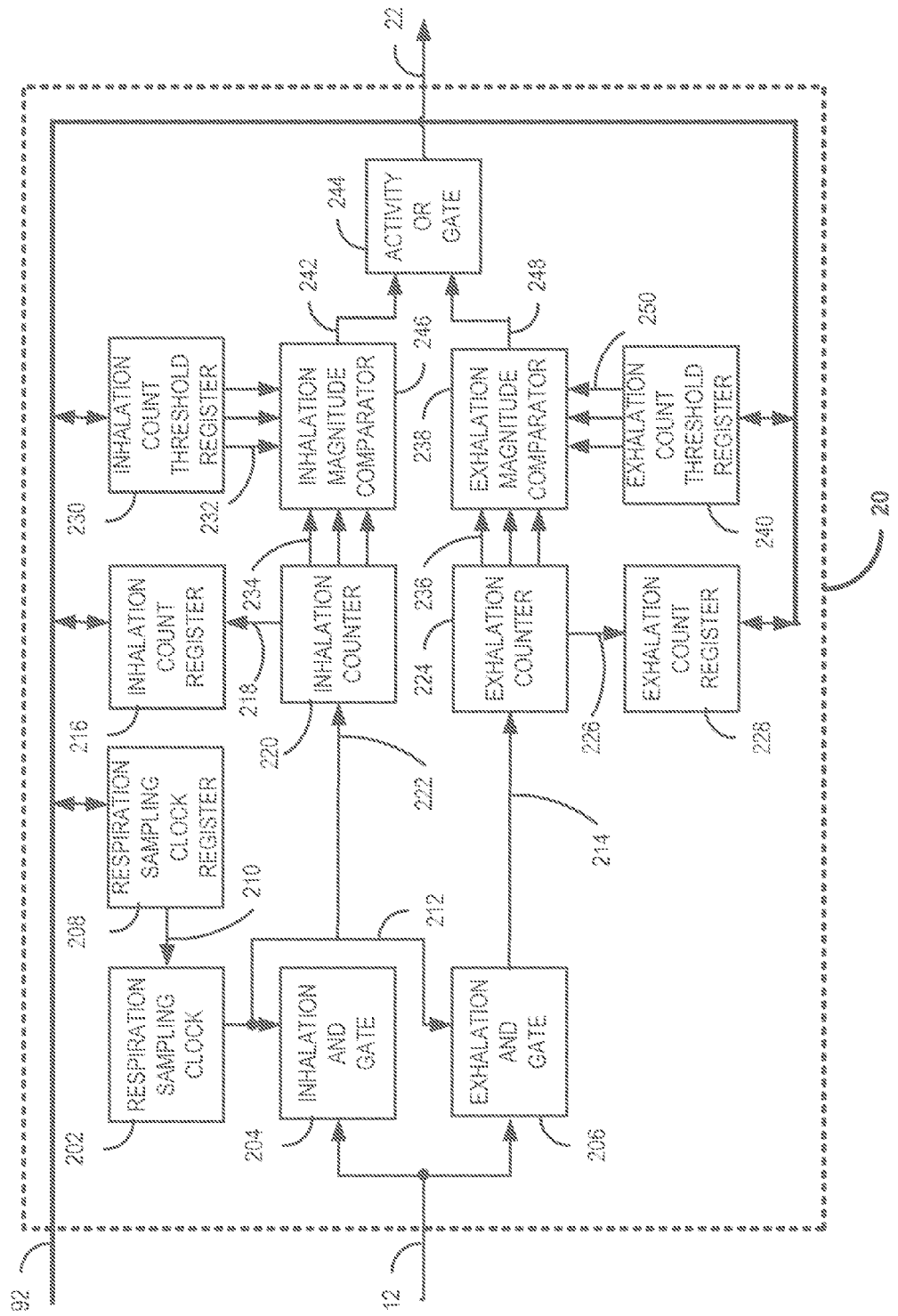
FIG. 4B is a detailed electrical block diagram of an Activity Detector according to one example of the present subject matter.

Referring to FIG. 4B, there is indicated more specifically by numeral 20 a detailed block diagram of the Activity Detector. The activity detector may include several inhalation and exhalation devices including: gates 204, 206, counters 220, 224, registers 216, 228, magnitude comparators 246, 238, and count threshold registers 230, 240. The activity detector may also include a respiration sampling clock and a respiration sampling clock register as well as an activity gate 244.

The inhalation and exhalation gates 204, 206 may continually receive the incoming digital airflow signal 12 and send timed signals to their respective counters 220, 224. For example, when the incoming digital airflow signal 12 is high, reflecting inhalation, the inhalation gate 204 may send a signal to the inhalation counter 220 every millisecond or any other regular time interval. This regular time interval may be referred to as the clock sampling rate and the gates 220, 224 may rely on the respiration sampling clock 202 to trigger them based on this sampling rate. Thus, based on the information the gates 204, 206 receive from the incoming digital airflow signal 12 and the respiration sampling clock 202, the gates 204, 206 may "open" and thus send a triggering signal to their respective counters 220, 224. In turn, each time the inhalation and exhalation counters 220, 224 receive a signal from their respective gate 204, 206, the counters 220, 224 may advance their count.

Signal 12 actually gates the sampling clock and allows a specific amount of clock pulses to reach the counter in order to give a signal count that is relative to the inhalation or exhalation duration. If that count is higher than the threshold then abnormal breathing has been detected.

The respiration-sampling clock 202, responsible for triggering the inhalation and exhalation gates 204, 206 based on the clock sampling rate, may receive this clock sampling rate through an 8-bit parallel load port connection to a respiration sampling clock register 208. The respiration sampling clock register 208 may be interfaced with an internal control bus 92. The register is readable and writable and the clock sampling rate can be stored in the respiration clock register 208 via the control bus 92 and may be adjusted as required for a given condition. The respiration sampling clock 202, may then receive this clock sampling rate from the register 208 and trigger the gates accordingly.

Referring again to the inhalation and exhalation counters 220, 224, a primary 8-bit parallel output 234, 236 of the counters may be connected to the 8-bit input of their respective magnitude comparators 246, 238. The magnitude comparators 246, 238 may constantly compare the actual inhalation or exhalation count to a threshold count. As soon as the actual inhalation or exhalation count of the respective counter is equal to or greater than a respective threshold count, the magnitude comparator may issue a single bit magnitude signal 242, 248 to the activity gate 244.

Similar to the respiration sampling clock, the magnitude comparators 246, 238 rely on a count threshold register 230, 240 interfaced with a control bus 92. The count threshold registers 230, 240 are readable and writable and the threshold value may be stored in the registers via the control bus 92. This value may then be uploaded to the magnitude comparators 246, 238 via the 8-bit parallel connection 234, 236, for comparison with the actual count. For example, if a 6 second breathing cycle is considered normal and anything over 6 is abnormal, the inhalation threshold and exhalation threshold may each be set to approximately 3 seconds in the count threshold registers 230, 240. This value can then be uploaded by the magnitude comparators 246, 238 and compared with the actual count of a patient.

The actual inhalation/exhalation count established by the counters 220, 224 may also be available via a byte wide secondary count parallel output 218, 226 extending to an 8-bit count register 216, 228. As with the respiration sampling clock register, the inhalation and exhalation count registers may be interfaced with an internal control bus 92. As such, the actual 8-bit inhalation or exhalation count may be read via the count registers 216, 228 through the 8-bit internal control bus 92.

Referring back to the activity gate 244, it may provide an activity signal 22 to additional elements of a stimulation controller. The activity signal 22 may be high during normal breathing and low during abnormal breathing. When either the inhalation magnitude comparator 246 or the exhalation magnitude comparator 238 provides a low signal, due to an inhalation or exhalation counter overrun, the activity signal 22 may also provide a low signal, indicating abnormal breathing. It is noted that the activity signal 22 may not reflect an Apnea event because in order for the detected non-breathing event to be qualified as a sleep apnea, the breathing has to secede for a medically established amount of time. Further analysis may be provided within a stimulus timer to determine whether an apnea event has been detected.

A method of providing a normal or abnormal activity signal includes receiving a digital inhalation and exhalation signal, counting the time for each of inhalation and exhalation and comparing the count to a threshold value. The method further includes providing a normal activity signal when the threshold value is not exceeded and providing an abnormal activity signal when the threshold value is exceeded.

Respiration sampling clock range: 0 to 255 ms, 1 ms resolution
  Inhalation count register range: 0 to 255 s, 1 s resolution
  Exhalation count register range: 0 to 255 s, 1 s resolution
  Inhalation count threshold range: 0 to 255 s, 1 s resolution
  Exhalation count threshold range: 0 to 255 s, 1 s resolution An advantage of the present subject matter is that the information it provides allows for the device to make further decisions on how much of the device needs to be activated. For instance, if breathing is continually normal, the device may temporarily shut down other elements to conserve energy. (E.g. shut down generators, timers and gain block when breathing is detected. Activate generators, timers and gain block when no breathing is detected.)

Referring to FIG. 4B, there is indicated more specifically by numeral 20 a detailed block diagram of the Activity Detector. Input connection to the output of the EMI/ESD Hardened Sensor Interface is provided by the digital signal 12. The digital input 12 connects to the first input of the inhalation gate 204 and to the first input of the exhalation gate 206. The respiration-sampling clock 202 connects to the second input of the inhalation gate 204 via connection 212. The respiration-sampling clock 202 also connects to the second input of the exhalation gate via connection 212. The clock-sampling rate of the respiration-sampling clock 202 is being set by the loading of the respiration-sampling clock 202 via its 8-bit parallel load port 210 via the respiration sampling clock register 208. The respiration sampling clock register can be written and read-back via the inhalation count register 216 through the 8-bit internal control bus 92. The output of the inhalation gate 204 provides a gated/timed inhalation clock signal via its output 222 to the input of the inhalation counter 220. The inhalation counter 220 advances its count each time a gated inhalation clock signal triggers it. The actual inhalation count is available via the byte wide secondary inhalation count parallel output 218. An 8-bit inhalation count register 216 is connected to the inhalation count output 218. The actual 8-bit inhalation count can be read via the inhalation count register 216 through the 8-bit internal control bus 92. The primary 8-bit parallel output 234 of the inhalation counter 220 is connected to the 8-bit input of the inhalation magnitude comparator 246. The 8-bit inhalation magnitude comparator 246 constantly compares the actual inhalation count via the 8-bit parallel connection 234 from the inhalation counter 220 with the inhalation threshold count port 232 whose value has been loaded into the inhalation count threshold register 230 via the internal control bus 92. As soon as the actual inhalation count of inhalation counter is equal or greater than the inhalation threshold count that has been loaded into the inhalation count threshold register 230, a single bit magnitude signal 242 is being issued and passed to the two input OR gate 244. The output of the exhalation gate 206 provides a gated/timed exhalation clock signal via its output 214 to the input of the exhalation counter 224. The exhalation counter 224 advances its count each time a gated exhalation clock signal triggers it. The actual exhalation count is available via the byte-wide secondary exhalation count parallel output 226. An 8-bit exhalation count register 228 is connected to the exhalation count output 226. The actual 8-bit exhalation count can be read via the exhalation count register 228 through the 8-bit internal control bus 92. The primary 8-bit parallel output 226 of the exhalation counter 224 is connected to the 8-bit input of the exhalation magnitude comparator 238. The 8-bit exhalation magnitude comparator 238 constantly compares the actual exhalation count via the 8-bit parallel connection 236 from the exhalation counter 224 with the exhalation threshold count port 250 whose value has been loaded into the exhalation count threshold register 240 via the internal control bus 92. As soon as the actual inhalation count of the exhalation counter 224 is equal or greater than the exhalation threshold count that has been loaded into the exhalation count threshold register 240, a single bit magnitude signal 246 is being issued and passed to the two input OR gate 244. The output of the Two Input OR gate 244 is high during normal breathing. As soon as either the inhalation magnitude comparator or the exhalation comparator goes low due to an inhalation or exhalation counter overrun do to a non breathing event, the Activity Signal output 22 of the two input OR gate 244 goes low, indicating abnormal breathing. The activity signal 22 is not an Apnea signal because in order for the detected non-breathing event to be qualified as a sleep apnea, the breathing has to secede for at least a few seconds. The decision whether an apnea event has been detected is made within the Stimulus Timer 30.

Figure 4C:
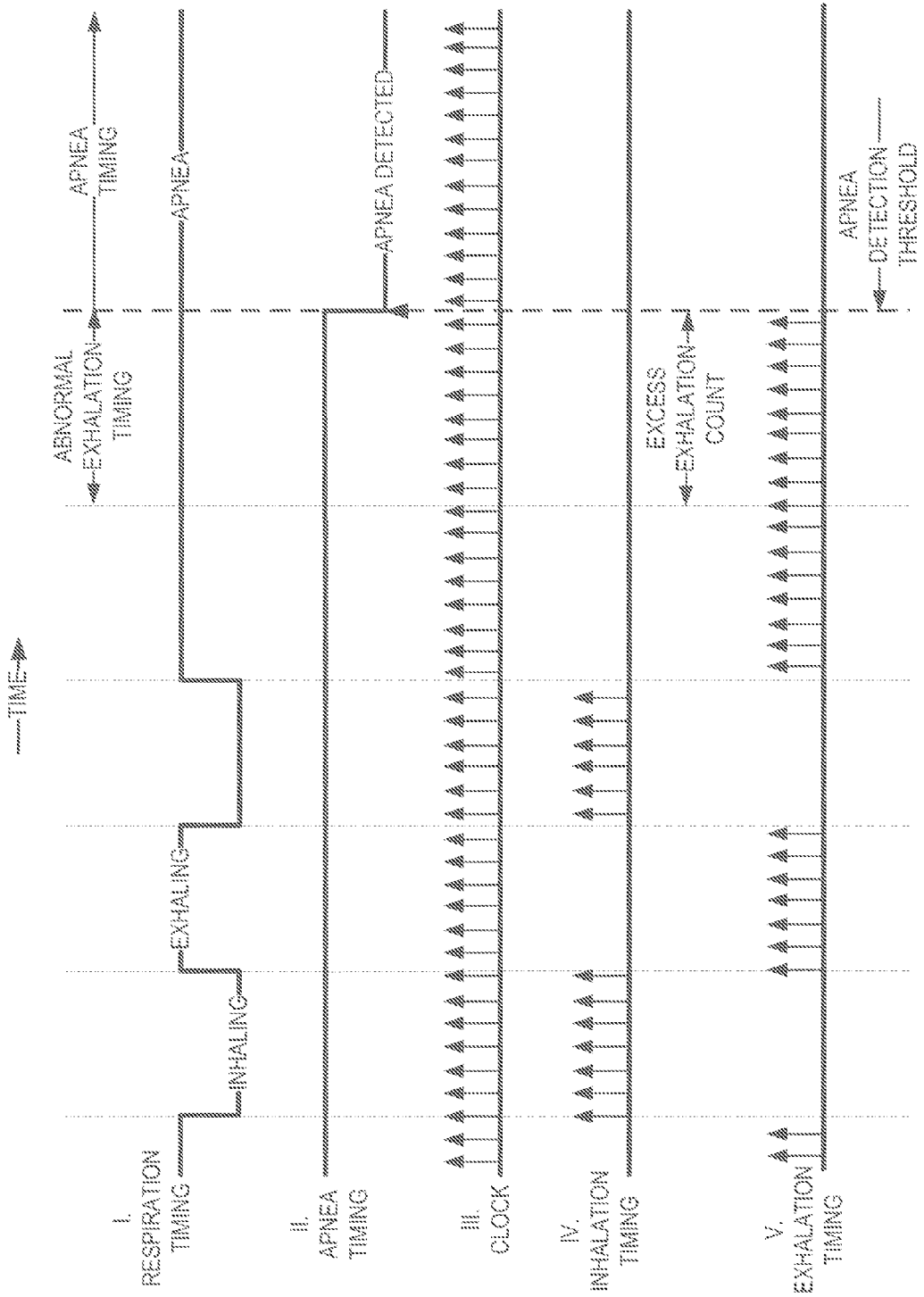
FIG. 4C is a timing diagram of an apnea detection of an Activity Detector according to one example of the present subject matter.

FIG. 4C is a timing diagram of an apnea detection of an Activity Detector according to one example of the present subject matter.

In one embodiment, an activity detector is provided including a respiration sampling clock, at least one gate, at least one counter, at least one magnitude comparator, and an activity gate. In this embodiment, the respiration sampling clock is configured to provide a clock sampling rate to the at least one gate. The at least one gate is configured to receive a digital inhalation and exhalation signal and trigger the at least one counter based on the clock sampling rate. The at least one magnitude comparator is configured to compare a count provided by the at least one counter to a threshold count and signal the activity gate, when the threshold count is exceeded. In this embodiment, the activity gate is configured to provide an activity signal indicating normal or abnormal breathing.

In another embodiment, the at least one gate includes an inhalation gate and an exhalation gate. In another embodiment, the at least one counter includes an inhalation counter and an exhalation counter. In another embodiment, the at least one magnitude comparator includes an inhalation magnitude comparator and an exhalation magnitude comparator. In yet another embodiment, each of the respiration sampling clock, the at least one gate, the at least one counter, and the at least one magnitude comparator each have an associated register for communication with a control bus.

In another embodiment, a method of providing a normal or abnormal activity signal includes receiving a digital inhalation and exhalation signal, counting the time for each of inhalation and exhalation and comparing each count to a separate threshold value. The method further includes providing a normal activity signal when the threshold value is not exceeded and providing an abnormal activity signal when the threshold value is exceeded.

Stimulus Timer

A stimulus timer may receive a previously converted digital signal from an activity detector as shown in FIGS. 2A and 2B. As shown in FIG. 3, the received signal may, for example, indicate when a person is breathing abnormally. The stimulus timer may further analyze the signal to determine if any abnormal activity constitutes a manifestation of a sleep disorder. For example, the stimulus timer may be set to trigger additional elements of a closed loop neuromodulator when a person fails to breath for more than 20 seconds. Thus, by monitoring the incoming digital activity signal the stimulus timer may determine if the abnormal breathing constitutes sleep apnea and may notify other elements of a stimulation controller accordingly. The stimulus timer may provide a stimulus start signal, a stimulus rate signal, and a stimulus duration signal.

Referring to FIG. 5A, a stimulus timer 30 is shown receiving an incoming activity signal 22 from an activity detector 20. The stimulus timer 30 may transmit a stimulus start signal 32, a stimulus rate signal 34, and stimulus duration signal 36 to a stimulus sequencer 40 or other elements of a stimulation controller. Additionally, for purposes of inter-device communication, command, and control, the stimulus timer 30 may also be connected to a device controller bus 92.

Referring to FIG. 5A, there is indicated more specifically by numeral 30 a stimulus timer. The stimulus timer 30 receives its input via the activity signal 22 from the Activity Detector 20. The stimulus timer 30 connects via the stimuli start signal 32, stimuli rate signal 34 and the stimuli duration signal 36 to the stimulus sequencer 40. For the purpose of inter-device communication command and control, the Stimulus Timer 30 connects to the common Device Controller Bus 92. A detailed description of the stimulus timer 30 is provided below and in a separately filed U.S. Provisional Patent Application titled Stimulus Timer for a closed loop neuromodulator, filed on Aug. 22, 2008, the contents of which are hereby incorporated by reference herein.

The Stimulus Timer is responsible for diagnostic and therapy related closed loop neuromodulator functions.

A purpose of the Stimulus Timer 30 is to process the activity signal 22 from the Activity Detector 20 and derive specific timing information from it that is crucial to the operation of the closed loop neuromodulator such as therapy delay, apnea detection, apnea duration measurement, apnea counts, stimulus delay, stimulus rate and stimulus duration timing.

In addition, the Stimulus Timer 30 enables, a low power design, which is crucial for battery operation. A genera power down signal that will be issued to all functional but non essential elements can be issued by the device controller by polling the apnea duration register. The general power down signal will keep other functional modules and functional blocks of the design inactive until their function and operation are needed, milliseconds after an apnea has been detected. Low power operation shuts down functional blocks when not needed for immediate operation. E.g. shut down generators, timers and gain block when breathing is detected. Activate generators, timers and gain block when no apnea has been detected.

The timing of issuing stimuli and sending them to the patient continues until the resumption of breathing has been detected.

Figure 5B:
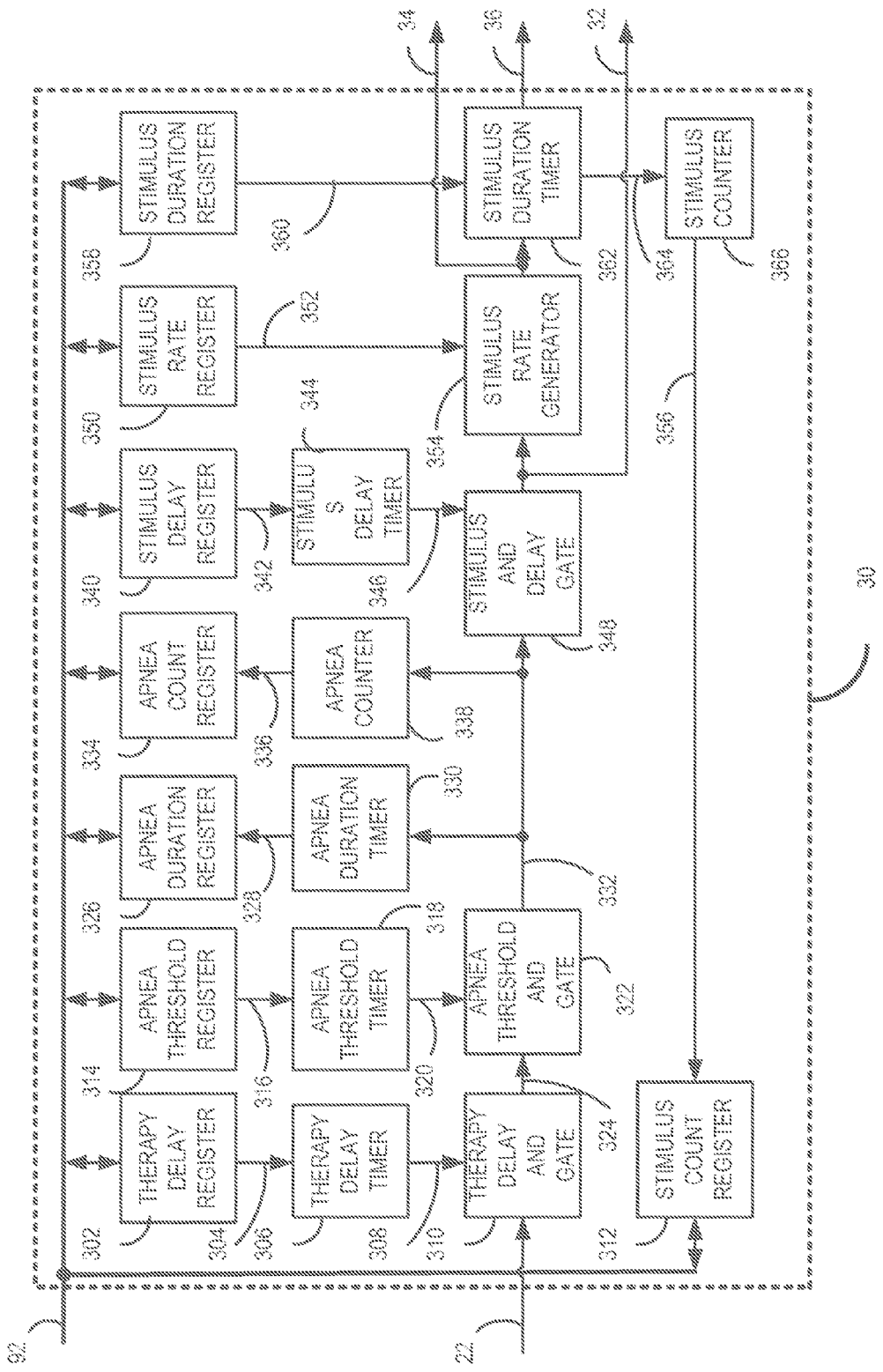
FIG. 5B is a detailed electrical block diagram of a Stimulus Timer according to one example of the present subject matter.

Referring to FIG. 5B, a detailed block diagram of the stimulus timer 30 is provided. The stimulus timer 30 may include several therapy delay elements including a gate 310, timer 306, and register 302. The stimulus timer 30 may also include several apnea threshold elements including a gate 322, timer 318, and register 314. Additional apnea related devices include an apnea duration timer 330 and an apnea duration register 326 as well as an apnea counter 338 and an apnea count register 334. It is noted here, that the neurological condition or sleep disorder is not limited to sleep apnea, but that reference is made to sleep apnea for purposes of description. Those skilled in the art will understand and appreciate that the sleep disorder could also be snoring, bruxism, or any other neurological condition or sleep disorder. Several stimuli related elements may also be included. A stimulus delay gate 348, timer 344, and register 340 may be provided as well as a stimulus rate generator 354 and register 350. Additional stimulus related elements may include a stimulus duration timer 362 and register 358 as well as a stimulus counter 366 and stimulus count register 312.

As previously discussed, the stimulus timer 30 may receive an activity signal 22 from an activity detector 20. The activity signal 22 may be directed into a first input of a therapy delay gate 310. Together with the therapy delay timer 306 and therapy delay register 302, the therapy delay gate 310 may allow a stimulation controller to be set not to provide any stimulus for a given period of time. For example, if it is desired to allow a patient to achieve a certain sleep state or simply get into a reasonably deep sleep prior to stimulating them, the therapy delay system can be set to block stimulation until a certain time has passed. As such, the therapy delay register 302, which is both writable and readable through the 8-bit internal control bus 92, allows for a delay to be stored in the therapy delay register 302. The therapy delay timer 306 receives its therapy delay time value through the 8-bit parallel connection 304 to the Therapy delay register 302 and, in turn, may signal the therapy delay gate 310 to open once the time has elapsed.

Once the therapy delay time has elapsed, the therapy delay gate 310 allows the activity signal to pass through to the apnea threshold gate 322 via connection 324. The apnea threshold gate 322 in conjunction with the apnea threshold timer 318 and apnea threshold register 314 qualifies whether the patient experiences an apnea or not. That is, the length of time defining sleep apnea (e.g. 20 seconds), or any other condition, can be stored in the apnea threshold register 314, which can be written to and read-back through the 8-bit internal control bus 92. The apnea threshold timer 318 receives its apnea threshold value through the 8-bit parallel connection 316 to the apnea threshold register 314 and, in turn, may signal the apnea threshold gate 322 to open once the apnea threshold has been exceeded. That is, when the activity signal has remained low for longer than the apnea threshold, the apnea threshold gate 322 will open.

The apnea threshold gate 322 connects to the stimulus delay gate 348 via connection 324. Along its path to the stimulus delay gate 348, the connection 324 also connects to the apnea duration timer 330 and the apnea counter 338. The apnea duration timer 330 may measure the apnea duration indicated by a low level of Therapy delay gate output 324. The apnea counter may count individual apneas as indicated by the output of the apnea threshold gate 322. These elements are intended for collecting data for export via the internal control bus 92. Thus, these elements are further connected via 8-bit parallel connections to associated registers 326 and 334. The apnea duration register 326 and apnea count register 334 are, in turn, connected via an 8-bit connection to the internal control bus 92. As with other registers disclosed herein, these registers 326, 324 are readable and writable so as to be able to store the values associated with the apnea duration timer and apnea counter for later reading by another device.

Beyond the apnea duration timer 330 and the apnea counter 338, the connection 324 proceeds to the stimulus delay gate 348. The stimulus delay gate 348 delays the start of any CNS stimulus until the set Stimulus Delay Time has expired. This stimulus delay may allow for an additional level of control over the timing of the stimulus. That is, the stimulus may be delayed due to the therapy delay. It may also be delayed beyond a determination of abnormal breathing to wait for a determination of whether an apnea has occurred. While the stimulus delay may be set to zero, it may also be set to some positive value providing some level of control over the timing of the stimulus relative to a determination of apnea. Thus, the stimulus may not be delivered immediately once an apnea has been determined. Similar to the previously discussed register, timer, and gate combinations, a stimulus delay register 340 may be provided to store the stimulus delay time. The stimulus delay register 340 may be both readable and writable via an 8 bit internal control bus 92. The stimulus delay timer may receive the stimulus delay time through the 8-bit parallel connection 342 from the stimulus delay register 340. The stimulus delay timer 344 connects to the stimulus delay gate 348 and may allow the stimulus delay gate 348 to open once the stimulus delay time has elapsed.

The stimulus delay gate 348 connects to the stimulus rate generator 354 via connection 32. Connection 32 represents the stimulus start signal. If the therapy delay time has elapsed and the apnea threshold time has been exceeded and the stimulus delay time has elapsed, a stimulus start signal may be released from the stimulus delay gate 348 through connection 32.

This stimulus start signal may be directed out of the stimulus timer, but also is directed to the stimulus rate generator 354 for further processing. The stimulus rate generator 354 generates the stimulation rate at which the CNS stimuli are sent to the transducer/patient. That is, where successive stimuli are being used to treat a patient, the stimulus rate generator 354 defines the time from the start of one stimulus to the start of the next stimulus. The stimulus rate generator 354 may receive its input directly from the stimulus rate register 350 through the 8-bit parallel connection 352. As with other registers, the stimulus rate register 350 is responsible for storing the stimulus rate. The stimulus rate register 350 may be both writable and readable through the 8-bit internal control bus 92.

The stimulus rate generator 354 connects to the stimulus duration timer 362 via connection 34. Connection 34 represents the stimulus rate signal. This stimulus rate signal may be directed out of the stimulus timer 30, but may also be directed to a stimulus duration timer 362 for further processing. The stimulus duration timer 362 may define the time over which the CNS stimuli are sent to the transducer/patient. That is, where single or multiple stimuli are being used to treat a patient, the stimulus duration timer defines the continuous length of each individual pulse. Like the stimulus rate generator/register combination, the stimulus duration timer 362 receives its duration time value through the 8-bit parallel connection 360 to the stimulus duration register 358. The stimulus duration register 358 can be written to and read-back through the 8-bit internal control bus 92. The output of the stimulus duration timer 362 is the stimulus duration signal 36.

The timing of issuing stimuli and sending them to the patient may be continued until the resumption of breathing has been detected. As this process continues, the stimulus counter 366 may keep track of the number of stimuli being issued. The stimulus counter 366, may in turn store this value in the readable and writable stimulus count register 312, making this value available to the rest of the system through 8-bit internal control bus 92.

A method may be performed involving receiving an activity signal from an activity detector, intercepting the activity signal with a therapy delay gate until the therapy delay has lapsed after which the signal passes to a apnea threshold gate. The apnea threshold gate intercepts the activity signal until an apnea threshold has been exceeded after which the signal passes to the stimulus delay gate. The stimulus delay gate intercepts the signal until a stimulus delay has lapsed after which the signal is issued from the stimulus timer as a stimulus start signal. A stimulus rate generator may issue a stimulus rate signal and a stimulus duration timer may issue a stimulus duration signal.

Therapy delay range: 0 to 255 min, 1 min resolution
Apnea threshold range: 0 to 255 s, 1 s resolution
Apnea duration range: 0 to 255 s, 1 s resolution
Apnea counter range: 0 to 255 apneas
Stimulus delay range: 0 to 25.5 s, 100 ms resolution
Stimuli rate generator range: 0 to 25.5 seconds, 100 ms resolution
Stimuli duration timer range: 0 to 2.55 seconds, 10 ms resolution Referring to FIG. 5B, there is indicated more specifically by numeral 30 a detailed block diagram of the stimulus timer. The input of the Stimulus Timer 30 connects to the output of the Activity Detector 20 via the activity signal 22. The activity signal 22 connects to the first input of the therapy delay gate 310. The Therapy Delay Gate 310 delays any stimulation activity until the set Therapy Delay Time has been expired. The Therapy Delay Gate 310 connects to the Apnea Threshold Gate 324 via connection 324. The therapy delay timer 306 connects to the second input of the therapy delay gate 310 via the connection 308. The therapy delay timer 306 receives its therapy delay time value from through the 8-bit parallel connection 304 from the Therapy delay register 302. The therapy delay register 302 can be written and read-back through the 8-bit internal control bus 92. The Apnea Threshold Gate 322 in conjunction with the Apnea Threshold Timer 318 qualifies whether the patient experiences an Apnea or not. The apnea threshold gate 322 connects to the Stimulus Delay Gate 348 via connection 324. The Apnea threshold timer 318 connects to the second input of the Apnea Threshold Gate 322 via the connection 320. The Apnea threshold timer 318 receives its apnea threshold value through the 8-bit parallel connection 316 from the apnea Threshold Register 314. The apnea threshold Register 314 can be written and read-back through the 8-bit internal control bus 92. The Apnea duration timer 330 measures the apnea duration indicated by a low level of Therapy delay gate output 324. The Apnea duration timer 330 connects to the output 332 of the apnea threshold Gate 322. The value of the Apnea duration timer 330 can be read through the 8-bit parallel connection 328 from the apnea duration Register 326. The apnea duration Register 326 can be read through the 8-bit internal control bus 92. The Apnea counter 338 counts individual apneas as indicated by the output of the apnea threshold gate 322. The value of the Apnea counter 338 can be read through the 8-bit parallel connection 336 from the apnea count Register 334. The apnea count register 334 can be read through the 8-bit internal control bus 92. The stimulus delay gate 348 delays the start of any stimulus until the set Stimulus Delay Time has been expired. The stimulus delay Gate 348 connects to the clock input of the stimulus rate generator 354 via connection 32. The stimulus delay timer 344 connects to the second input of the stimulus delay gate 348 via the connection 346. The stimulus delay timer 344 receives its stimulus delay time value through the 8-bit parallel connection 342 from the stimulus delay register 340. The stimulus delay register 340 can be written and read-back through the 8-bit internal control bus 92. The stimulus delay gate 348 connects to the stimulus rate generator 354 via connection 32. Connection 32 represents the stimulus start signal. The stimulus rate generator 354 generates the stimulation rate at which the stimuli are sent to the transducer/patient. The stimulus rate generator 354 connects to the clock input of the stimulus rate generator 354 via connection 32. The stimulus rate generator 354 receives its stimulus rate value through the 8-bit parallel connection 352 from the stimulus rate register 350. The stimulus rate register 350 can be written and read-back through the 8-bit internal control bus 92. The stimulus rate generator 354 connects to the stimulus duration timer 362 via connection 34. Connection 34 represents the stimulus rate signal. The stimulus duration timer 362 times the stimulation duration at which the stimuli are sent to the transducer/patient. The input of the stimulus duration timer 362 connects to the output of the stimulus rate generator 354 via connection 34. The stimulus duration timer 362 receives its duration time value through the 8-bit parallel connection 360 from the stimulus duration register 358. The stimulus duration register 358 can be written and read-back through the 8-bit internal control bus 92. The output of the stimulus duration timer 362 is the stimulus duration signal 36. Stimulus duration 36 represents the duration at which the patient/transducer is subjected to the current single stimulus.

The single stimulus energy is contained under the area of the individual stimuli pulse shape over time. In order to increase the stimulus energy either the level of the stimulus must be increased or the duration of the stimulus must be increased. The energy provided by any given pulse of stimulation may be determined by defining the area of the individual stimuli pulse shape over time. That is, energy equals power times time (E=P*t) where P represents the power of a stimulus pulse and t represents the duration of stimulus pulse. In order to increase the stimulus energy either the level of the stimulus can be increased or the duration of the stimulus can be increased. Where sleep practitioners are attempting to stifle a sleep disorder and yet avoid arousing a patient, the ability to adjust each of these is advantageous. The stimulus timer disclosed herein allows for adjustment for the duration of element of this energy approach.

The stimulus timer disclosed herein is advantageous because it allows for precise dosing of patients. First, once an apnea or other neurological condition is detected, the initial dose can be introduced at a specific predetermined time. Second, a series of pulses of stimulation may be provided and the stimulus timer allows those pulses to be adjusted relative to one another in time. Third, the stimulus timer further allows for each pulse to be shortened or lengthened.

Additionally, the Stimulus Timer 30 enables, a low power design, which may be beneficial under battery operation. When used in a closed loop neuromodulator such as that shown in FIG. 2A or 2B, a general power down signal may be issued to all functional but non essential elements by the device controller, which may poll the apnea duration register to determine if an apnea is occurring. The general power down signal may keep other functional modules and functional blocks of the device inactive until their function and operation are needed, milliseconds after an apnea has been-detected. Low power operation may allow for shutting down functional blocks when not needed for immediate operation. E.g. shutting down generators, timers and gain blocks when breathing is detected. Activate generators, timers and gain block when an apnea has been detected.

In one embodiment, a stimulus timer for a closed loop neuromodulator includes a therapy delay gate, an apnea threshold gate, a stimulus delay gate, a stimulus rate generator, and a stimulus duration timer, wherein the stimulus delay gate issues a stimulus start signal, the stimulus rate generator issues a stimulus rate signal, and the stimulus duration timer issues a stimulus duration signal.

In another embodiment, the stimulus timer also includes an apnea duration timer. In another embodiment, an apnea counter is also included. In yet another embodiment, the therapy delay gate, apnea threshold gate, and stimulus delay gate each have an associated timer and register, where the associated registers are in communication with an internal control bus. In still another embodiment, a stimulus counter is also included.

A method may be performed involving receiving an activity signal from an activity detector, intercepting the activity signal with a therapy delay gate until the therapy delay has lapsed after which the signal passes to a apnea threshold gate. The apnea threshold gate intercepts the activity signal until an apnea threshold has been exceeded after which the signal passes to the stimulus delay gate. The stimulus delay gate intercepts the signal until a stimulus delay has lapsed after which the signal is issued from the stimulus timer as a stimulus start signal. A stimulus rate generator may issue a stimulus rate signal and a stimulus duration timer may issue a stimulus duration signal.

Stimulus Sequencer

A stimulus sequencer may receive a stimulus start signal, a stimulus rate signal, and a stimulus duration signal from a stimulus timer as shown in FIGS. 2A and 2B. The stimulus sequencer may then determine which stimulus wave shapes to be applied and in what order. For example, the stimulus sequencer may select a combination of stimuli including a tone, a click, and a pop may then provide the order in which these stimuli are used to stimulate a patient. The stimulus sequencer may then transmit a generator select signal to a stimulus generator or other components of a stimulation controller.

Figure 6A:
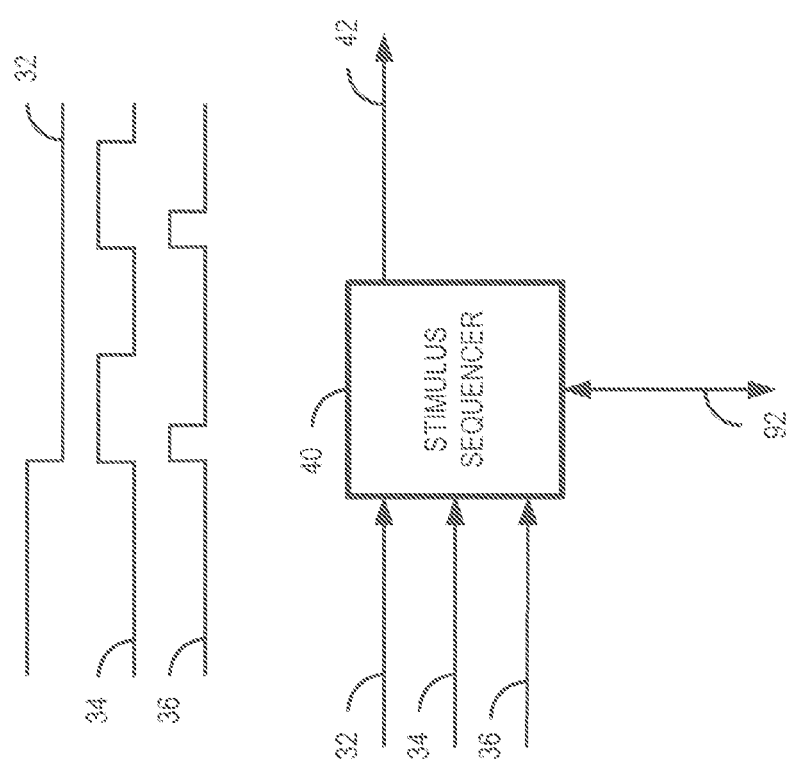
FIG. 6A illustrates generally an electrical block diagram of a Stimulus Sequencer.

Referring to FIG. 6A, there is indicated more specifically by numeral 40 a stimulus sequencer. The stimulus sequencer 40 receives its inputs via the stimuli start signal 32, stimuli rate signal 34 and stimuli duration signal 36 from the stimulus timer 30. The stimulus sequencer 40 connects via the generator select signal 42 to the stimulus generator. For the purpose of inter-device communication command and control, the Stimulus Sequencer 40 connects to the common Device Controller Bus 92. A detailed description of the stimulus sequencer 40 is provided below and in a separately filed U.S. Provisional Patent Application titled Stimulus Sequencer for a closed loop neuromodulator, filed on Aug. 22, 2008, the contents of which are hereby incorporated by reference herein.

A function of the stimulus sequencer is to provide anti-habituation therapy to avoid habituation to stimuli types in patients. In order to avoid habituation to certain stimuli types a multitude of different stimuli types have to be generated and activated as needed in very specific and deliberate sequences. The sequencer activates a very specific stimulus generator as needed and as prescribed. The sleep practitioner can input the stimulation sequence into the device for diagnosis and therapy.

There is a need for fixed operation/manual mode so that the sleep lab practitioner can operate the unit in manual mode for the purpose of experimenting, diagnosing and prescribing the optimum range for specific sleep patient's stimuli type regimen.

Figure 6B:
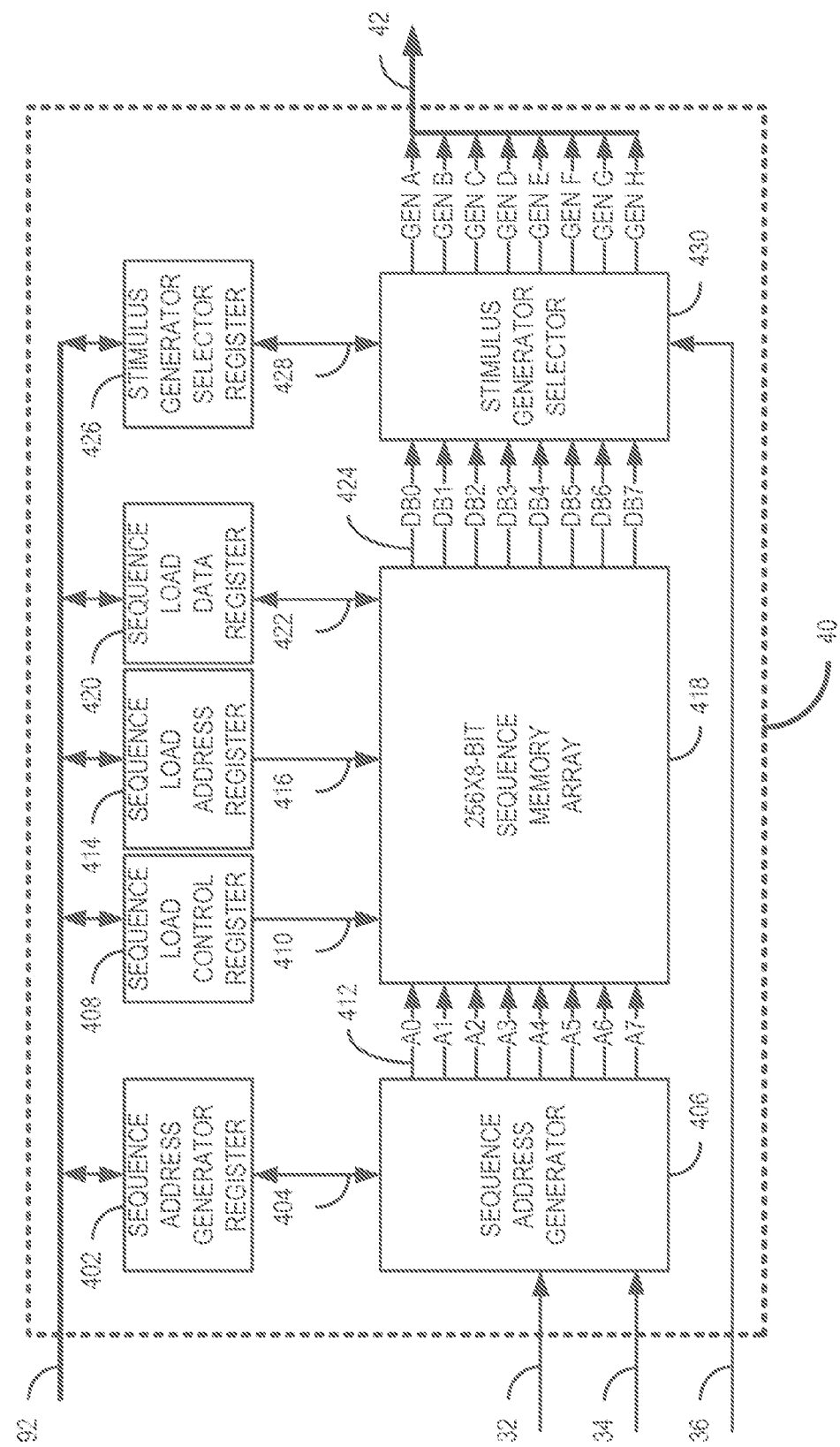
FIG. 6B is a detailed electrical block diagram of a Stimulus Sequencer according to one example of the present subject matter.

Referring to FIG. 6B, the stimulus sequencer may include a sequence address generator 406, a sequence memory array 418, and a stimulus generator selector 430. The stimulus address generator 406 may be in communication with an internal control bus 92, through a stimulus address generator register 402. The stimulus memory array 418, may be in communication with an internal control bus 92 through a sequence load control register 408, a sequence load address register 414, and a sequence load data register 420. The stimulus generator selector 430 may be in communication with an internal control bus 92 through a stimulus generator selector register 426.

The stimulus sequencer decides on which stimulus wave shape is to be applied and in what order. The orders can be but are not limited to:
1. Fixed
2. Sequential
3. Circular
4. Random
5. Periodic
6. Custom
7. Patterned
8. Continuous Fixed means that the same stimulus types are repeatedly applied every time a stimulus is being issued Sequential means that the stimulus types may be changed from stimulus to stimulus during the same apnea, but that the same stimulus sequence starts over the next time an Apnea is detected.

Circular means that the stimulus types may change from stimulus to stimulus during the same apnea, but when a new apnea occurs and the next stimulus is being issued, it will be the next stimulus in the circular sequence. The stimulus types are lined up in a circle. The circle has no specific start or end points.

Random means that the stimulus types are issued in an arbitrary sequence. The stimulus sequence can be generated by a quasi random signal source (QRSS) and subsequently recorded and loaded into the sequence memory array.

Periodic means that the stimulus types are issued in a sequence that is like going up a ladder and then coming down, then going back up and so forth.

Custom means that the stimulus types are issued in a long pre-defined sequence as prescribed by the sleep practitioner.

Patterned means that the stimulus types are issued in short defined sequences as prescribed by the sleep practitioner.

Continuous means that the stimulus type is continuously issued to the transducer/patient with the defined stimulus rate and stimulus duration whether an apnea is present or not. This test mode allows the sleep practitioner to listen, experience and measure the selected stimulus at will.

An element of the stimulus sequencer is its sequence memory array which is loaded with the sequence as selected and described above either on start-up or during operation by the device controller who manages and keeps track of the stimulus sequencing.

The sequence memory array is of a 256×8-bit <00Hex to <FFHex> read writable random access memory (RAM) type. The sequence memory array can be any size memory and is not limited to 256×8-bit.

The sleep practitioner may load the stimuli sequences as needed via remote terminal instructions into the sequence memory array.

All load, control, address and data values are being communicated from the device controller through the internal control bus via the individual registers.

The device controller communicates the sequence information of which is the current generator being selected, which is the next generator a sequence and which was the last generator selected in a sequence.

Sequence address generator range: 0 to 255 addresses
Sequence load control range: 8-bit (clear, set, reset, clock)
Sequence load address range: 8-bit (A0 . . . A7)
Sequence date load range: 8-bit (DB0 . . . DB7)
Device controller keeps track of the following: sequence start points and sequence end points.

Upon receipt of the stimulus start signal, the 8-bit or N-bit programmable sequence generator/counter selects the next stimulus sequence upon receipt of the stimulus rate signal for generating the sequence of the appropriate stimulus generator. With each new stimulus duration signal clocked into the sequence address generator, a new address is being generated and input into the sequence memory array for selection of the particular stimulus type for that specific stimulus.

Referring to FIG. 6B, there is indicated more specifically by numeral 40 a detailed block diagram of the stimulus sequencer. The input of the stimulus sequencers 40 are the stimulus start signal 32, stimulus rate signal 34 and the stimulus duration signal 36. The stimulus start signal 32 connects to sequence address generator 406 internally gated enable port. The stimulus rate signal 34 connects to the sequence address generator 406 clock input port. The stimulus duration signal 36 connects to the stimulus generator selector gated enable port. The sequence address generator 406 connects to the sequence memory array 418 via the address selection bus 412. The sequence address generator 406 receives its programmable count parameters through the 8-bit parallel connection 404 from the sequence address generator 402. The sequence address generator register 402 can be written and read-back through the 8-bit internal control bus 92. The sequence memory array 418 connects to the stimulus generator selector 430 via the stimulus sequence data bus 424. The sequence memory array 418 receives its sequence load control commands through the 8-bit parallel connection 410 from the sequence load control register 408. The sequence load control register 408 can be written and read-back through the 8-bit internal control bus 92. The sequence memory array 418 receives its sequence address load commands through the 8-bit parallel connection 416 from the sequence load address register 414. The sequence load address register 414 can be written and read-back through the 8-bit internal control bus 92. The sequence memory array 418 receives its sequence data load commands through the 8-bit parallel connection 422 from the sequence load data register 420. The sequence load data register 420 can be written and read-back through the 8-bit internal control bus 92. The stimulus generator selector 430 receives its stimulus generator commands through the 8-bit parallel connection 428 from the stimulus generator selector register 426. The stimulus generator selector register 426 can be written and read-back through the 8-bit internal control bus 92. The stimulus generator selector 430 connects to the stimulus generator via the 8-bit stimulus generator data bus 42.

Figure 6C:
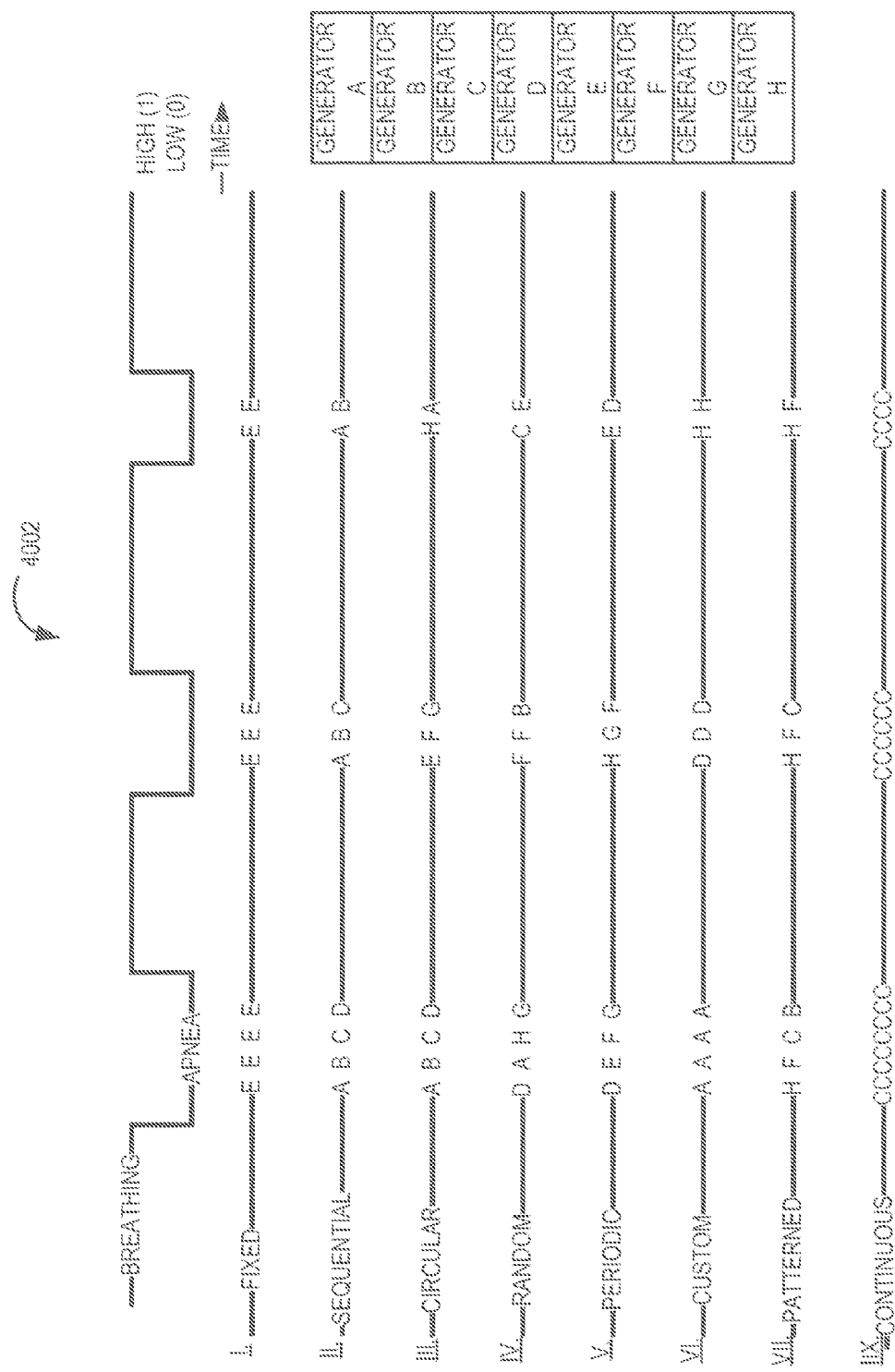
FIG. 6C is timing diagram of various Stimulus generator sequences of a Stimulus Sequencer according to one example of the present subject matter.

Referring to FIG. 6C, there is indicated more specifically by numeral 4002 a detailed stimulus sequence timing diagram for the various types of aforementioned stimulus.

The stimulus sequencer disclosed herein may help to avoid habituation to stimuli types in patients. In order to avoid habituation to certain stimuli types a multitude of different stimuli types may be generated and activated as needed in very specific and deliberate sequences. The sequencer activates a very specific stimulus generator as needed and as prescribed. The sleep practitioner can input the stimulation sequence into the device for diagnosis and therapy.

The sequencer may be capable of a fixed operation/manual mode so that the sleep lab practitioner can operate the unit in manual mode for the purpose of experimenting, diagnosing and prescribing the optimum range for specific sleep patient's stimuli type regimen.

Stimulus Generator

A stimulus generator may receive a generator select signal from a stimulus sequencer as shown in FIGS. 2A and 2B. The generator select signal may contain a sequence of stimulus types in a specific order and may also define the duration of each stimulus. The stimulus generator may include individual generators for each stimulus type available such as one generator for generating a hiss signal, another generator for generating a click signal, and additional types as discussed below. The stimulus generator processes the generator select signal by signaling the individual generators defined by the generator select signal to generate a stimulus signal for the duration also defined by the generator select signal. The stimulus generator may then emit a stimulus signal to a stimulus escalator or other portions of a stimulation controller.

Referring to FIG. 7A, there is indicated more specifically by numeral 50 a stimulus generator. The stimulus generator 50 receives its inputs via the stimuli select signal 42, from the stimulus sequencer 40. The stimulus generator 50 connects via the stimuli signal 52 to the stimulus escalator 60. For the purpose of inter-device communication command and control, the Stimulus Generator 50 connects to the common Device Controller Bus 92. A detailed description of the stimulus generator 50 is provided below and in a separately filed U.S. Provisional Patent Application titled Stimulus Generator for a closed loop neuromodulator, filed on Aug. 22, 2008, the contents of which are hereby incorporated by reference herein.

A function of the stimulus generator is to provide different types of stimuli in order to avoid habituation to stimuli signal in patients. In order to avoid habituation to certain stimuli types a multitude of different stimuli types have to be generated and activated as needed. The sleep practitioner can input the stimulation sequence into the device for diagnosis and therapy.

There is a need for fixed operation/manual mode so that the sleep lab practitioner can operate the unit in manual mode for the purpose of experimenting, diagnosing and prescribing the optimum range for specific sleep patient's stimuli regimen.

The stimulus generator delivers the stimulus type according either what the sleep practitioner has prescribed or what the auto-adjusting routine has determined to be the optimal stimulus type for the particular patient. The stimulus types can be but either single or a combination thereof, but is not limited to:

1. Tone
2. Click
3. Pop
4. Noise
5. Hiss
6. Modulated
7. Siren
8. Warble
9. Custom Tone means that the stimulus type is harmonic in nature such as sinusoidal, square, trapezoidal, triangular, saw tooth, etc type signal waveforms. A tone may sound similar to a tone played on an instrument.

Click means that the stimulus type is a single, abrupt and sharp waveform transition generating a wide frequency spectrum. A click may sound similar to a single sharp hand clap or door slamming shut.

Pop means that the stimulus type is a single but less sharp waveform transition generating a narrow frequency spectrum. A pop may sound similar to a bottle of Champaign being opened or a thunderclap from a single but distant lightning strike.

Noise means that the stimulus type is constant and consists of all frequency components in the relevant frequency band of interest. White noise for example has a very evenly distributed frequency spectrum and its power distribution is constant over a wide frequency range. Pink noise for example has a constant power density in a given octave frequency ratio of F2/F1=2, were F2 is the higher frequency and F1 is the lower frequency. White noise sounds rather sharp whereas pink noise sounds rather mellow. A noise signal may sound similar to a TV or Radio with the transmitter turned off or similar to the sound of a high speed train passing by.

Hiss means that the stimulus type is constant and consists of all frequency components however experiencing natural signal growth and signal decay. A hiss may sound like steam escaping from a vent or an angry cat or an agitated snake.

Modulated means that the stimulus type is being modulated by another signal similar to an amplitude modulation (AM) or frequency modulation (FM). A modulated sound does not sound remind of anything from this world. Most modulated sounds find applications in science fiction movies.

Siren means that the stimulus type is being modulated by high frequency ascending and descending waveform. A siren will sound like a police care trying to get the drivers attention.

Warble means that the stimulus type is being modulated by low frequency ascending and descending waveform. A warble may sound like a piece of machinery working normally or working under stress.

A custom stimulus generator provides a custom stimulus signal type, for example, but not limited to, a recording of a person's voice, such as that of crying baby to subliminally stimulate a mother's central nervous system.

The sleep practitioner may load the stimulus generator combinations as needed via remote terminal instructions into the sequence memory array.

The sleep practitioner may also load the stimulus generator frequencies, intensities and combinations as needed via remote terminal instructions into the appropriate stimulus generator registers.

All load, control, address and data values are being communicated from the device controller through the internal control bus via the individual registers.

The device controller communicates the information of which is the current generator or combination is being selected.

Figure 7B:
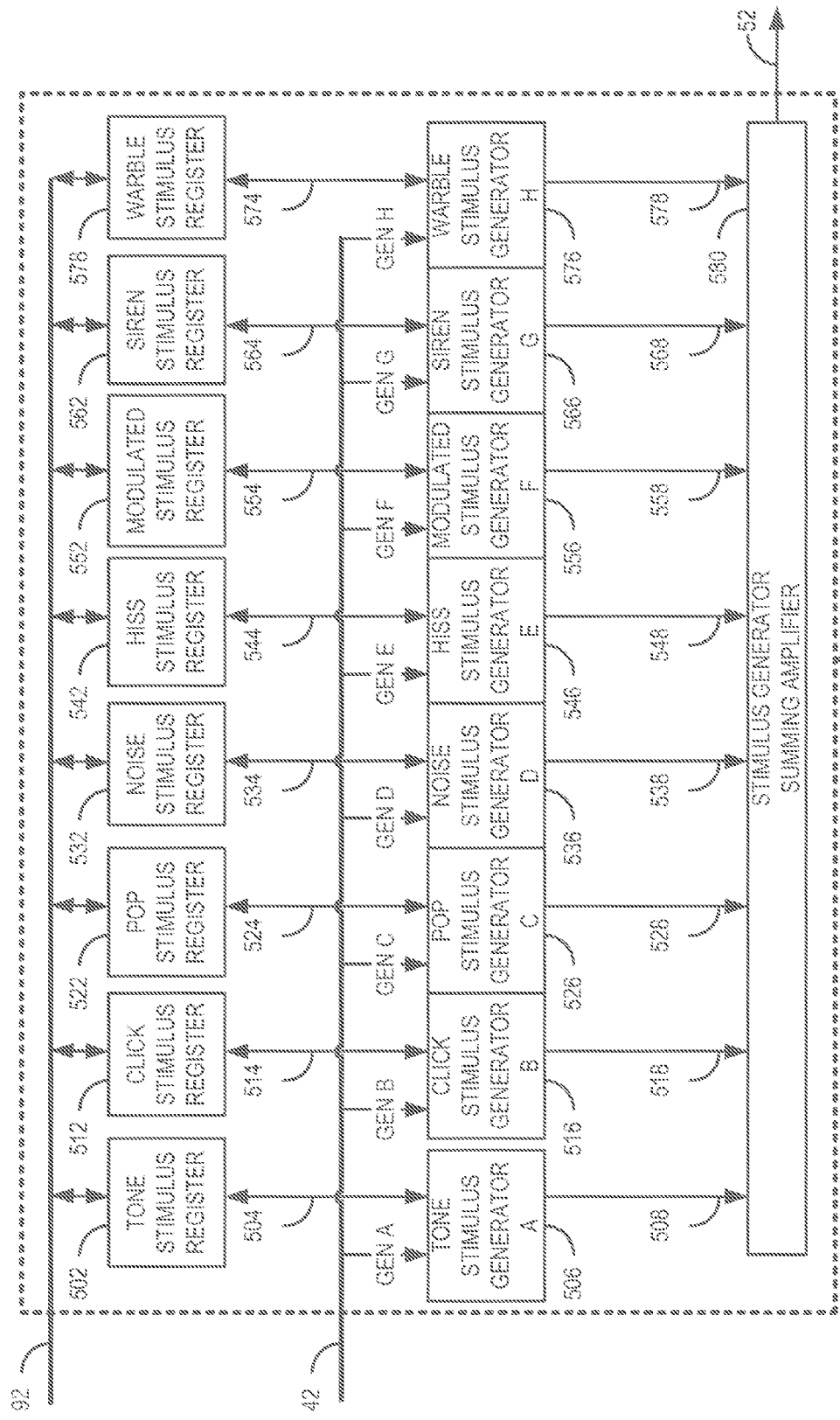
FIG. 7B is a detailed electrical block diagram of a Stimulus Generator according to one example of the present subject matter.

Tone stimulus generator range: 0 to 255 variations
Click stimulus generator range: 0 to 255 variations
Pop stimulus generator range: 0 to 255 variations
Noise stimulus generator range: 0 to 255 variations
Hiss stimulus generator range: 0 to 255 variations
Modulated stimulus generator range: 0 to 255 variations
Siren stimulus generator range: 0 to 255 variations
Warble stimulus generator range: 0 to 255 variations Referring to FIG. 7B, there is indicated more specifically by numeral 50 a detailed block diagram of the stimulus generator. The input of the stimulus generator 50 is the stimulus generator select signal 42. The generator select signal 42 connects to the bank of stimulus tone generators 506, 516, 526, 536, 546, 556, 566, and 576. The stimulus generator select signal 42 connects to the sequence address generator 406 input select port. The generator signal 42 connects to the tone stimulus generator 506 Gen A enable port. The tone stimulus generator 506 connects to the stimulus generator-summing amplifier 580 via connection 508. The tone stimulus generator 506 receives its programmable parameters through the 8-bit parallel connection 504 from the tone stimulus generator register 502. The tone stimulus generator register 502 can be written and read-back through the 8-bit internal control bus 92. The generator signal 42 connects to the click stimulus generator 516 Gen B enable port. The click stimulus generator 516 connects to the stimulus generator-summing amplifier 580 via connection 518. The click stimulus generator 516 receives its programmable parameters through the 8-bit parallel connection 514 from the click stimulus generator register 512. The click stimulus generator register 512 can be written and read-back through the 8-bit internal control bus 92. The generator signal 42 connects to the pop stimulus generator 526 Gen C enable port. The pop stimulus generator 526 connects to the stimulus generator-summing amplifier 580 via connection 528. The pop stimulus generator 526 receives its programmable parameters through the 8-bit parallel connection 524 from the pop stimulus generator register 522. The pop stimulus generator register 522 can be written and read-back through the 8-bit internal control bus 92. The generator signal 42 connects to the noise stimulus generator 536 Gen D enable port. The noise stimulus generator 536 connects to the stimulus generator-summing amplifier 580 via connection 538. The noise stimulus generator 536 receives its programmable parameters through the 8-bit parallel connection 534 from the noise stimulus generator register 532. The noise stimulus generator register 532 can be written and read-back through the 8-bit internal control bus 92. The generator signal 42 connects to the hiss stimulus generator 546 Gen E enable port. The hiss stimulus generator 546 connects to the stimulus generator-summing amplifier 580 via connection 548. The hiss stimulus generator 546 receives its programmable parameters through the 8-bit parallel connection 544 from the hiss stimulus generator register 542. The hiss stimulus generator register 542 can be written and read-back through the 8-bit internal control bus 92. The generator signal 42 connects to the modulated stimulus generator 556 Gen F enable port. The modulated stimulus generator 556 connects to the stimulus generator-summing amplifier 580 via connection 558. The modulated stimulus generator 556 receives its programmable parameters through the 8-bit parallel connection 554 from the modulated stimulus generator register 552. The modulated stimulus generator register 552 can be written and read-back through the 8-bit internal control bus 92. The generator signal 42 connects to the siren stimulus generator 566 Gen G enable port. The siren stimulus generator 566 connects to the stimulus generator-summing amplifier 580 via connection 568. The siren stimulus generator 566 receives its programmable parameters through the 8-bit parallel connection 564 from the siren stimulus generator register 562. The siren stimulus generator register 562 can be written and read-back through the 8-bit internal control bus 92. The generator signal 42 connects to the warble stimulus generator 576 Gen H enable port. The warble stimulus generator 576 connects to the stimulus generator-summing amplifier 580 via connection 578. The warble stimulus generator 576 receives its programmable parameters through the 8-bit parallel connection 574 from the warble stimulus generator register 572. The warble stimulus generator register 572 can be written and read-back through the 8-bit internal control bus 92. The stimulus generator-summing amplifier 580 connects to the stimulus escalator via the stimulus signal 52.

A single selected stimulus generator issues one pulse of its specific signal type for the length of the incoming stimulus duration.

The stimulus generator described herein may provide anti-habituating sleep therapy using different types of stimuli in order to avoid patient habituation to the stimuli signal. In order to avoid habituation to certain stimuli types, a multitude of different stimuli types may be generated and activated as needed. The sleep practitioner can input the stimulation sequence into the device for diagnosis and therapy.

The device may also provide for a fixed operation/manual mode so that the sleep lab practitioner can operate the unit in manual mode for the purpose of experimenting, diagnosing and prescribing the optimum range for specific sleep patient's stimuli regimen.

In one embodiment, a stimulus generator for a closed loop neuromodulator includes a plurality of stimulus generators, corresponding plurality of stimulus generator registers, and a stimulus generator summing amplifier. The plurality of stimulus generators may include eight stimulus generators each directed at different generating different stimuli. The eight stimulus generators may include a tone generator, a click generator, a pop generator, a noise generator, a hiss generator, a modulated generator, a siren generator, and a warble generator.

Stimulus Escalator

A stimulus escalator may receive a stimulus signal 52, a stimulus start signal 32, and a stimulus rate signal 34 from a stimulus generator as shown in FIGS. 2A and 2B. In an effort to avoid overly stimulating a sleep patient it is often effective to start with a relatively low level stimulus and increase the stimulus level until the appropriate level is reached. The stimulus escalator implements this rationale, by receiving the input signals listed above and emitting a corresponding driver signal with a given level signal. The stimulus escalator may determine how to increase each signal (e.g. linearly, exponentially, etc.)

Referring to FIG. 8A, there is indicated more specifically by numeral 60 a stimulus escalator. The stimulus escalator 60 receives its inputs via the stimulus signal 52 from the stimulus generator 50 and stimulus start signal 32 and stimuli rate signal 34 from the stimulus timer 30. The stimulus escalator 60 connects via the driver signal 62 to the EMI/ESD hardened transducer driver 70. For the purpose of inter-device communication command and control, the Stimulus Escalator 60 connects to the common Device Controller Bus 92. A detailed description of the stimulus escalator 60 is provided below and in a separately filed U.S. Provisional Patent Application titled Stimulus Escalator for a closed loop neuromodulator, filed on Aug. 22, 2008, the contents of which are hereby incorporated by reference herein.

A function of the stimulus escalator is to provide anti-habituating sleep therapy to avoid habituation to stimuli levels in patients. In order to avoid habituation to certain stimuli levels a multitude of different stimuli levels have to be generated and activated as needed in very specific and deliberate level escalation. The escalator activates a very specific stimulus level as needed and as prescribed. The sleep practitioner can input the stimulation escalation gain and escalation envelope function via an escalation table into the device for diagnosis and therapy.

There is a need for fixed operation/manual mode so that the sleep lab practitioner can operate the unit in manual mode for the purpose of experimenting, diagnosing and prescribing the optimum range for specific sleep patient's stimuli level regimen.

The stimulus escalator decides on which stimulus level is to be applied and with what escalation envelope function. The envelope functions can be but are not limited to:
1. Constant
2. Linear
3. Polynomial
4. Exponential
5. Logarithmic Constant means that the same stimulus level escalation envelope function is constant that the same stimulus level is repeatedly applied every time a stimulus is being issued.

Linear means that the same stimulus level escalation envelope function is linear and in the form $Y=Ax+B$ so that the next applied stimulus obeys the aforementioned mathematical relationship with the previously issued stimulus.

Polynomial means that the same stimulus level escalation envelope function is polynomial and in the form $Y=A*x^2+B*x+C$ so that the next applied stimulus obeys the aforementioned mathematical relationship with the previously issued stimulus.

Exponential means that the same stimulus level escalation envelope function is polynomial and in the general form $Y=A*e^{-(x/B)}$, so that the next applied stimulus obeys the aforementioned mathematical relationship with the previously issued stimulus.

Logarithmic means that the same stimulus level escalation envelope function is polynomial and in the general form $Y=A*Log_n(B*x)$, so that the next applied stimulus obeys the aforementioned mathematical relationship with the previously issued stimulus.

An element of the stimulus escalator is its escalation memory array which is loaded with the escalation level envelope values as selected and described above either on start-up or during operation by the device controller who manages and keeps track of the stimulus sequencing.

The escalation memory array is of a 256×8-bit <00Hex to <FFHex> read writable random access memory (RAM) type. The escalation memory array can be any size memory and is not limited to 256×8-bit.

The sleep practitioner may load the escalation values as needed via remote terminal instructions into the escalation memory array.

All load, control, address and data values are being communicated from the device controller through the internal control bus via the individual registers.

The device controller communicates the escalation information of which is the current stimulus level, which is the next stimulus level and which was the last stimulus level issued.

Escalation address generator range: 0 to 255 addresses
Escalation load control range: 8-bit (clear, set, reset, clock)
Escalation load address range: 8-bit (A0 . . . A7)
Escalation date load range: 8-bit (DB0 . . . DB7)

The device controller keeps track of the following: escalation start levels and escalation end levels.

Upon receipt of the stimulus start signal, the 8-bit or N-bit programmable escalation generator/counter selects the next escalation level upon receipt of the stimulus rate signal for generating the escalation level of the appropriate stimulus generator. With each new stimulus duration signal clocked into the escalation address generator, a new address is being generated and input into the escalation memory array for selection of the particular stimulus level for that specific stimulus.

Figure 8B:
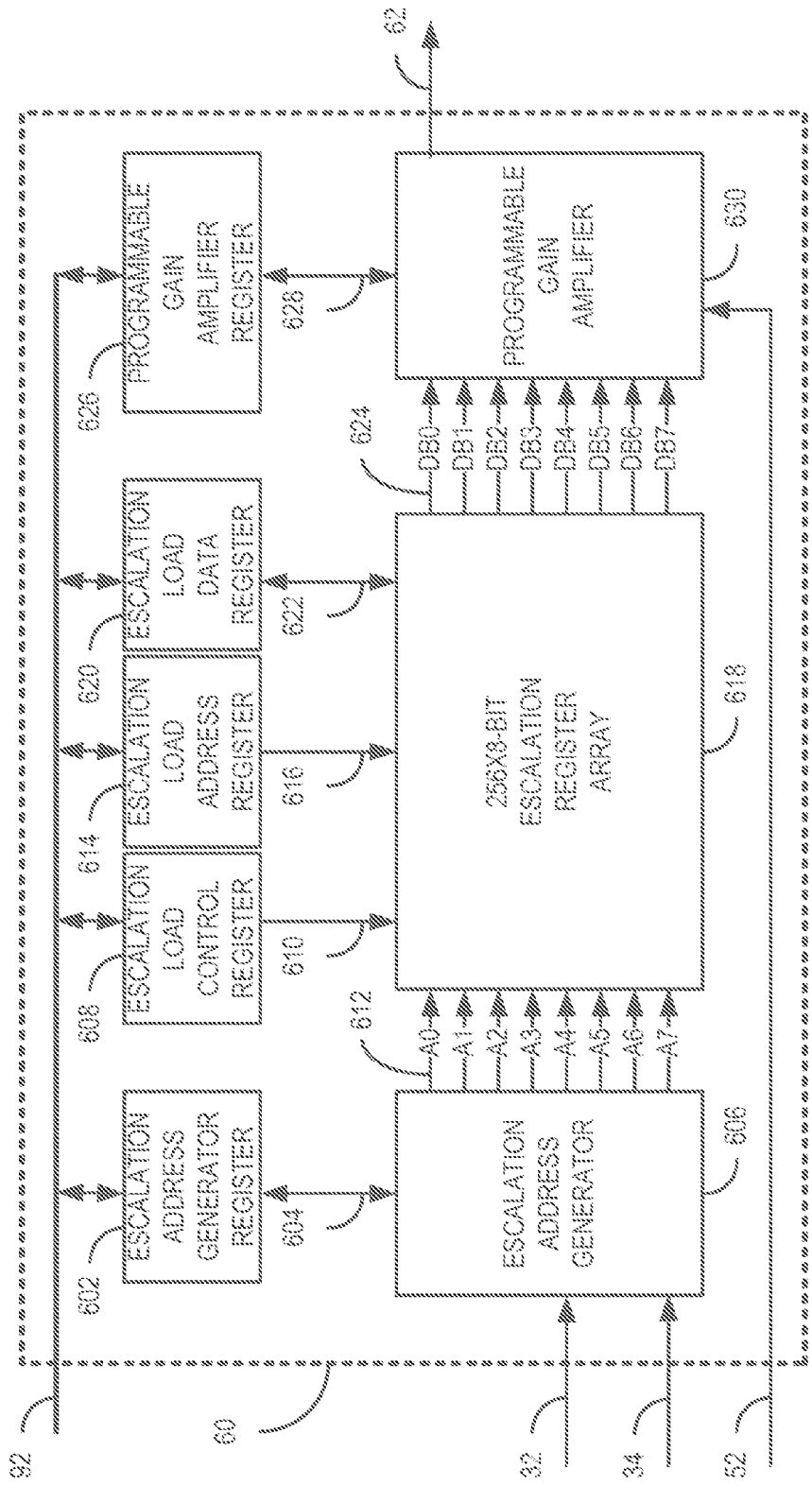
FIG. 8B is a detailed electrical block diagram of a Stimulus Escalator according to one example of the present subject matter.

Referring to FIG. 8B, there is indicated more specifically by numeral 60 a detailed block diagram of the stimulus escalator. The inputs of the stimulus escalator 60 are the stimulus start signal 32, the stimulus rate signal 34 and the stimulus signal 52. The stimulus start signal 32 connects to the escalation address generator 606 internally gated enable port. The stimulus rate signal 34 connects to the escalation address generator 606 clock input port. The escalation address generator 606 connects to the escalation memory array 618 via the address selection bus 612. The escalation address generator 606 receives its programmable count parameters through the 8-bit parallel connection 604 from the escalation address generator 602. The escalation address generator register 602 can be written to and read-back from the 8-bit internal control bus 92. The escalation memory array 618 connects to the programmable gain amplifier 630 via the escalation data bus 624. The escalation memory array 618 receives its escalation load control commands through the 8-bit parallel connection 610 from the escalation load control register 608. The escalation load control register 608 can be written to and read-back from the 8-bit internal control bus 92. The escalation memory array 618 receives its escalation address load commands through the 8-bit parallel connection 616 from the escalation load address register 614. The escalation load address register 614 can be written and read-back through the 8-bit internal control bus 92. The escalation memory array 618 receives its escalation data load commands through the 8-bit parallel connection 622 from the escalation load data register 620. The escalation load data register 620 can be written to and read-back from the 8-bit internal control bus 92. The programmable gain amplifier 630 receives its gain setting data through the 8-bit parallel connection 628 from the programmable gain amplifier register 626. The programmable gain amplifier register 626 can be written to and readback from the 8-bit internal control bus 92. The programmable gain amplifier 430 connects to the EMI/ESD hardened transducer driver via the driver signal 62.

The programmable gain amplifier 430 can be programmed in 0.3 dB gain steps per bit. In a gain block the gain is expressed in decibel (dB). Loss or gain is expressed in dB. The loss/gain range of the programmable gain amplifier is about 76.5 dB but more or less possible.

In one embodiment, a stimulus escalator for a closed loop neuromodulator includes an escalation address generator, an escalation register array, and a programmable gain amplifier. In another embodiment, the stimulus escalator further includes an escalation address generator register, where the escalation address generator is configured to receive escalation addresses from the escalation address generator register. In another embodiment, the stimulus escalator further includes an escalation load control register, an escalation load address register, and an escalation load data register. In yet another embodiment, the stimulus escalator further includes a programmable gain amplifier register.

EMI/ESD Hardened Transducer Driver

A transducer driver may receive input from a stimulus escalator and may then transmit this signal to a transducer, as shown in FIGS. 2A and 2B. Moreover, as also depicted in FIGS. 2A and 2B, this sensor interface may be the final output or exit location for a stimulation controller and may therefore be a potential inlet for EMI and ESD. Thus, the transducer driver may be equipped with EMI and ESD protection to prevent interference with and/or damage to the transducer driver or the overall controller.

Figure 9A:
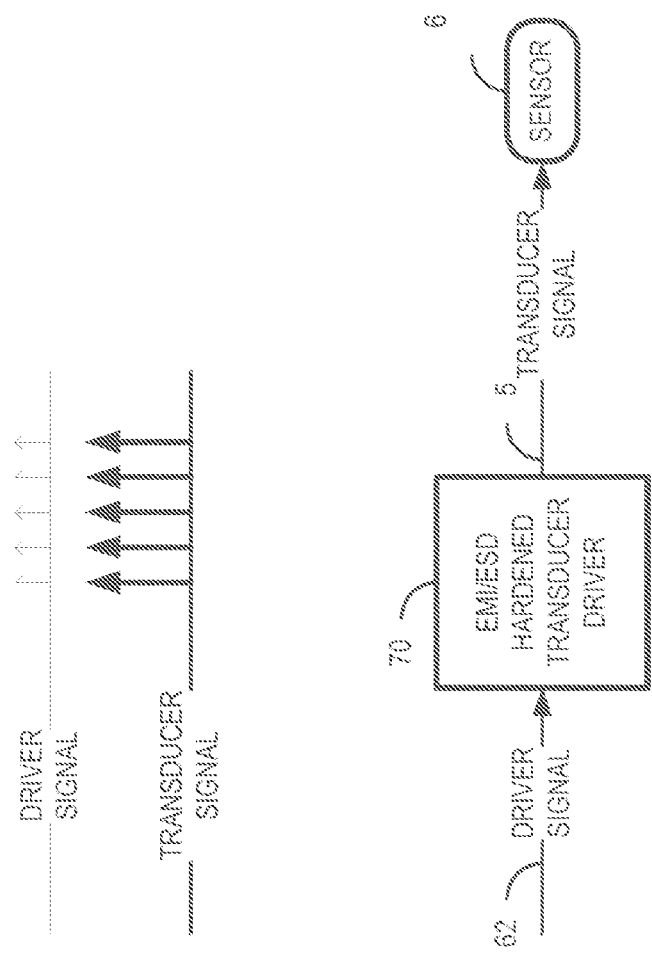
FIG. 9A illustrates generally an electrical block diagram of an EMI/ESD Hardened Transducer Driver.

Referring to FIG. 9A, there is indicated more specifically by numeral 70 an EMI/ESD hardened transducer driver. The EMI/ESD hardened transducer driver 70 receives its input via the driver signal 62 from the output of the stimulus escalator 60. The EMI/ESD hardened transducer driver 70 connects via the pair of wire terminals 5 to the transducer 6. A detailed description of the EMI/ESD hardened transducer driver 70 is provided below and in a separately filed U.S. Provisional Patent Application titled EMI/ESD Hardened Transducer Driver for a closed loop neuromodulator, filed on Aug. 22, 2008, the contents of which are hereby incorporated by reference herein.

Even though most countries have legal requirements that mandate EMC compliance, electronic devices must still work correctly when subjected to certain amounts of electromagnetic interference (EMI), and should not emit EMI, which could interfere with other equipment. This issue is known in the industry as self-compatibility and this fact is crucial to the operation of the invention because of the very low analog biomedical signals involved.

A robust sleep therapy system works reliably in a modern harsh and hostile environment in close proximity to cell phone transmissions, wireless internet transmitters, wireless phone system transmitters, etc. Modern environments, even home environments have high concentration of EMI and RFI especially in the 60 Hz/120 Hz due to home power wiring and fluorescent, compact fluorescent lighting and switch mode power supplies operating in home appliances. Additionally, wireless technology such as wireless telephone transmissions, wireless routers, cordless phone systems, remote control burglar alarm devices, remote control toys, and the like may emit EMI. Issues of self-compatibility are also a concern and involve minimizing the emission of EMI that could interfere with other portions of the device or other equipment. Thus, EMI that could interfere with a sleep device is a concern, but the EMI emitted by the device is also a concern.

ESD hardening protects sensitive electronic due to common and regular handling of the product containing the sensitive electronics in a standard home environment were static discharges are common especially during the winter seasons in colder climate zones and during the dry seasons in warmer climate zones.

EMI/ESD hardening against the aforementioned offenders not only satisfies domestic and international requirements on emissions and susceptibility but also results in robust operation, cleaner internal signals, improved signal-to-noise-ratio (SNR) and greater dynamic range.

Due to the nature of the device application, through its typical long sensor and transducer wires, exposure of the output to ESD may potentially destroy the transducer driver circuitry. Thus, special ESD countermeasures have to be put in place in order to prevent damage or total destruction of the sensitive, low power circuitry.

The following is a list of EMC component level countermeasures for the EMI/ESD hardened transducer driver:
1. Feed-through capacitors
2. Balanced drive amplifier
3. Matched gain setting resistor network to maintaining high CMRR
4. Ferrite beads, series EMI suppression element
5. Filter capacitors, parallel EMI suppression element
6. Common mode RF filter, parallel EMI suppression element
7. Common mode RF choke, series EMI suppression element
8. Capacitor as signal decoupling, parallel EMI suppression element
9. Inductor as signal lead filtering, series EMI suppression element
10. Capacitor as power feed filtering, parallel EMI suppression element
11. Inductor as power feed filtering, series EMI suppression element
12. Schottky diodes, EMI suppression parallel element
13. Resistors, series EMI suppression element
14. Inductors, series EMI suppression element
15. Cascaded capacitor banks, 0.01 uf and 10 uF
16. Inductors in V+ and V− feeds before capacitor cascade, power feed output For the purpose of EMI/RFI shielding of the EMI/ESD hardened transducer driver 70, a metal case is mounted on to of the PCB picket fenced circuit boundary. The picket fence is connected to the ground pane and ground flooded signal layer.

The following is a list of PCB based EMC countermeasures for the EMI/ESD hardened transducer driver:
1. Power and ground planes
2. Layer flooding
3. Picket fencing
4. Short and narrow signal traces
5. Short and wide power traces
6. Components must be placed in close proximity to each other
7. PCB routing must be as short as possible
8. Short and wide traces are better than long and skinny ones The following operational parameters that are adjustable within the EMI/ESD hardened sensor Interface:
1. Amplifier gain (−20 dB to +20 dB)

Referring to FIG. 9B there is indicated more specifically by numeral 70 a detailed block diagram of the EMI/ESD hardened transducer driver. The input signal 42 for the EMI/ESD hardened transducer driver 70 is being generated by the output of the stimulus escalator. The supply filtered balanced drive amplifier 704 amplifies the input signal 42 to match the appropriate drive level of the externally connected transducer 6. The balanced output wire pair 720 of the supply filtered balanced drive amplifier connects to the ESD protection circuit 706. The balanced output wire pair 722 of the ESD protection circuit 706 connects to the internal EMI/RFI filter 708. The balanced output wire pair 724 of the internal EMI/RFI filter 708 penetrates the metal casing 701 and connects to the external EMI/RFI filter. The balanced output wire pair 726 of the external EMI/RFI filter connects to the transducer output connector 712. The metal shield 701 covers as the sensitive signal carrying analog signal circuit as indicated and is connected to a multitude of ¼" spaced ground connections 701 for providing a very low impedance connection to circuit ground even at extremely high frequencies. The metal shield 701 in connection with the printed circuit ground plane on the opposite side of the PCB and with an RF tight picket fence constructed of interleaved vias that connect the ground plane to the ground flooded top component copper layer forms a continuous electrostatic shield around the entire volume of the EMI/ESD hardened transducer driver 70.

Figure 9C:
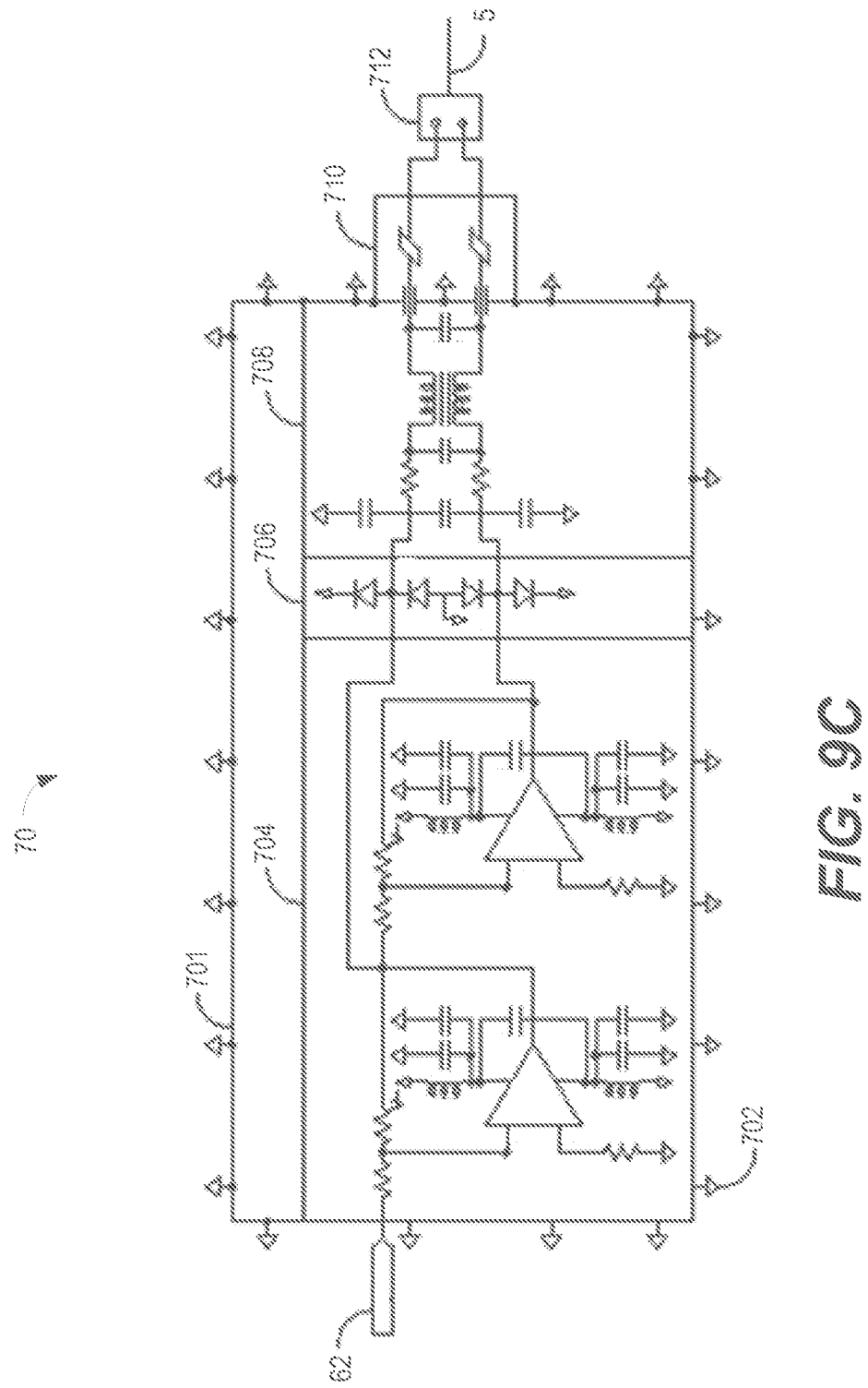
FIG. 9C is an electrical schematic diagram of an EMI/ESD Hardened Transducer Driver.

Referring to FIG. 9C, there is indicated a schematic diagram specifically by numeral 70 an EMI/ESD hardened transducer driver.

The input signal 42 for the EMI/ESD hardened transducer driver 50 is being generated by the output of the stimulus escalator. The supply filtered balanced drive amplifiers 704 comprise of operational amplifiers (opamps) U1 and U2. Both opamps U1 and U2 are connected in a two-amplifier balanced drive amplifier configuration. The balanced amplifier gain is set by the ratio of the resistors R2/R1 and R4/R3. Resistor R2 by means of connection to signal ground provides drift compensation for opamp U1. Resistor R5 by means of connection to signal ground provides drift compensation for opamp U2. Negative supply filtering of the operational amplifier U1 comprises of a conducted RF power absorbing inductor L1 and a conducted RF power suppressing cascaded capacitor bank consisting of C1 and C3 in parallel to ground. The conducted RF power absorbing inductor L1 is connected in series with the negative supply power terminal V− and the negative power supply terminal 2 of the operational amplifier U1. Positive supply filtering of the operational amplifier U1 comprises of a conducted RF power absorbing inductor L2 and a conducted RF power suppressing cascaded capacitor bank consisting of C2 and C5 in parallel to ground. The conducted RF power absorbing inductor L2 is connected in series with the positive supply power terminal V+ and the positive power supply terminal 5 of the operational amplifier U1. Furthermore, conducted emissions bypassing capacitor C4 is connected across the U1 operational amplifier power pin 2 and pin 5. Negative supply filtering of the operational amplifier U2 comprises of a conducted RF power absorbing inductor L3 and a conducted RF power suppressing cascaded capacitor bank consisting of C6 and C8 in parallel to ground. The conducted RF power absorbing inductor L3 is connected in series with the negative supply power terminal V− and the negative power supply terminal 2 of the operational amplifier U2. Positive supply filtering of the operational amplifier U2 comprises of a conducted RF power absorbing inductor L4 and a conducted RF power suppressing cascaded capacitor bank consisting of C7 and C10 in parallel to ground. The conducted RF power absorbing inductor L4 is connected in series with the positive supply power terminal V+ and the positive power supply terminal 5 of the operational amplifier U2. Furthermore, conducted emissions bypassing capacitor C9 is connected across the U2 operational amplifier power pin 2 and pin 5. The balanced ended output of the supply filtered balanced drive amplifier 704 connects to the output ESD protection 706. The ESD protection 706 comprises primarily of diodes D1, D2, D3 and D4. The cathode of D1 is connected to the positive supply terminal. The anode of D1 is connected to the output terminal 1 of opamp U1. The anode of D2 is connected to the negative supply terminal. The cathode of D2 is connected to the output terminal 1 of opamp U1. The cathode of D4 is connected to the positive supply terminal. The anode of D4 is connected to the non-inverting input terminal 3 of opamp U2. The anode of D3 is connected to the negative supply terminal. The cathode of D3 is connected to the non-inverting input terminal 3 of opamp U2. D1 through D4 present the parallel clamping element of the ESD protected opamp input terminal. Resistors R7 and R8 in connection with the Diodes D1, D2, D3 and D4 form an ESD suppression circuit. Resistors R7 and R8 form the series ESD power absorbing elements. It is clearly shown that the output terminal 1 of the operational amplifiers U1 and U2 of the supply filtered balanced drive amplifier 704 are EMI and ESD protected. The internal EMI/RFI filter 708 comprises a differential mode filtering capacitor C15 connected to C16 and C17. Also connected to C16 and C17 is the input wire pair of a high frequency common mode choke L5. The output wire pair of the high frequency common mode choke L5 is connected to the input of the two ESD energy absorbing series resistors R7 and R8 and to a second filter capacitor C14. The output wire pair of the energy absorbing resistors R7 and R8 is connected to another set of EMI suppressing filter capacitors C11 C12 and C13. The sensor output connector 712 comprises of connector J2 with the two-signal wire pair leads designated as pin 1 and pin 2 respectively. The external EMI/RFI 710 filter comprises of a pair of ferrite beads FB1 and FB2 acting as the filter series element, and of a pair of metal shield penetrating feed-through capacitors C16 and C17 as the parallel element to ground for common mode filtering. The EMI/ESD hardened transducer driver 70 is designed to drive various transducer types.

The following is a list of possible transducers that may be connected to the EMI/ESD hardened transducer driver 70.

Acoustic transducers by which a sound is introduced into the ear canal or the room to disrupt the undesired behavior and pattern.

Ultrasonic transducers by which an audio tone is used to modulate an ultrasonic beam directed at the patient. The brain demodulates the signal and the detected audio signal is perceived as such. The ultrasonic beam is very narrow thus; only the patient is subjected to it, the rest of the space remains quiet and unaffected. Therefore, no aural ear bud phones would be needed.

Tactile transducers by which a mechanical device such as the mechanical agitator applies a gentle touch to the patient's skin.

Visual transducers by which a flash of light is applied to the eyes. An eye cover with red LED which would turn on for a short amount of time during stimulation.

Puff-of-Air transducers by which an air puff is applied to the patient's skin.

Electrical transducers (biomedical electrodes) by which a gentle electrical stimulation is applied to the patient's skin.

Alternatively, a signal duplexer can be used in order to utilize the same PVDF sensor that is detecting airflow with pyroelectric and piezoelectric properties as the stimuli delivering transducer. The pyroelectric and piezoelectric properties of the PVDF film are reciprocal. This is because the piezoelectric capability of the film included either converting mechanical vibrations to electrical signals and/or converting electrical signals to mechanical, including audio or ultrasound vibrations.

In one embodiment, an EMI/ESD hardened transducer driver for a closed loop neuromodulator includes a supply filtered balanced drive amplifier, an ESD protection device, at least one EMI/RFI filter, a grounded metal shield, and a transducer output connector. In another embodiment, both an internal and an external EMI/RFI filter are provided. In another embodiment, the external EMI/RFI filter is situated along a signal path outside the grounded metal shield. In yet another embodiment, the internal EMI/RFI filter is situated along a signal path inside the grounded metal shield. In another embodiment, each of the elements are arranged in series.

Diagnostic Indicator and PSG Interface

In sleep medicine, a stimulation controller may be used to receive input from a sensor on a patient, analyze the input, and further may be used to activate a transducer to stimulate the patient. FIGS. 1A and 1B show at least two embodiments of a stimulation controller in position on a patient. The following description relates to a diagnostic indicator and PSG interface included in a stimulation controller.

As shown in FIGS. 2A and 2B, the diagnostic indicator and PSG interface may receive input from various devices in a stimulation controller. The purpose of the diagnostic indicator is to provide an indication to the user or the sleep practitioner of what information the stimulation controller is receiving, what functions it is performing, and what information it is transmitting. The diagnostic indicator may include a series of LED's indicating such information. Additionally, the diagnostic indicator and PSG interface may be compatible with a PSG machine and thereby provide a sleep practitioner with more sophisticated output beyond LED output.

A detailed description of the Diagnostic Indicator and PSG Interface 80 is provided below and in a separately filed U.S. Provisional Patent Application titled Diagnostic Indicator and PSG Interface for a closed loop neuromodulator, filed on Aug. 22, 2008, the contents of which are hereby incorporated by reference herein.

Referring to FIG. 10A, there is indicated more specifically by numeral 80 a Diagnostic Indicator and PSG Interface. The Diagnostic Indicator and PSG Interface 80 receives multiple inputs from the other elements of the closed loop neuromodulator. The following signals are inputs to the Diagnostic Indicator and PSG Interface 80: The Analog airflow signal 130 and the digital airflow signal 12 from the EMI/ESD Hardened Sensor Interface, the activity signal 22, from the Activity detector, the stimuli signal 52 from the Stimulus Generator and the driver signal 62 from the Stimulus Escalator. A push button switch 38 also connects to the Diagnostic Indicator and PSG Interface 80 via the push button input connection 39 for the purpose of activating the sleep therapy delay timer. The following signals are outputs from the Diagnostic Indicator and PSG Interface 80: The therapy delay indicator 81, the inhalation indicator 82, the power indicator 83, the therapy mode indicator 84, the apnea indicator 85, the apneas detected indicator 86, the diagnostic mode indicator 87, the exhalation indicator 88, and the stimulus indicator 89. The Diagnostic Indicator and PSG interface 80 connects via the PSG connection 7 to the PSG machine 8. A detailed description of the stimulus escalator 40 is provided below.

The diagnostic indicator and PSG interface provide a simple human-machine interface for indicating internal device operation and connection to external diagnostic instrumentation such as a PSG for further analysis of patient data gathered by the closed loop neuromodulator.

Pushing the therapy delay button when the unit is in therapy delay mode, de-activates the therapy delay mode, turns the therapy delay indicator off and resets the count down timer.

The therapy delay indicator 81 notifies the sleep practitioner or patient that the therapy delay timer is active and that the device will not provide any therapy until that indicator turns off.

The inhalation indicator 82 notifies the sleep practitioner or the patient that the patient respiration cycle is currently in the inhalation phase.

The power indicator 83 notifies the sleep practitioner or the patient that the power to the closed loop neuromodulator is turned on and that the device has passed its self-test routing.

The therapy mode indicator 84 notifies the sleep practitioner or the patient that the closed loop neuromodulator is currently in therapy mode.

The apnea indicator 85 notifies the sleep practitioner that the patient is currently experiencing a sleep apnea episode or any other CNS disorder that the modulator is configured for.

The apneas detected indicator 86 notifies the sleep practitioner or the patient that the patient has experienced sleep apneas during the current therapy or diagnostic cycle.

The diagnostic mode indicator 87 notifies the sleep practitioner or the patient that the closed loop neuromodulator is currently in therapy mode.

The exhalation indicator 88 notifies the sleep practitioner or the patient that the patient respiration cycle is currently in the exhalation phase.

The stimulus indicator 89 notifies the sleep practitioner that the patient is currently experiencing a sleep apnea episode and that a stimulus is currently being applied.

Figure 10B:
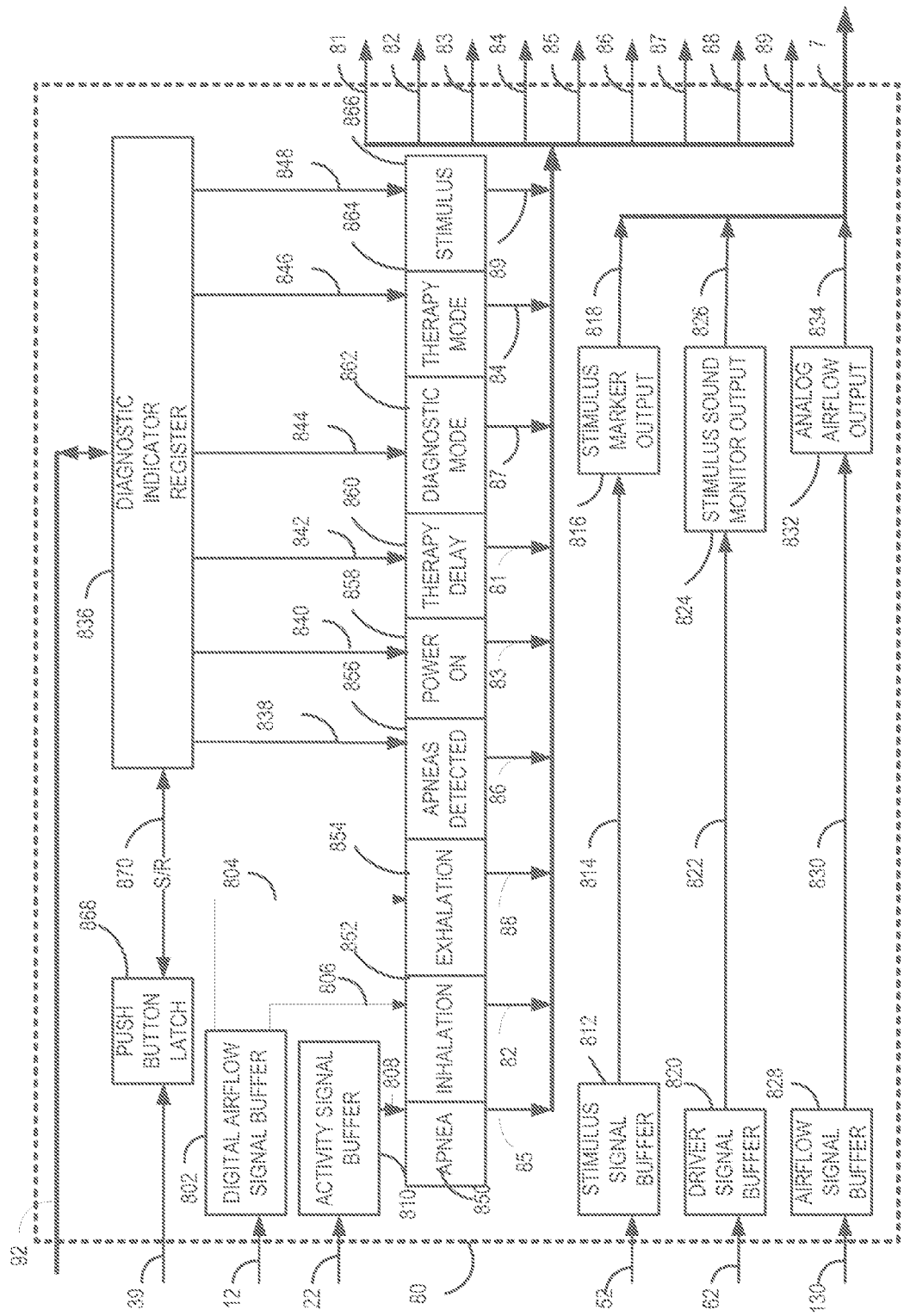
FIG. 10B is an detailed electrical block diagram of a Diagnostic Indicators and PSG Interface according to one example of the present subject matter.

Referring to FIG. 10B, there is indicated more specifically by numeral 80 a detailed block diagram of the diagnostic indicator and PSG interface. The Diagnostic Indicator and PSG Interface 80 receives multiple inputs from the other elements of the closed loop neuromodulator. The Analog airflow signal 130 connects to the airflow signal buffer 828. The Airflow signal buffer output 830 connects to the input of the Analog airflow output 832. The analog airflow output port 834 is bundled together with the PSG connection port 7. The stimuli signal 52 connects to the stimulus signal buffer 812. The stimuli signal buffer output 814 connects to the input of the stimulus marker output 816. The stimulus marker output port 818 is bundled together with the PSG connection port 7. The driver signal 62 connects to the driver signal buffer 820. The driver signal buffer output 820 connects to the input of the stimulus sound monitor output 824. The stimulus sound monitor output 826 is bundled together with the PSG connection port 7. The digital airflow signal 12 connects to the digital airflow signal buffer 802. The Digital airflow signal buffer 802 separates the inhalation phase of the digital airflow signal 12 from the exhalation phase of the digital airflow signal 12. The exhalation output port 804 of the digital airflow signal buffer 802 drives the Exhalation LED driver 854. The output of the exhalation LED driver 854 drives the exhalation indicator 88. The inhalation output port 806 of the digital airflow signal buffer 802 drives the inhalation LED driver 852. The output of the inhalation LED driver 852 drives the inhalation indicator 82. The activity signal 22 connects to the activity signal buffer 810. The activity signal buffer output port 808 of the activity signal buffer 810 drives the input of the apnea LED driver 850. The output of the apnea LED driver 850 drives the apnea indicator 85. The push button switch connection 39 connects to the push button latch 868. The push button latch output 870 connects to a single bit read port of the diagnostic indicator register 836. After the diagnostic indicator, register 836 has accessed and read the status of the push button latch 868, the push button latch 868 clears and is ready to accept another push button activation. The diagnostic indicator register 836 can be written to and read-back from the 8-bit internal control bus 92. Writing to the diagnostic indicator register 836 sets or resets the LED driver driving output bits. The output port 838 of the diagnostic indicator register 836 drives the Apneas detected LED driver 856. The output of the Apneas detected LED driver 856 drives the apneas detected indicator 86. The output port 840 of the diagnostic indicator register 836 drives the power-on LED driver 858. The output of the power-on LED driver 858 drives the power-on indicator 83. The output port 842 of the diagnostic indicator register 836 drives the therapy delay LED driver 860. The output of the therapy delay LED driver 860 drives the therapy delay indicator 81. The output port 844 of the diagnostic indicator register 836 drives the diagnostic mode LED driver 862. The output of the diagnostic mode LED driver 862 drives the diagnostic mode indicator 87. The output port 846 of the diagnostic indicator register 836 drives the therapy mode LED driver 864. The output of the therapy mode LED driver 864 drives the therapy mode indicator 84. The output port 848 of the diagnostic indicator register 836 drives the stimulus LED driver 866. The output of the stimulus LED driver 866 drives the stimulus indicator 89.

In one embodiment, a diagnostic indicator for a closed loop neuromodulator includes a plurality of incoming signal buffers, a diagnostic indicator register, and a plurality of LED drivers. In another embodiment, a stimulus marker output is also included. In another embodiment, the diagnostic indicator includes a stimulus sound monitor output. In yet another embodiment, an analog airflow output is included. In still another embodiment, a push button latch is included.

In another embodiment, a method of using a PSG machine in conjunction with a stimulation controller is provided.

Device Controller and Data Logger

In sleep medicine, a stimulation controller may be used to receive input from a sensor on a patient, analyze the input, and further may be used to activate a transducer to stimulate the patient. FIGS. 1A and 1B show at least two embodiments of a stimulation controller in position on a patient. The following description relates to a device controller and data logger included in a stimulation controller for interfacing with a wide range of sensors.

The device controller and data logger, as shown in FIGS. 2A and 2B, may be placed in communication with various elements of a closed loop neuromodulator via an internal control bus. Each element of the closed loop neuromodulator may contain a register or series of registers that the device controller and data logger is in communication with. The device controller and data logger can write to and read from the several registers throughout the closed loop neuromodulator and log information as well as interpret and react to the information. The device controller and data logger can then write new information to the several registers throughout the closed loop neuromodulator. Parameters relating to stimulus type, stimulus rate, stimulus duration, stimulus level, stimulus escalation, and stimulus sequence are all adjustable for purposes of precisely dosing sleep patients.

The above functions can be completed without the support of sleep practitioner supervision. However, the device controller and data logger may be placed in communication with a remote diagnostic terminal which allows a sleep practitioner to modify various settings within the closed loop neuromodulator to allow for more precise dosing of patients.

A detailed description of the Device Controller and Data Logger 90 is provided below and in a separately filed U.S. Provisional Patent Application titled Device Controller and Data Logger for a closed loop neuromodulator, filed on Aug. 22, 2008, the contents of which are hereby incorporated by reference herein.

Figure 11A:
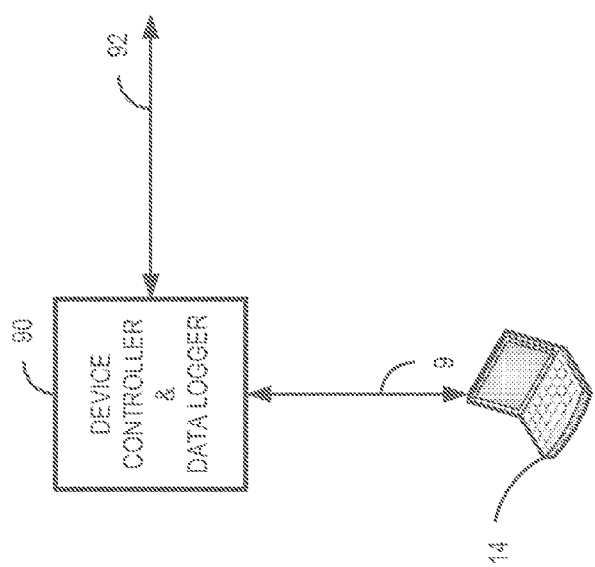
FIG. 11A illustrates generally an electrical block diagram of a Device Controller & Data Logger.

Referring to FIG. 11A, there is indicated more specifically by numeral 90 a device controller and data logger. The common device controller and data logger 90 is connected on the external side to the remote diagnostic terminal 14 and on the internal side to the device controller bus 92. A detailed description of the device controller and data logger 90 is provided below.

A purpose of the device controller and data logger provides an inter-device communication command and control for the closed loop neuromodulator. Furthermore, the device controller and data logger provides an external communication interfaced to the remote terminal for the closed loop neuromodulator. In addition, the state controller within the device controller executes the state-by-state instructions of the auto-adjusting routing, the auto-optimizing routine and the auto-dosing routine. Those routines are described in detail below.

Figure 11B:
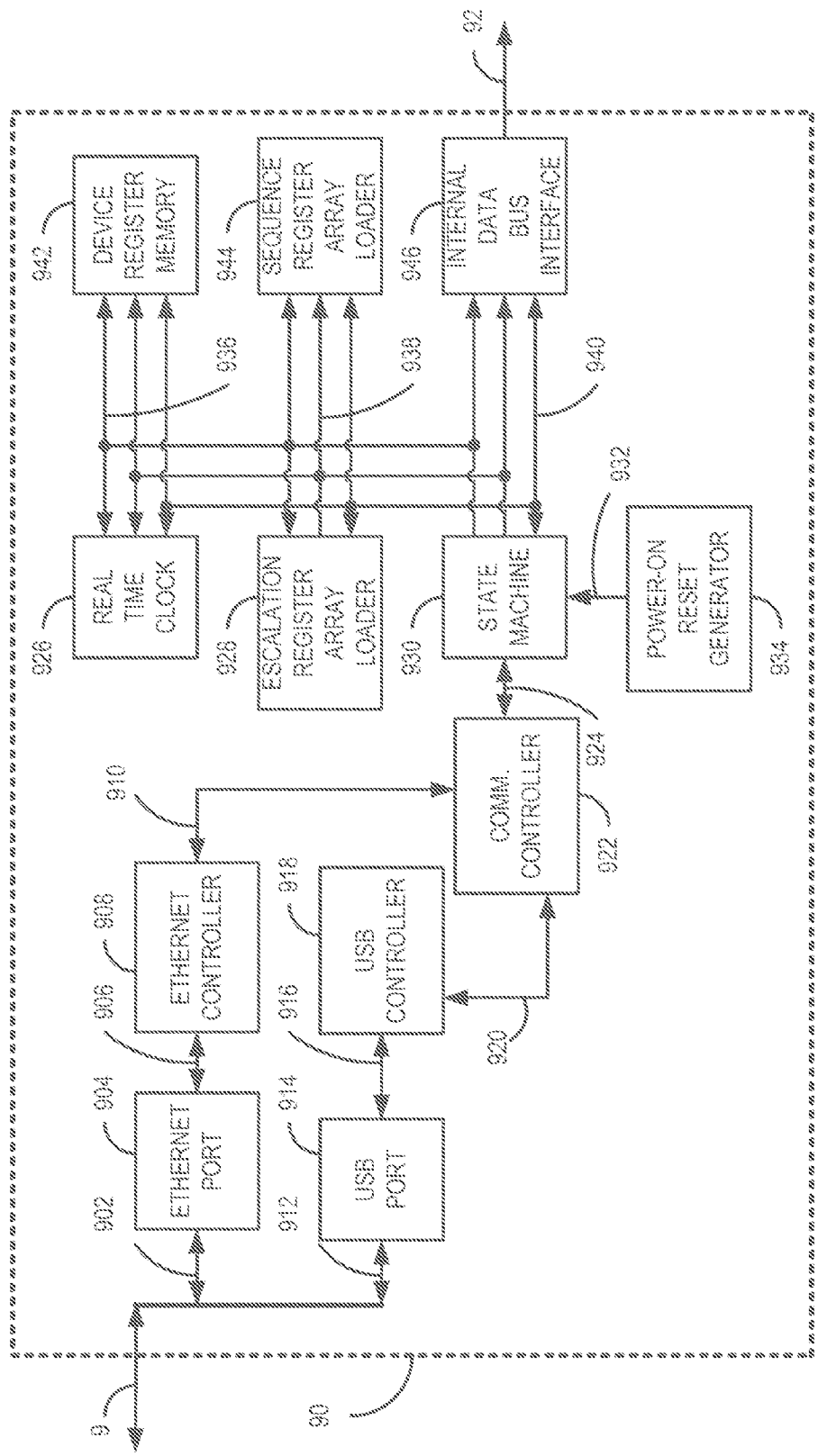
FIG. 11B is detailed electrical block diagram of a Device Controller & Data Logger according to one example of the present subject matter.
Figure 12G:
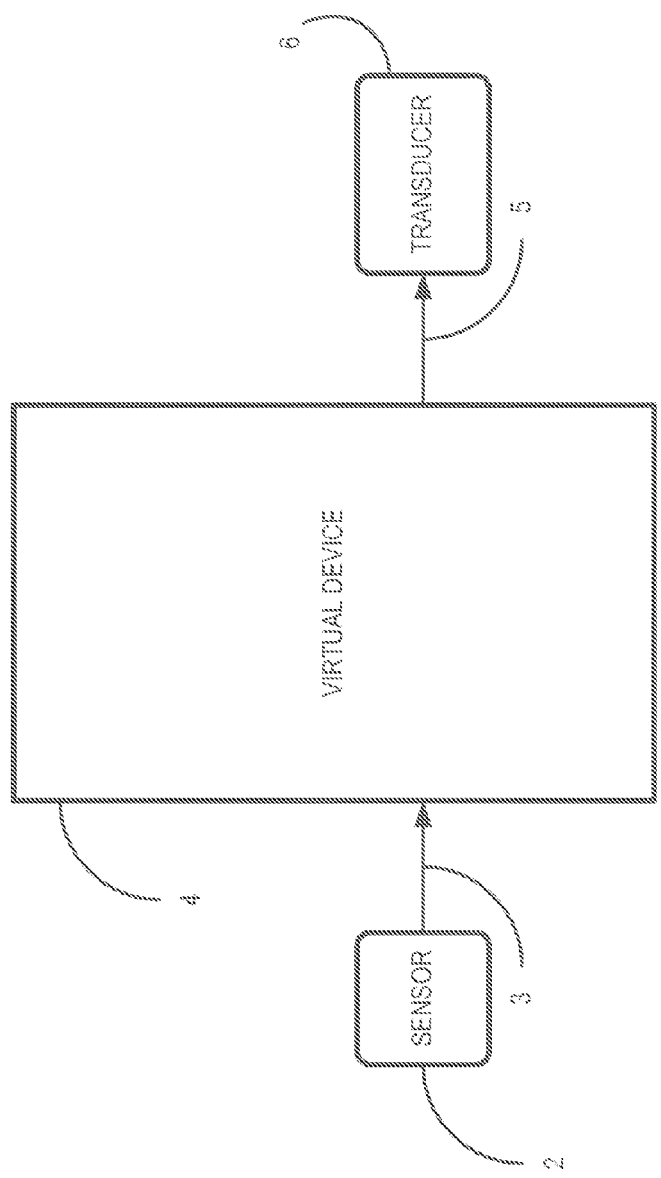
FIG. 12G illustrates generally an electrical block diagram for implementation in a virtual product development platform of a sleep therapy closed loop neuromodulator according to one example of the present subject matter.
Figure 12H:
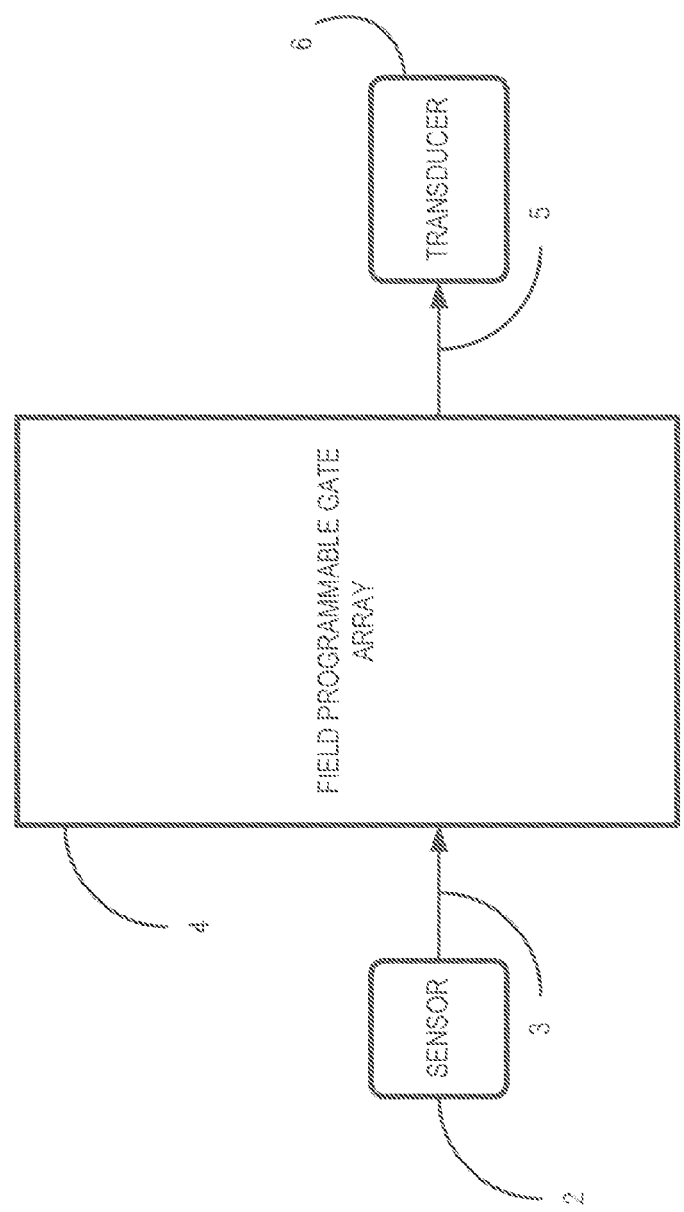
FIG. 12H illustrates generally an electrical block diagram for implementation in a Field Programmable Gate Array (FPGA) of a sleep therapy closed loop neuromodulator according to one example of the present subject matter.

Referring to FIG. 11B, there is indicated more specifically by numeral 90 a detailed block diagram of the device controller and data logger.

The external communication interface 9 includes a USB interface and an Ethernet interface. The external communication interface 9 connects via connection 902 to the Ethernet port 904. The Ethernet 904 port connects to the Ethernet controller 908 via connection 906. The external communication interface 9 connects via connection 922 to the USB port 914. The USB port 914 connects to the USB controller 918 via connection 916. The communication controller 922 connects to the Ethernet controller 908 via connection 910 and to the USB controller via connection 920. The state machine 930 connects to the communication controller 922 via connection 924. The state machine 930 connects to the power-on reset generator 934 via connection 932. The state machine 930 connects to the internal data bus interface 946 via the multi-bit control bus 936, via the multi-bit address bus 938 and via the multi-bit data bus 940. The state machine 930 connects to the stimulation escalation array loader 928 via the multi-bit control bus 936, via the multi-bit address bus 938 and via the multi-bit data bus 940. The state machine 930 connects to the real-time-clock 926 via the multi-bit control bus 936, via the multi-bit address bus 938 and via the multi-bit data bus 940. The state machine 930 connects to the device register memory 942 via the multi-bit control bus 936, via the multi-bit address bus 938 and via the multi-bit data bus 940. The state machine 930 connects to the stimulation sequence array loader 944 via the multi-bit control bus 936, via the multi-bit address bus 938 and via the multi-bit data bus 940. The internal data bus interface 946 communicates to all other bus-interfacing registers of the closed loop neuromodulator through the 8-bit parallel control bus 92.

In one embodiment, a device controller and data logger for a closed loop neuromodulator includes a communication controller, a state machine, an internal data bus interface, a real time clock, an escalation register array loader, a sequence register array loader, and a device register memory. In another embodiment, the communication controller is adapted to connect to a remote terminal via a USB or Ethernet connection. In another embodiment, the device controller further includes a power-on reset generator. In still another embodiment, the device controller is in communication with a closed loop neuromodulator via an internal control bus connected to the internal data bus interface.

Auto-Adjusting, Optimization and Dosing

Start with lowest possible stimuli and increase towards optimum and not starting with highest possible stimuli and decrease towards optimum because highest possible stimuli will generate an arousal of the CNS.

Ideally, the ratio of stimuli generated to airflow-detected occurrences is above 2 to 1. The rationale for this is that the first stimuli signal should not generate any arousal so that it is established that the signal level is low enough as neither to change the sleeping patients sleep state nor to awake him. Then with that base stimuli level established, the next stimuli level generated should be high enough to cause and arousal in order to cause resumption of breathing. Since the first level was not high enough to cause any cortical arousal and the second level was just slightly above the first level, one can safely assume that the second level was not strong enough to neither change the sleeping patients sleep state nor wake him up completely. This device automatically figures out both levels.

Patient setup during a first use includes measuring and setting an actual and optimal level of stimulation for each individual patient automatically during first use, then storing the associated parameters in a setup register.

Making sure that the individual patient responds to the applied stimuli within the predetermined time.

Self Optimizing includes constantly measuring the ratio between applied stimuli and non-breathing events to make sure that the patient changes neither sleep state nor wakes up due to over stimulation. Furthermore making sure that the patient does not remain in an apnea state due to under stimulation Latch in third to the last stimuli gain setting before the resumption of breathing and start there, as the next first stimuli level for the next no breathing episode.

Escalation steps change from soft to mild to moderate to strong then harsh.

Record in memory the last gain setting that caused the resumption of breathing.

Typically, stimuli type optimization is performed in a clinic on a diagnostic level. The method of stimuli type selection in the apparatus is for the benefit of the sleep practitioner and clinical researcher so that the optimum stimuli or sequence of stimuli for the desired response can be selected.

CNS respiration resumption delay is the time difference between stimuli detection to resumption of breathing.

CNS stimulus detection delay is the time difference between stimuli started to arousal.

A detailed description of the Method for Dosage Optimization is provided below and in a separately filed U.S. Provisional Patent Application titled Method for Dosage Optimization in a closed loop neuromodulator, filed on Aug. 22, 2008, the contents of which are hereby incorporated by reference herein.

Stimulus dosage optimization is about constantly monitoring the effect that the presently applied stimulus has on the sleeping patient's CNS and subsequently appropriately adjusting the next stimulus in order to achieve the optimal transfer of energy into the CNS for the sleeping patient at the time when the patient requires apnea therapy without waking the patient or significantly changing the sleep state of the patient.

Patient setup is about learning what the initial stimulus parameters are that result in an optimal transfer of energy into the sleeping patient's CNS.

For the nonprofessionals, the escalation steps change from soft to mild to moderate to strong then harsh.

The method may be used in conjunction with a central nervous system stimulation controller such as that described herein.

Additionally, the method may be applied while using a transducer such as that described in the U.S. Provisional Patent Application titled Agitator to Stimulate the Central Nervous System filed on May 2, 2008, with Ser. No. 61/049,802, the contents of which are hereby incorporated by reference herein.

Additional U.S. Patents hereby incorporated by reference herein include:

| Dymedix Patents Granted | U.S. Pat. No. | Inventor(s) |
| --- | --- | --- |
| Breath Sensing Apparatus | 5,311,875 | Stasz et al. |
| Electronic Temperature/Pressure Transducer | D410.584 | Stasz et al. |
| Electronic Temperature/Pressure Transducer | D417.161 | Stasz et al. |
| Pyro/Piezo Sensor | 6,254,545 | Stasz et al. |
| Pyro/Piezo Sensor with Enhanced Sound Response | 6,485,432 | Stasz et al. |
| Pyro/Piezo Sensor | 6,491,642 | Stasz |
| Snore Sensor | 6,551,256 | Stasz et al. |
| Signal Processing Circuit for Pyro/Piezo Transducer | 6,702,755 | Stasz et al. |
| Nasal Vibration Transducer | 6,894,427 | Alfini |

A patient setup is performed during a first application of stimuli. During the first time use, a closed loop neuromodulator performs a patient setup for patient assessment.

During a first application of stimuli during a first use of the closed loop neuromodulator, the controller starts with the stimulus parameter default settings as stored in the closed loop neuromodulator memory and defined by an attending sleep practitioner and related to the outcome of clinical studies on the patient.

During patient setup, the modulator starts with the lowest energy stimulus and moves towards an optimum selection and setting of stimulus parameters.

During patient setup, the closed loop neuromodulator detects, and records the actual stimulation for each individual patient automatically during first use.

During stimulus level patient setup, the closed loop neuromodulator records and stores the stimulus level value that caused the resumption of normal breathing as a marker. During the next apnea episode, the closed loop neuromodulator uses the stored stimulus level marker and starts the first stimulus level either one or more stimulus levels below the first stimulus level marker value.

During stimulus duration patient setup, the closed loop neuromodulator records and stores the stimulus duration value that caused the resumption of normal breathing as a marker. During the next apnea episode, the closed loop neuromodulator uses the stored stimulus duration marker and starts the first stimulus level either one or more stimulus levels below the first stimulus duration marker value.

During stimulus rate patient setup, the closed loop neuromodulator records and stores the stimulus rate value that caused the resumption of normal breathing as a marker. During the next apnea episode, the closed loop neuromodulator uses the stored stimulus rate marker and starts the first stimulus level either one or more stimulus levels below the first stimulus rate marker value.

During stimulus type patient setup, the closed loop neuromodulator records and stores the stimulus type value that caused the resumption of normal breathing as a marker. During the next apnea episode, the closed loop neuromodulator uses the stored stimulus type marker and starts the first stimulus level either one or more stimulus levels below the first stimulus type marker value.

Stimulus Dosage Optimization

Ideally, the ratio of stimulus generated to sleep disorder events, including apnea events, is above 2 to 1. The rationale for this is that the first stimulus signal should not generate any arousal so that it is established that the signal level is low enough as neither to change the sleeping patients sleep state nor to awake him. Then with that base stimulus level established, the next stimulus level generated should be high enough to cause and arousal in order to cause resumption of breathing. Since the first level was not high enough to cause any cortical arousal and the second level was just slightly above the first level, one can safely assume that the second level was not strong enough to neither change the sleeping patients sleep state nor wake him up completely. This device automatically figures out both levels.

Stimulus dosage Optimizing, constantly measures the ratio between applied stimulus and non-breathing events to monitor that the patient changes neither sleep state nor wakes up due to over stimulation. Furthermore making sure that the patient does not remain in an apnea state due to under stimulation.

During the first stimulus dosage optimization, closed loop neuromodulator continues with the stimulus parameter settings as recorded and stored during the patient setup.

During stimulus dosage optimization, the closed loop neuromodulator detects, and records the actual stimulation for each individual patient automatically during each apnea episode.

During stimulus dosage level optimization, the closed loop neuromodulator recalls the last recorded stimulus level value that caused the resumption of normal breathing as a new marker. During the next apnea episode, the closed loop neuromodulator uses the new stored stimulus level marker and starts the first stimulus level either one or more stimulus levels below the new stimulus level marker value.

During stimulus dosage duration optimization, the closed loop neuromodulator recalls the last recorded stimulus duration value that caused the resumption of normal breathing as a new marker. During the next apnea episode, the closed loop neuromodulator uses the new stored stimulus duration marker and starts the first stimulus level either one or more stimulus levels below the new stimulus duration marker value.

During stimulus dosage rate optimization, the closed loop neuromodulator recalls the last recorded stimulus rate value that caused the resumption of normal breathing as a new marker. During the next apnea episode, the closed loop neuromodulator uses the new stored stimulus rate marker and starts the first stimulus level either one or more stimulus levels below the new stimulus rate marker value.

During stimulus dosage type optimization, the closed loop neuromodulator recalls the last recorded stimulus type value that caused the resumption of normal breathing as a new marker. During the next apnea episode, the closed loop neuromodulator uses the new stored stimulus type marker and starts the first stimulus level either one or more stimulus levels below the new stimulus type marker value.

Figure 19:
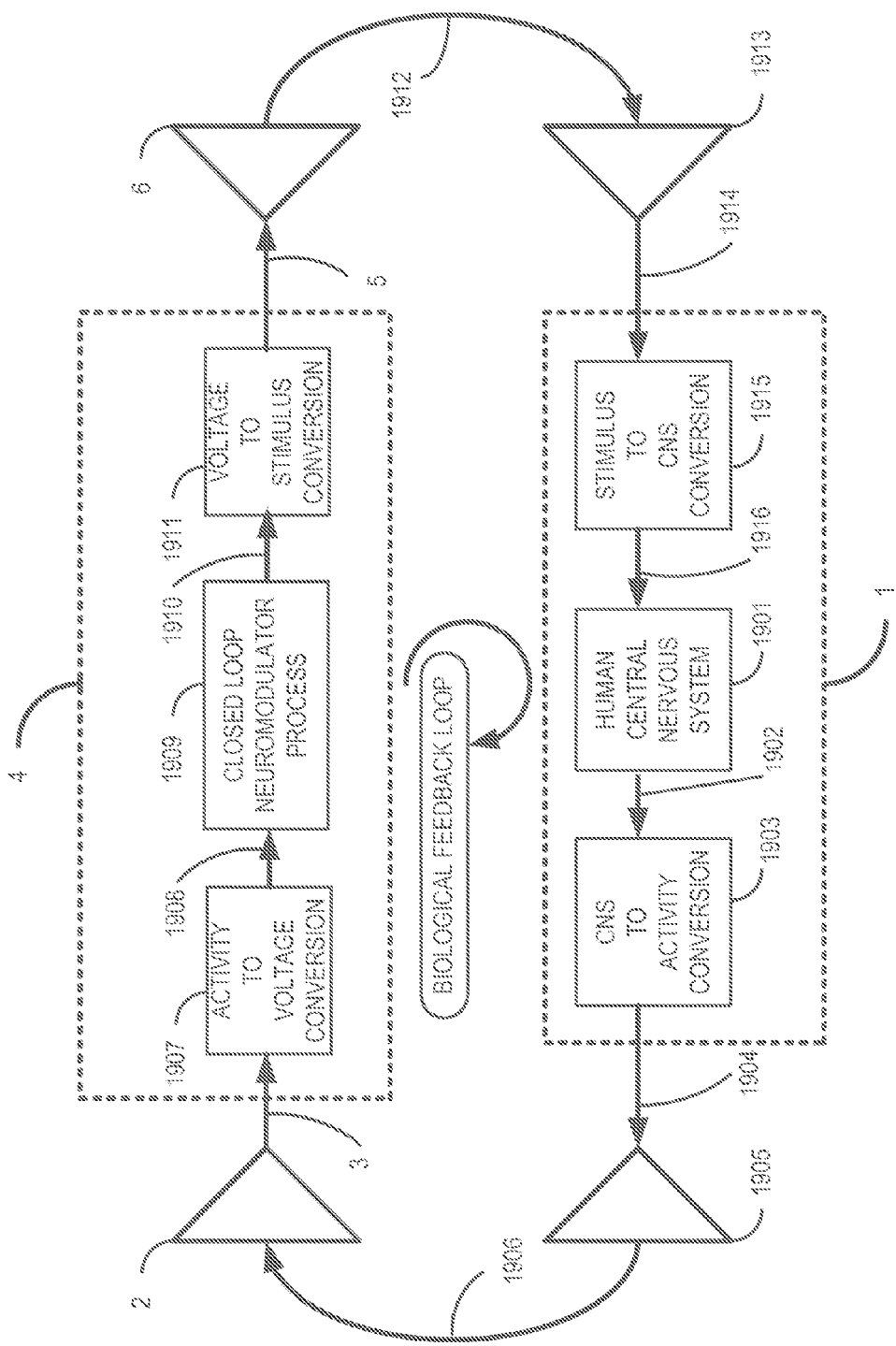
FIG. 19 illustrates generally a diagram depicting a Stimulation Bio-Feedback Loop of a closed loop neuromodulator.

Referring to FIG. 19, there is indicated more specifically by numeral 1 a sleeping patient. The sleeping patient 1 comprises the following elements, a human Central Nervous System (CNS) 1901, a human respiratory CNS pathway 1902 connecting the human CNS 1901 to a respiratory system 1903. The respiratory system 1903 provided a pathway 1904, in this case, human respiration providing airflow to the patient's nose or mouth 1905. The patient's respiratory airflow 1906 is blown across an airflow sensor 2 (for example, but not limited to the one taught in the STASZ U.S. Pat. No. 6,254,545 etc). The airflow sensor 2 connects to the closed loop neuromodulator 4 via a sensor wire pair 3. The closed loop neuromodulator 4 comprises the following elements, an activity to voltage conversion 1907, which connects via connection 1908 to the input of the closed loop neuromodulator process 1909, closed loop neuromodulator process 1909 connects via connection 1910 to the input of the voltage to stimulus conversion 1911. The output of the voltage to stimulus conversion 1911 connects via wire connection 5 to the stimulus transducer 6. Stimulus transducer 6 delivers the closed loop neuromodulator generated stimulus via the biological connection 1912, to one or more of the patient's five senses (taste, smell, touch, sight and/or sound) in this case a sound transducer connected to the patient's outer ear 1913. The patient's outer ear 1913 connects via the patient's inner ear 1914 to the human peripheral nervous system (PNS) 1915. The human peripheral nervous system 1915 connects via the auditory nerve 1916 to the human central nervous system 1901.

Figure 13A:
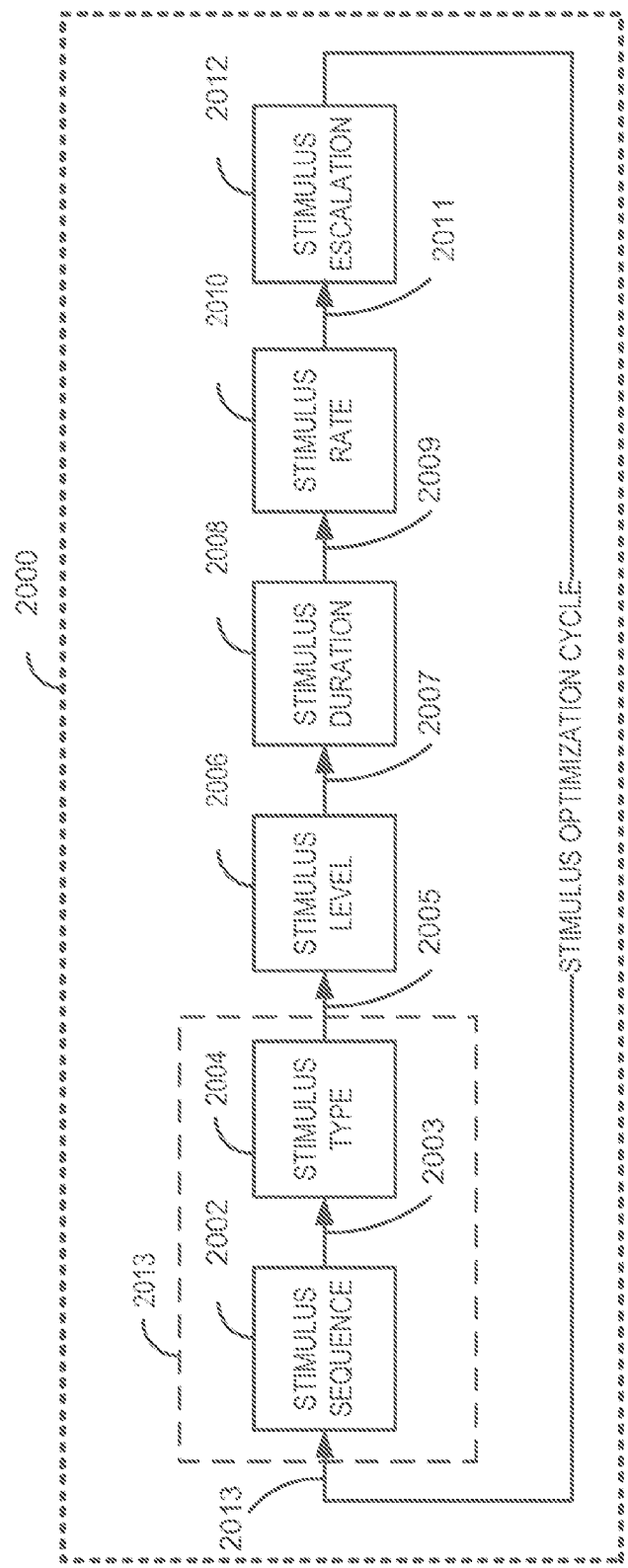
FIG. 13A illustrates generally a diagram depicting the stimulus parameters of a closed loop neuromodulator.

Referring to FIG. 13A, there is indicated more specifically by numeral 2000 the stimulus parameters. First, the stimulus sequence 2002 is selected then optimized. Second, the stimulus type 2004 is selected then optimized. Third, the stimulus type 2004 is selected then optimized. Fourth, the stimulus duration 2008 is selected then optimized. Fifth, the stimulus rate 2010 is selected then optimized. Sixth, the stimulus escalation 2012 is selected then optimized. The cycle completes and continues. This figure points out that this invention makes use of those elements and that this invention is referring to them in the descriptions below. Additionally, as sleep therapy is delivered to a patient and modulated to treat sleep disorder events, in various examples, the closed loop neural modulator changes the stimulus to avoid habituation of the patient to a particular form of stimuli. Anti-habituating sleep therapy, in such embodiments, modulates anti-habituating sleep therapy elements 2013 including stimulus sequence, stimulus type, or combinations thereof, to prevent patient habituation. In one example, anti-habituating sleep therapy monitors average energy levels of delivered therapy stimuli and modulates the therapy to avoid habituation if the average energy exceeds a threshold. In some examples, therapy is modulated after a predetermined time interval to avoid habituation. It is understood that other anti-habituating sleep therapy methods are possible without departing from the scope of the present subject matter.

Figure 13B:
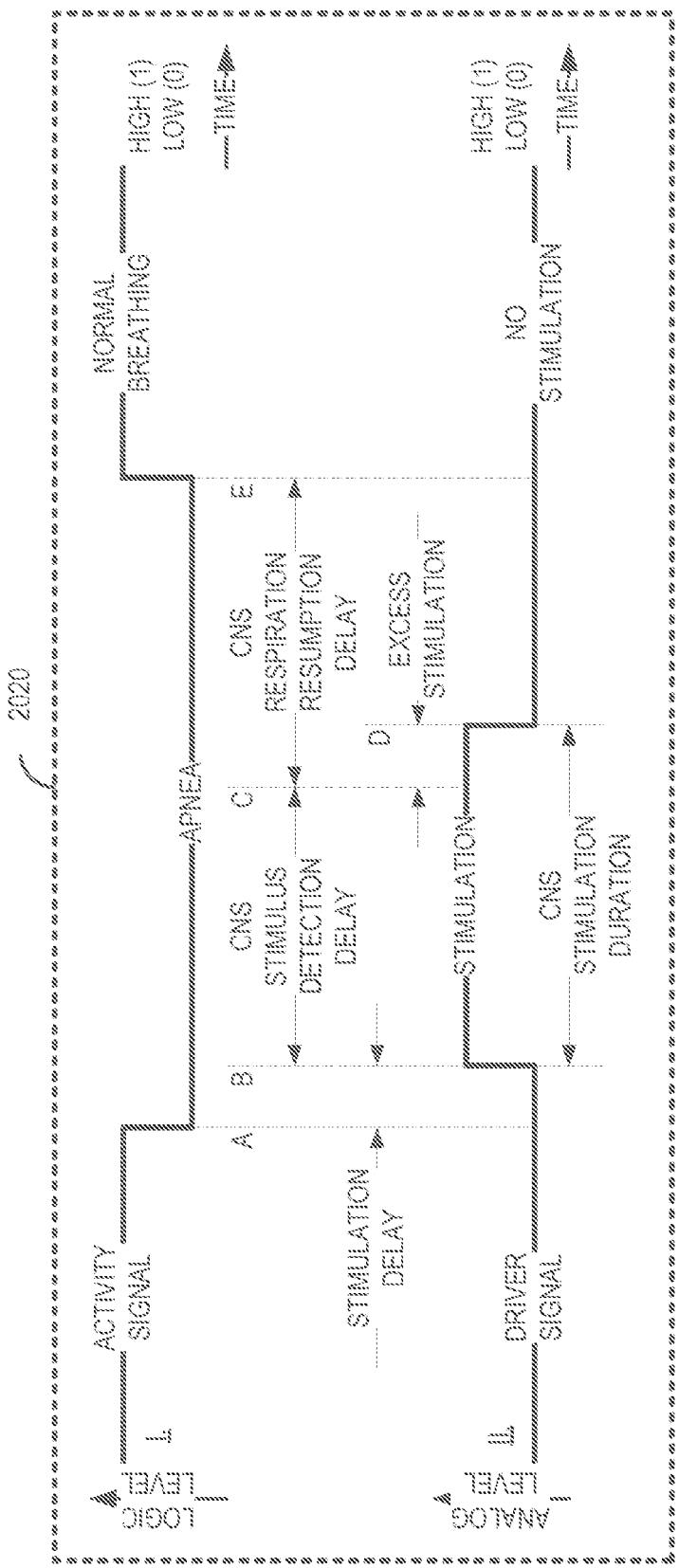
FIG. 13B illustrates generally a timing diagram depicting stimulation timing.

Referring to FIG. 13B, there is indicated more specifically by numeral 2020 a diagram of general stimulation timing. There is indicated by roman numeral I. an activity signal of a closed loop neuromodulator. The activity signal is represented by a logic level signal. The logic levels may take on either a logic high state ("1") or a logic low state ("0"). The high state indicates "normal breathing" which means that the patient is not currently experiencing a breathing disorder. The low state indicates "Apnea" which means that the patient is currently experiencing a breathing disorder. There is indicated by Roman numeral II. a driver signal of a closed loop neuromodulator. The driver signal is represented by an analog level signal. The analog levels may take on any level value between a lowest level and a highest level. The lowest and the highest level are determined by the specific embodiment of the apparatus. The absence of a signal indicates "no stimulation". No stimulation means that the patient is currently not subjected to a CNS stimulus signal. The presence of a signal indicates "stimulation". Stimulation means that the patient is currently subjected to a CNS stimulus signal. Letter A indicates the falling edge of the activity signal indicating a change from the patient normal breathing level to the apnea level. In response to the activity signal going low, the apparatus inserts a stimulation delay lasting from letter A to letter B to allow for internal processing delays and internal device set-up times. Letter B indicates the start of the actual stimulus driver signal as it is being sent to the patient. Letter C indicates the point where the patient's central nervous system detects the presence of the stimulus signal. At this time the stimulus could stop, however, the apparatus has no knowledge or information that the patient just detected the stimulus signal, thus the stimulus signal continues for another duration that is indicated as the excess stimulation. It is also a goal of this invention to minimize the excess stimulation duration in order to minimize over stimulation through excess stimulus duration. Letter D indicates the end of the stimulus signal as it is being sent to the patient. The time between C and E is the time it takes the patient's CNS to detect, realize and act upon the received stimulus. In this case, the detection of the stimulus at point C is triggering the resumption of breathing at point E. The time between A and B is the apparatus internal stimulation delay. The time between B and D is the apparatus controlled stimulation duration. The time between D and E is the time between the end of stimulation till the time of respiration resumption. The time between B and C is patient dependent and represents the CNS stimulus detection delay. The time between C and E is patient dependent and represent the CNS respiration resumption delay.

Figure 14A:
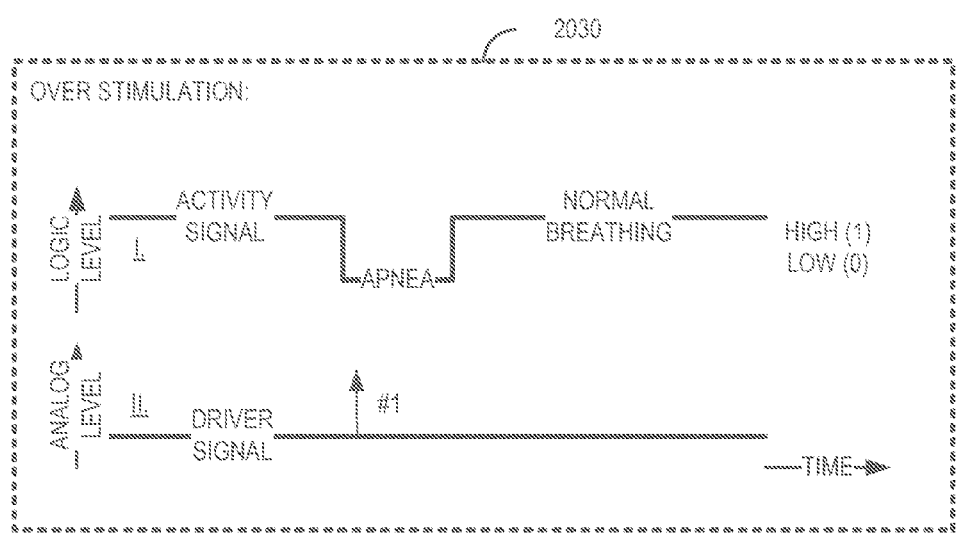
FIG. 14A illustrates generally a timing diagram depicting over stimulation.

Referring to FIG. 14A, there is indicated more specifically by numeral 2030 a diagram of a stimulation optimization, more specifically the situation of patient CNS overstimulation. There is indicated by Roman numeral I. an activity signal of a closed loop neuromodulator. The activity signal is represented by a logic level signal. The logic levels may take on either a logic high state ("1") or a logic low state ("0"). The high state indicates "normal breathing" which means that the patient is not currently experiencing a breathing disorder. The low state indicates "Apnea" which means that the patient is currently experiencing a breathing disorder. There is indicated by Roman numeral II. a driver signal of a closed loop neuromodulator. The driver signal is represented by an analog level signal #1. The analog levels may take on any level value between a lowest level and a highest level. The lowest and the highest level are determined by the specific embodiment of the apparatus. The absence of a signal indicates "no stimulation". No stimulation means that the patient is currently not subjected to a CNS stimulus signal. The presence of a signal indicates "stimulation". Stimulation means that the patient is currently subjected to a CNS stimulus signal.

Shortly after the activity signal changes from the normal breathing state to the apnea state, the driver signal issues a stimulus signal #1. Shortly after the apparatus has issued the stimulus signal #1, the apparatus has issued the activity signal changes state from apnea to normal breathing, meaning that the patient has started to resume normal respiration shortly after the first stimulus signal. This is not quite a desirable situation because it is safe to assume that this stimulus signal was simply too strong and it aroused the CNS more dramatically than desired and cause the patient most likely to wake up and in a lesser case, change sleep states and resume breathing. The key point of this invention is to neither wake the patient nor make him or her change sleep states significantly. When the second stimulus after the detection of an apnea caused this effect than according to this invention, the patient has been optimally stimulated.

Figure 14B:
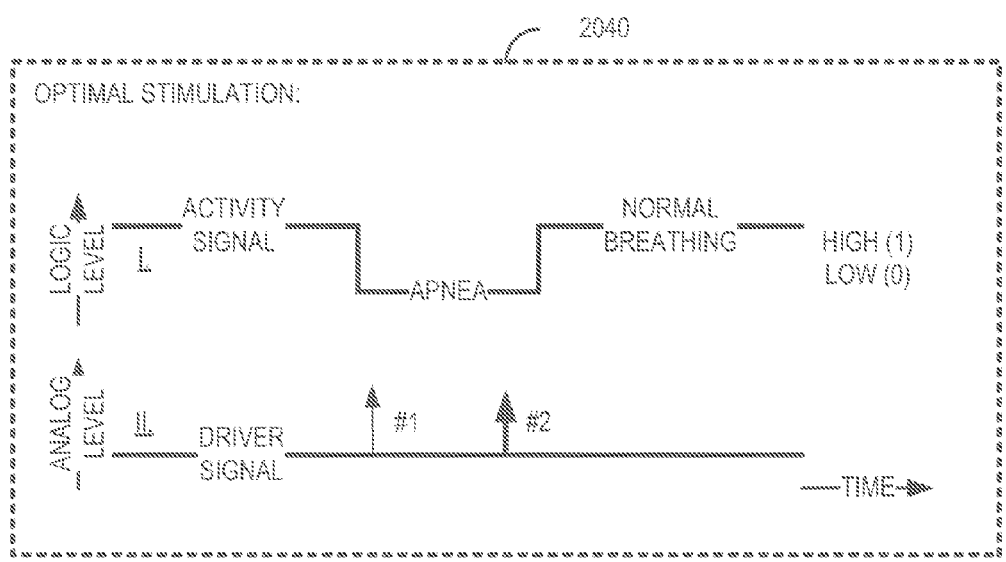
FIG. 14B illustrates generally a timing diagram depicting optimal stimulation.

Referring to FIG. 14B, there is indicated more specifically by numeral 2040 a diagram of a stimulation optimization, more specifically the situation of patient optimal CNS stimulation. There is indicated by Roman numeral I. an activity signal of a closed loop neuromodulator. The activity signal is represented by a logic level signal. The logic levels may take on either a logic high state ("1") or a logic low state ("0"). The high state indicates "normal breathing" which means that the patient is not currently experiencing a breathing disorder. The low state indicates "Apnea" which means that the patient is currently experiencing a breathing disorder. There is indicated by Roman numeral II. a driver signal of a closed loop neuromodulator. The driver signal is represented by an analog level signal #1. The analog levels may take on any level value between a lowest level and a highest level. The lowest and the highest level are determined by the specific embodiment of the apparatus. The absence of a signal indicates "no stimulation". No stimulation means that the patient is currently not subjected to a CNS stimulus signal. The presence of a signal indicates "stimulation". Stimulation means that the patient is currently subjected to a CNS stimulus signal.

Shortly after the activity signal changes from the normal breathing state to the apnea state, the driver signal issues a stimulus signal #1. Since after a short while stimulus signal #1 has not caused the resumption of breathing, a second stimulus signal #2 issues. Since the first stimulus signal has not caused the respiration to resume, one can safely assume that the patient neither woke up nor did patient change sleep states, nor did the first stimulus cause a significant CNS arousal. Shortly after the second stimulus signal #2 issues, the activity signal changes state from apnea to normal breathing, indicating that the patient has started to resume normal respiration shortly after the second stimulus signal has been issued by the apparatus. This is a desirable situation because it is safe to assume that the second stimulus was of adequate strength to cause the patient to breathe again. Is also safe to assume since the first stimulus signal was not strong enough to cause the resumption of breathing and neither woke the patient nor caused the patient to change sleep state, that the second stimulus, which was just slightly stronger, did also not wake nor significantly changed the patients sleep states. The second stimulus #2 was dosed optimally in order to cause the patient to resume breathing after the first stimulus showed no effect. The key point of this invention is to neither wake nor make the patient change sleep states significantly. When the second stimulus after the detection of an apnea caused this effect than according to this invention, the patient has been optimally stimulated.

Figure 14C:
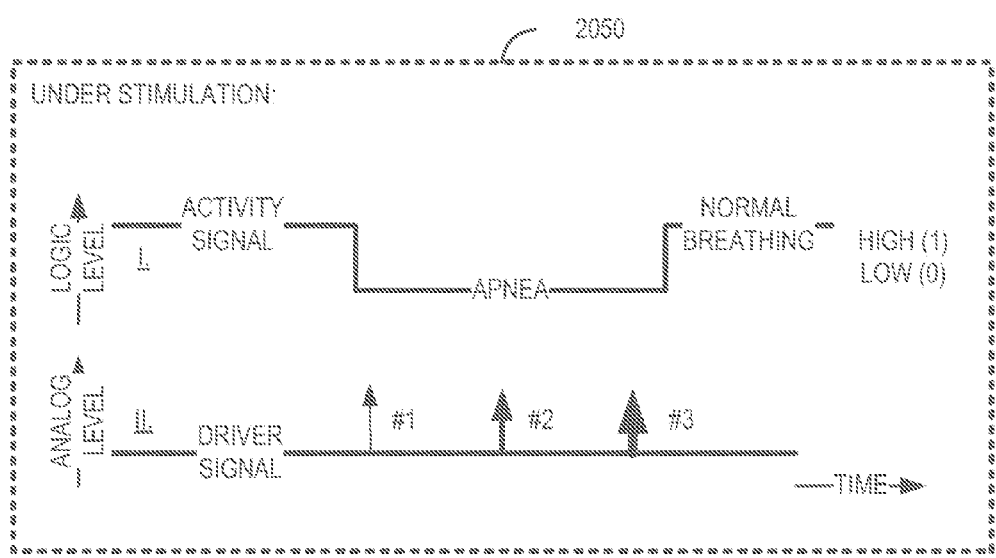
FIG. 14C illustrates generally a timing diagram depicting under stimulation.

Referring to FIG. 14C, there is indicated more specifically by numeral 2050 a diagram of a CNS stimulation optimization, more specifically the situation of patient CNS under stimulation. There is indicated by Roman numeral I. an activity signal of a closed loop neuromodulator. The activity signal is represented by a logic level signal. The logic levels may take on either a logic high state ("1") or a logic low state ("0"). The high state indicates "normal breathing" which means that the patient is not currently experiencing a breathing disorder. The low state indicates "Apnea" which means that the patient is currently experiencing a breathing disorder. There is indicated by Roman numeral II. a driver signal of a closed loop neuromodulator. The driver signal is represented by an analog level signal #1. The analog levels may take on any level value between a lowest level and a highest level. The lowest and the highest level are determined by the specific embodiment of the apparatus. The absence of a signal indicates "no stimulation". No stimulation means that the patient is currently not subjected to a CNS stimulus signal. The presence of a signal indicates "stimulation". Stimulation means that the patient is currently subjected to a CNS stimulus signal.

Shortly after the activity signal changes from the normal breathing state to the apnea state, the driver signal issues a stimulus signal #1. Since after a short while stimulus signal #1 has not caused the resumption of breathing, a second stimulus signal #2 issues. Since the first stimulus signal has not caused the respiration to resume, one can safely assume that the patient neither woke up nor did patient change sleep states, nor did the first stimulus cause a significant CNS arousal.

Shortly after the second stimulus signal #2 issues, the activity signal still does not change state from apnea to normal breathing, indicating that the patient has not yet started to resume normal respiration shortly after the second stimulus signal has been issued by the apparatus. This is also not a desirable situation because it has not caused the patient to resume breathing. It is safe to assume that the second stimulus was also not of adequate strength to cause the patient to breathe again. It is also safe to assume since the first stimulus signal was not strong enough to cause the resumption of breathing and neither woke the patient nor caused the patient to change sleep state, that the second stimulus, which was just slightly stronger, did also not wake nor significantly changed the patients sleep states.

The third stimulus #3 was dosed properly but not optimally, even though it caused the patient to resume. The key point of this invention is to neither wake nor make the patient change sleep states significantly but cause the speedy safe resumption of breathing soon after an apnea event has been detected. When the third stimulus after the detection of an apnea caused the patient to breathe than according to this invention, the patient has been under stimulated.

A goal of this invention to attempt to maintain an optimal stimulus dosage, which neither wakes the patient nor causes the patient to change sleep states and to optimally dose the individual stimulus accordingly. The method employed to obtain this goal is to constantly monitor and keep track of the effectiveness of patient stimulation. If the patient resumes breathing after the first stimulus then the next time the patient experiences an apnea, the first stimulus will be issued with significantly less strength. Strength is defined as the amount of energy contained within the applied stimulus. A first stimulus with significantly reduced strength should not cause the patient to resume breathing because this would indicate that the stimulus was strong enough to cause so much CNS stimulation that the patient either woke up or the patient experienced a significant change in sleep state. This method is being repeated until the first stimulus issued after the detection of an apnea does not cause the resumption of breathing in a patient. It can thus be safely assumed that if the second stimulus is just slightly higher and causes the resumption of breathing that the second stimulus was dosed optimally. Furthermore, that if the second stimulus does neither cause resumption of breathing and that the third stimulus which is also slightly stronger than the third causes the resumption of breathing, that the first stimulus issued shortly after the next detection of an apnea is less in strength than the third stimulus that was applied in the previous apnea.

Figure 15A:
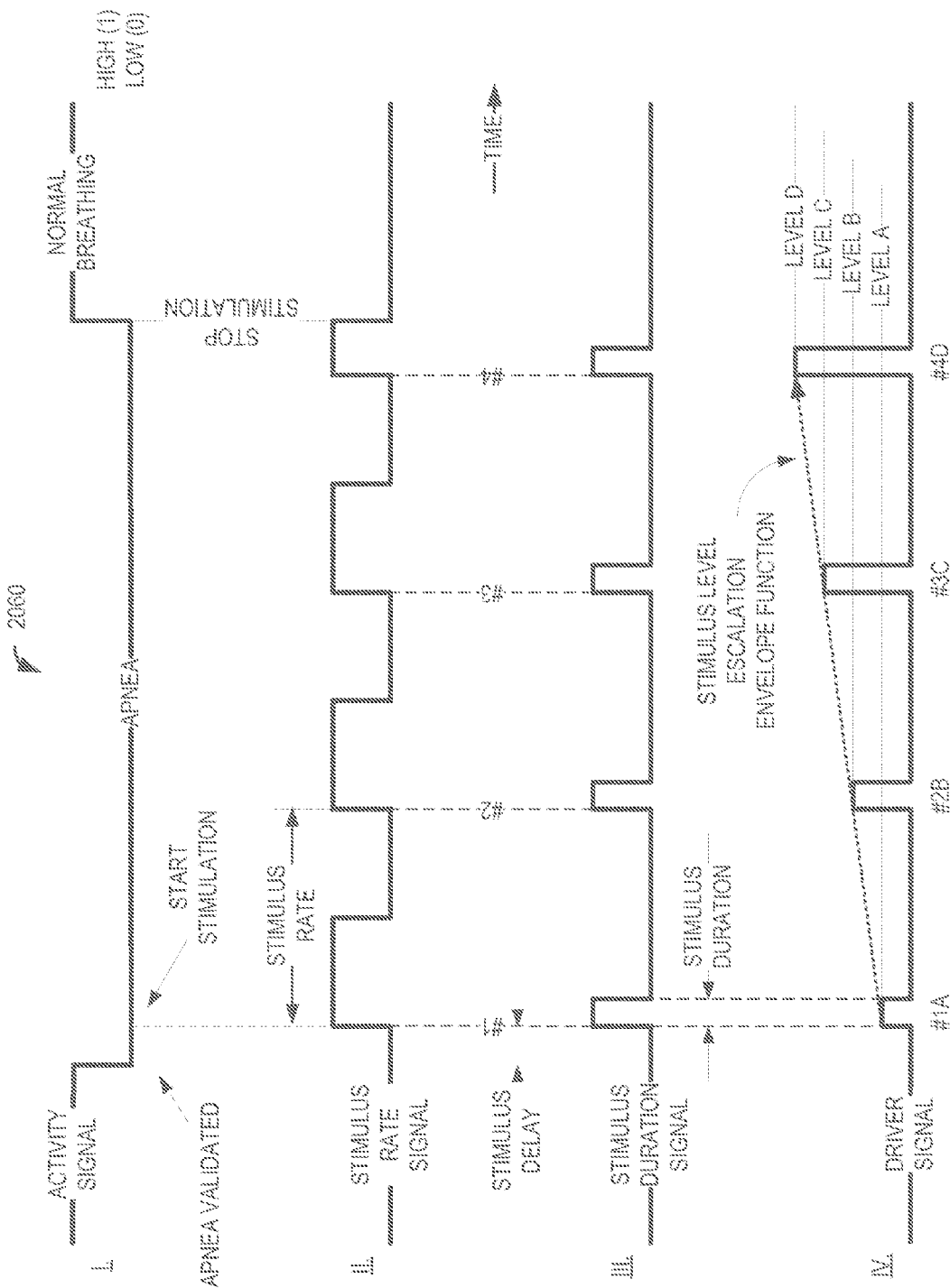
FIG. 15A illustrates generally a timing diagram depicting stimulus escalation without repeats of the previous stimulus.

Referring to FIG. 15A, there is indicated more specifically by numeral 2060 a diagram of a CNS stimulation application.

There is indicated by Roman numeral I. an activity signal of a closed loop neuromodulator. The activity signal is represented by a logic level signal. The logic levels may take on either a logic high state ("1") or a logic low state ("0"). The high state indicates "normal breathing" which means that the patient is not currently experiencing a breathing disorder. The low state indicates "Apnea" which means that the patient is currently experiencing a breathing disorder.

There is indicated by Roman numeral II. a stimulus rate signal of a closed loop neuromodulator. The stimulus rate signal is represented by a logic level signal. The logic levels may take on either a logic high state ("1") or a logic low state ("0"). The stimulation signal rate may be adjusted either manually by the sleep professional or automatically by the apparatus (e.g. as instructed or required by the CNS stimulation optimization method). Shortly after the activity signal changes from the normal breathing state to the apnea state, the stimulus rate signal changes state from a logic low to a logic high after the stimulus delay period, which may also be adjusted either manually by the sleep professional or automatically by the apparatus (e.g. as instructed or required by the CNS stimulation optimization method). The change of signal state from low to high of the stimulus rate signal indicates the start of a stimulus signal. The stimulus rate signal remains active and keeps on changing states indicating the need for continuously issuing CNS stimulus to the patient until normal breathing has resumed.

There is indicated by Roman numeral III. a stimulus duration signal of a closed loop neuromodulator. The stimulus duration signal is represented by a logic level signal. The logic levels may take on either a logic high state ("1") or a logic low state ("0"). The stimulus duration may be adjusted by either manually by the sleep professional or automatically by the apparatus (e.g. as instructed or required by the CNS stimulation optimization method). As soon as the stimulus rate signal II. changes state from low to high, the stimulus duration signal goes high (active) for the specific duration of the presently applied CNS stimulus. The stimulus duration signal remains active and keeps on changing states indicating the need for continuously issuing CNS stimulus to the patient until normal breathing has resumed.

There is indicated by Roman numeral IV. a driver signal of a closed loop neuromodulator. The driver signal is represented by an analog level signal #1. The analog levels may take on any level value between a lowest level and a highest level. The CNS stimulation level may be adjusted either manually by the sleep professional or automatically by the apparatus (e.g. as instructed or required by the CNS stimulation optimization method). The absence of a signal indicates "no stimulation". No stimulation means that the patient is currently not subjected to a CNS stimulus signal. The presence of a signal indicates "stimulation". Stimulation means that the patient is currently subjected to a CNS stimulus signal. The first CNS stimulus issued by the driver signal IV. after the activity signal transitions from high to low indicating an apnea is indicated by numeral #1A. The numeral indicates that this is the first (1) stimulus (#) of this apnea of stimulus level A (A). The selection of which stimulus level is to be issued shortly after an apnea has been detected may be may be controlled either manually by the sleep professional or automatically by the apparatus (e.g. as instructed or required by the CNS stimulation optimization method). In this case, the stimulus selected is of the lowest level (aka; strength, volume, loudness). After the first stimulus dosage has been issued to the patient's CNS, the apparatus waits for a certain CNS stimulation dwell time that is dependent on the stimulus rate and stimulus duration. After the stimulation dwell time has expired, a new stimulus will be issued unless the activity signal transitions from low to high indicating that normal breathing has resumed and that no more stimulus are required.

If normal breathing has not resumed after issuing first stimulus #1A then the apparatus may issue second stimulus #2B of stimulus level B. According to this invention, this stimulus may be of a different type, may be of a different level, may be of a different rate, or may be of a different duration. In this example, only a different level is indicated. A higher stimulus level delivers more energy into the CNS and it is assumed that a higher stimulus level causes a stronger response from the CNS. It is hoped in this case that following the arousal of the patient's CNS by the detection of the presently applied stimulus will cause the resumption of breathing.

If normal breathing has not resumed after issuing second stimulus #2B then a third the apparatus may issue stimulus #3C of stimulus level C. The apparatus will again monitor for the resumption of the desired patient activity or the cessation of the undesired patient activity.

If normal breathing has not resumed after issuing third stimulus #3C then a fourth stimulus #4D of stimulus level the apparatus may issue D. The apparatus constantly monitors for the resumption of the desired patient activity or the cessation of the undesired patient activity.

In this case, CNS stimulus #4D was successful in causing the resumption of the patient's desired activity (breathing) indicated by the low to high transition of the activity signal.

After the patient has resumed the desired activity/normal, breathing the apparatus will issue no further CNS stimulus until the activity signal transitions from high to low again indicating a detection of a sleep apnea or any other undesired behavior that can be controlled by controlled stimulation of the CNS.

Figure 15B:
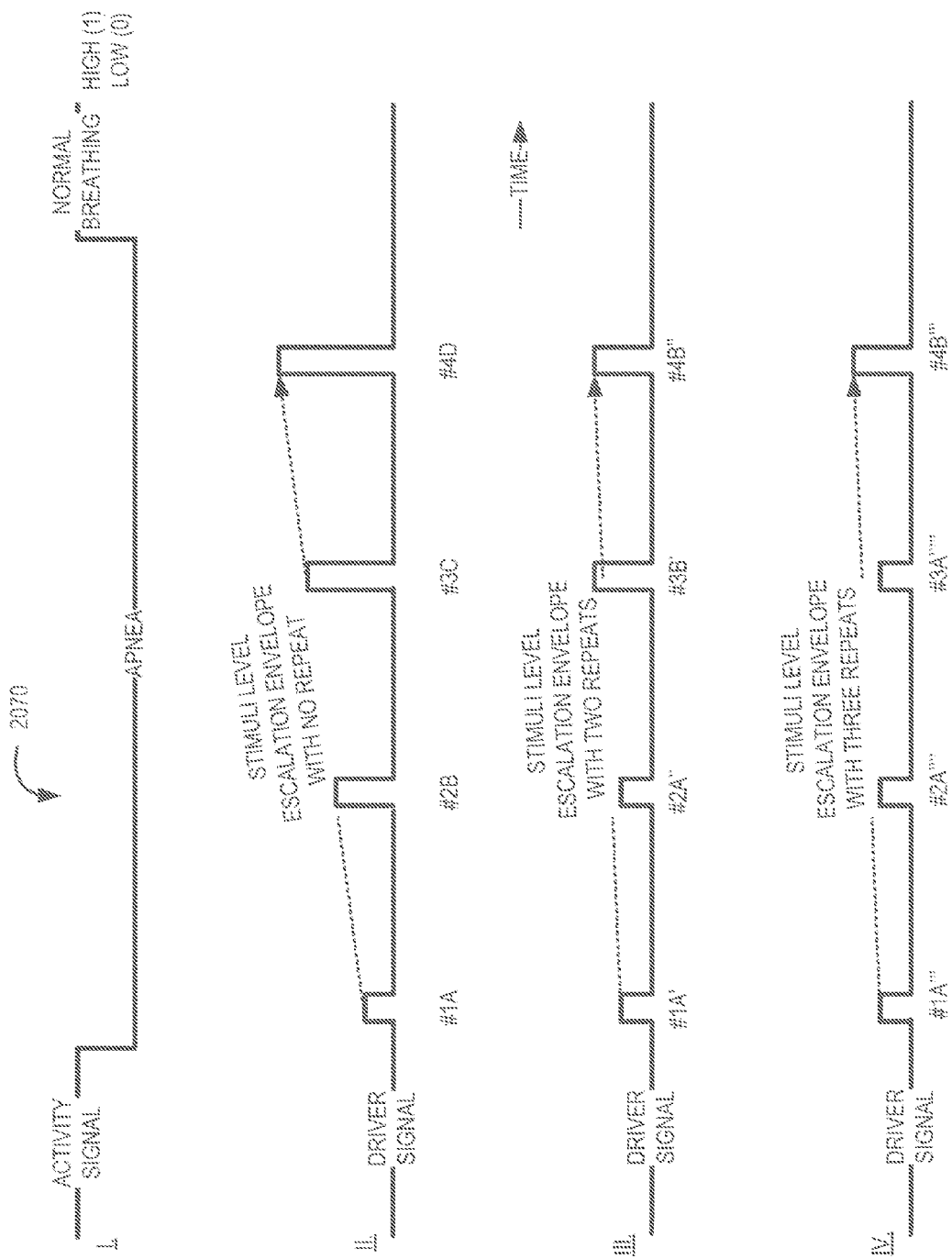
FIG. 15B illustrates generally a timing diagram depicting stimulus escalation with repeats of the previous stimulus.

Referring to FIG. 15B, there is indicated more specifically by numeral 2070 a diagram of a CNS stimulus escalation method.

There is indicated by Roman numeral I. an activity signal of a closed loop neuromodulator. The activity signal is represented by a logic level signal. The logic levels may take on either a logic high state ("1") or a logic low state ("0"). The high state indicates "normal breathing" which means that the patient is not currently experiencing a breathing disorder. The low state indicates "Apnea" which means that the patient is currently experiencing a breathing disorder.

There is indicated by Roman numeral II. a driver signal of a closed loop neuromodulator. The driver signal is represented by an analog level signal. The analog levels may take on any level value if instructed to do so between a lowest level and a highest level. In this case, the first stimulus being issued after a short delay in response to apnea detection is #1A. Stimulus #1A may be of any type, level, duration or rate. If stimulus #1A does not cause the resumption of normal breathing then after a certain amount of time that is dependent on the specific stimulus rate, second stimulus #2B is being issued. Since the first stimulus #1A did not produce the desire result, the level for stimulus #2B has been increased by a specific amount, which depends on the type of level escalation envelope function. In this case, the level escalation envelope function is linear. This means the each next stimulus level increases with the same factor as the one before. Other level stimulus escalation envelope functions are possible as discussed in the Stimulus Escalator section included herein. If stimulus #2B does not cause the resumption of normal breathing then after a certain amount of time that is dependent on the specific stimulus rate, a third stimulus #3C is being issued. Since the second stimulus #2B did not produce the desire result, the level for stimulus #3C has been increased by a specific amount, which depends on the type of level escalation envelope function. If stimulus #3C does not cause the resumption of normal breathing then after a certain amount of time that is dependent on the specific stimulus rate, a fourth stimulus #4D is being issued. Since the third stimulus #3C did not produce the desire result, the level for stimulus #4D has been increased by a specific amount which depends on the type of level escalation envelope function. This pattern of issuing ever changing and increasing stimulus types, levels, durations and rates continues until normal breathing has been detected.

There is indicated by Roman numeral III. a driver signal of a closed loop neuromodulator. The driver signal is represented by an analog level signal. The analog levels may take on any level value if instructed to do so between a lowest level and a highest level. In this case, the first stimulus being issued after a short delay in response to apnea detection is #1A'. Stimulus #1A' may be of any type, level, duration or rate and stimulus #1A' does not have to be the same as stimulus #1A. If stimulus #1A' does not cause the resumption of normal breathing then after a certain amount of time that is dependent on the specific stimulus rate, a second stimulus #2A" is being issued. Since the first stimulus #1A' did not produce the desire result, the type, duration or rate for stimulus #2A" has been changed by a specific amount which depends on the type of level escalation envelope function, however, the level has not been increased this time. Either in this case the escalation envelope function is defined as a type, duration or rate change and the envelope function may be linear or take on any other mathematical function including a randomization. This means the each next stimulus is different from the one before. Other stimulus escalation envelope functions are possible as discussed in the Stimulus Escalator section and the Stimulus Sequencer section included herein. If stimulus #2A" does not cause the resumption of normal breathing then after a certain amount of time that is dependent on the specific stimulus rate, a third stimulus #3B' is being issued. Since the second stimulus #2A" did not produce the desire result, the type, duration or rate for stimulus #3B' has been changed by a specific amount which depends on the type of escalation envelope function. If stimulus #3B' does not cause the resumption of normal breathing then after a certain amount of time that is dependent on the specific stimulus rate, a fourth stimulus #4B" is being issued. Since the third stimulus #3B' did not produce the desired result, the level for stimulus #4B" has been increased by a specific amount which depends on the type of escalation envelope function. This pattern of issuing ever changing and increasing stimulus types, levels, durations and rates continues until normal breathing has been detected. It shall be noted that the same level has been repeated twice in this sequence of stimulus delivery.

There is indicated by Roman numeral IV. a driver signal of a closed loop neuromodulator. The driver signal is represented by an analog level signal. The analog levels may take on any level value if instructed to do so between a lowest level and a highest level. In this case, the first stimulus being issued after a short delay in response to an apnea detection is #1A'''. Stimulus #1A''' may be of any type, level, duration or rate. If stimulus #1A''' does not cause the resumption of normal breathing then after a certain amount of time that is dependent on the specific stimulus rate, a second stimulus #2A'''' is being issued. Since the first stimulus #1A''' did not produce the desire result, the type, duration or rate for stimulus #2A'''' has been changed by a specific amount which depends on the type of level escalation envelope function, however, the level has not been increased this time. Either in this case the escalation envelope function is defined as a type, duration or rate change and the envelope function may be linear or take on any other mathematical function including a randomization. This means the each next stimulus is different from the one before. Other stimulus escalation envelope functions are possible as discussed in the Stimulus Escalator section included herein. If stimulus #2A"" does not cause the resumption of normal breathing then after a certain amount of time that is dependent on the specific stimulus rate, a third stimulus #3A""' is being issued. Since the second stimulus #2A"" did not produce the desire result, the type, duration or rate for stimulus #3A""' has been changed by a specific amount, which depends on the type of escalation envelope function. If stimulus #3A""' does not cause the resumption of normal breathing then after a certain amount of time that is dependent on the specific stimulus rate, a fourth stimulus #4B''' is being issued. Since the third stimulus #3A""' did not produce the desired result, the level for stimulus #4B''' has been increased by a specific amount which depends on the type of escalation envelope function. This pattern of issuing ever changing and increasing stimulus types, levels, durations and rates continues until normal breathing has been detected. It shall be noted that the same level has been repeated three times in this sequence of stimulus delivery.

Figure 16A:
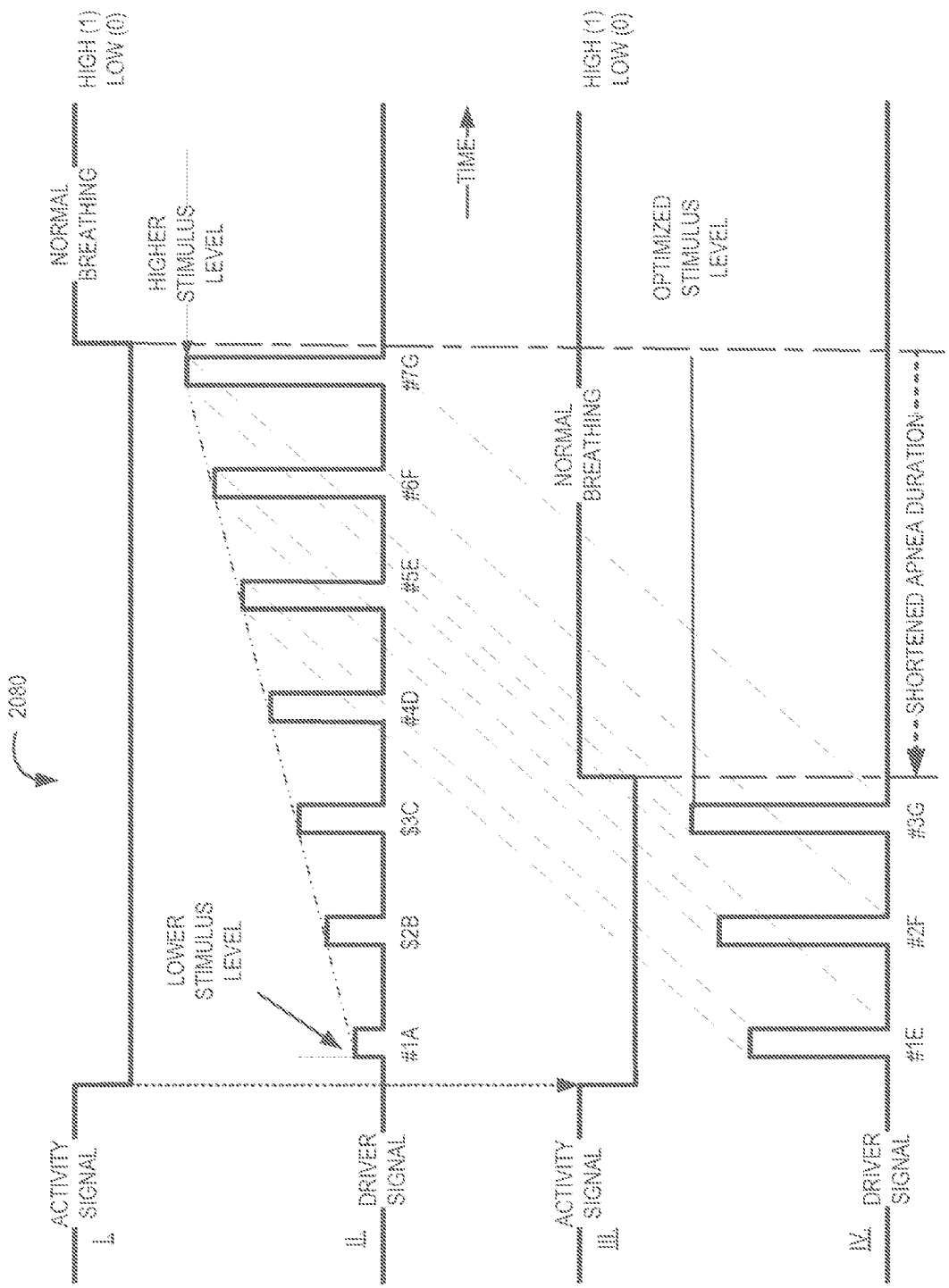
FIG. 16A illustrates generally a diagram depicting stimulus level optimization.

Referring to FIG. 16A, there is indicated more specifically by numeral 2080 a diagram of a CNS stimulus level optimization method.

There is indicated by Roman numeral I. an activity signal of a closed loop neuromodulator depicting non-optimized apnea duration at time interval T. The activity signal is represented by a logic level signal. The logic levels may take on either a logic high state ("1") or a logic low state ("0"). The high state indicates "normal breathing" which means that the patient is not currently experiencing a breathing disorder. The low state indicates "Apnea" which means that the patient is currently experiencing a breathing disorder.

There is indicated by Roman numeral II. A driver signal of a closed loop neuromodulator. The driver signal is represented by an analog level signal. The analog levels may take on any level value if instructed to do so between a lowest level and a highest level. In this case, the first stimulus being issued after a short delay in response to apnea detection is the lowest stimulus level possible #1A. Stimulus #1A may be of any type, duration or rate. If stimulus #1A does not cause the resumption of normal breathing then after a certain amount of time that is dependent on the specific stimulus rate, second stimulus #2B is being issued. Since the first stimulus #1A did not produce the desired result, the level for stimulus #2B has been increased by a specific amount, which depends on the type of level escalation envelope function. In this case, for sake of simplicity, the level escalation envelope function has been chosen to be linear. This means the next stimulus level increases with the same factor as the one before. Other level stimulus escalation envelope functions are possible as discussed in the Stimulus Escalator section included herein. If stimulus #2B does not cause the resumption of normal breathing then after a certain amount of time that is dependent on the specific stimulus rate, a third stimulus #3C is being issued. Since the second stimulus #2B did not produce the desire result, the level for stimulus #3C has been increased by a specific amount, which depends on the type of level escalation envelope function.

If stimulus #3C does not cause the resumption of normal breathing then after a certain amount of time that is dependent on the specific stimulus rate, a fourth stimulus #4D is being issued. Since the third stimulus #3C did not produce the desire result, the level for stimulus #4D has been increased by a specific amount which depends on the type of level escalation envelope function.

If stimulus #4D does not cause the resumption of normal breathing then after a certain amount of time that is dependent on the specific stimulus rate, a fifth stimulus #5E is being issued. Since the fourth stimulus #4D did not produce the desire result, the level for stimulus #5E has been increased by a specific amount, which depends on the type of level escalation envelope function.

If stimulus #5E does not cause the resumption of normal breathing then after a certain amount of time that is dependent on the specific stimulus rate, a sixth stimulus #6F is being issued. Since the fifth stimulus #5E did not produce the desire result, the level for stimulus #6F has been increased by a specific amount, which depends on the type of level escalation envelope function.

If stimulus #6F does not cause the resumption of normal breathing then after a certain amount of time that is dependent on the specific stimulus rate, a seventh stimulus #7G is being issued. Since the sixth stimulus #6F did not produce the desire result, the level for stimulus #7G has been increased by a specific amount which depends on the type of level escalation envelope function.

It shall be noted that the seventh stimulus in this case #7G has caused the resumption of normal breathing in the sleeping patient. At this point, the method instructs the apparatus to store the value of the level that caused the resumption of breathing in memory. This value shall be used as a marker so that the first stimulus level the closed loop neuromodulator selects and issues after detection of the next apnea episode is at least one or more escalation levels below the level that caused the resumption of breathing during the previous apnea episode experienced by the patient. In this special case stimulus level #G was the one that caused the resumption of normal breathing, thus the first level that shall be issued when the next apnea episode occurs is stimulus level #E.

There is indicated by Roman numeral III. an activity signal of a closed loop neuromodulator depicting an optimized apnea duration at time interval T+1 indicating the next apnea episode following the apnea episode duration at the time interval T. The activity signal is represented by a logic level signal. The logic levels may take on either a logic high state ("1") or a logic low state ("0"). The high state indicates "normal breathing" which means that the patient is not currently experiencing a breathing disorder. The low state indicates "Apnea" which means that the patient is currently experiencing a breathing disorder.

There is indicated by Roman numeral VI. A driver signal of a closed loop neuromodulator. The driver signal is represented by an analog level signal. The analog levels may take on any level value if instructed to do so between a lowest level and a highest level. In this case, the first stimulus being issued after a short delay in response to the next apnea detection is the third level down from the level during the previous apnea that caused the resumption of normal breathing in the sleeping patient stimulus level #1E. Stimulus #1E is preferably of the same type, duration or rate but may be of any type, duration or rate. If stimulus #1E does not cause the resumption of normal breathing then after a certain amount of time that is dependent on the specific stimulus rate, a second stimulus #2F is being issued. Since the first stimulus #1E did not produce the desired result, the level for stimulus #2F has been increased by a specific amount, which depends on the type of level escalation envelope function. In this case, for sake of simplicity, the level escalation envelope function has been chosen to be linear. This means the next stimulus level increases with the same factor as the one before. Other level stimulus escalation envelope functions are possible as discussed in the Stimulus Escalator section included herein. If stimulus #2F does not cause the resumption of normal breathing then after a certain amount of time that is dependent on the specific stimulus rate, a third stimulus #3G is being issued. Since the second stimulus #2F did not produce the desire result, the level for stimulus #3G has been increased by a specific amount which depends on the type of level escalation envelope function.

It shall be noted that the third stimulus this time #3G has caused the resumption of normal breathing in the sleeping patient. At this point, again, the method instructs the apparatus to store the value of the level that caused the resumption of breathing in memory. This value shall be used as a marker so that the first stimulus level the closed loop neuromodulator selects and issues after detection of the next apnea episode is at least one or more escalation levels below the level that caused the resumption of breathing during the previous apnea episode experienced by the patient. In this special case stimulus level #G was the one that caused the resumption of normal breathing, thus the first level that shall be issued when the next apnea episode occurs is stimulus level #E.

The method changing stimuli and patterns of issuing more energy containing stimulus types, levels, durations and rates continues until normal breathing has been detected.

Figure 16B:
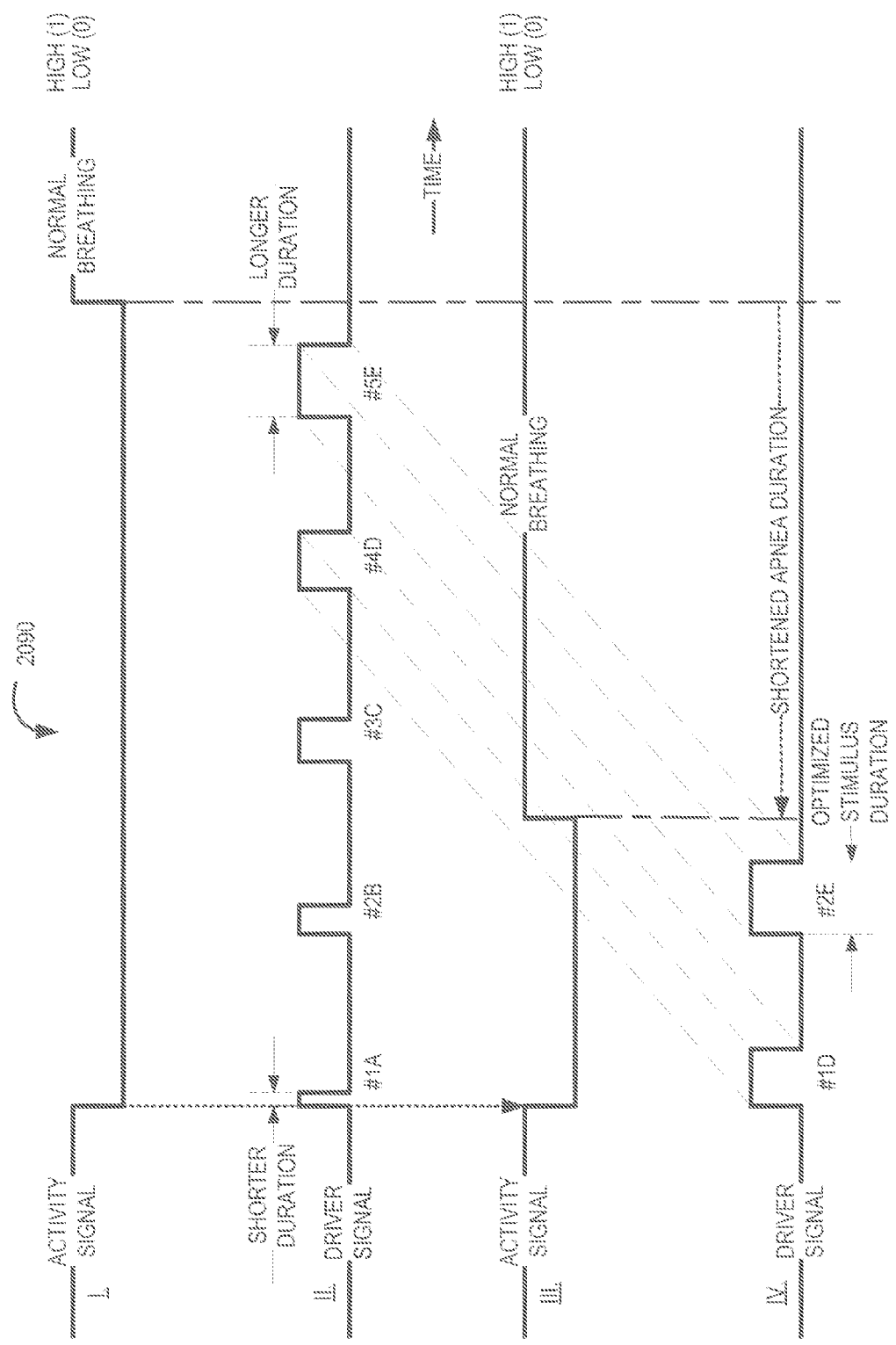
FIG. 16B illustrates generally a diagram depicting stimulus duration optimization.

Referring to FIG. 16B, there is indicated more specifically by numeral 2090 a diagram of a CNS stimulus duration optimization method.

There is indicated by Roman numeral I. an activity signal of a closed loop neuromodulator depicting non-optimized apnea duration at time interval T. The activity signal is represented by a logic level signal. The logic levels may take on either a logic high state ("1") or a logic low state ("0"). The high state indicates "normal breathing" which means that the patient is not currently experiencing a breathing disorder. The low state indicates "Apnea" which means that the patient is currently experiencing a breathing disorder.

There is indicated by Roman numeral II. a driver signal of a closed loop neuromodulator. The driver signal is represented by an analog level signal. The analog levels may take on any level value if instructed to do so between a lowest level and a highest level. In this case, the first stimulus being issued after a short delay in response to apnea detection is the shortest stimulus duration possible #1A. Stimulus #1A may be of any type, level or rate. If stimulus #1A does not cause the resumption of normal breathing, then after a certain amount of time that is dependent on the specific stimulus rate, second stimulus #2B is being issued. Since the first stimulus #1A did not produce the desired result, the duration (more duration equals more energy) for stimulus #2B has been increased by a specific amount which depends on the type of duration escalation envelope function. In this case, for sake of simplicity, the duration escalation envelope function has been chosen to be linear. This means the next stimulus duration increases with the same factor as the one before. Other duration stimulus escalation envelope functions are possible as discussed in the Stimulus Escalator section included herein. If stimulus #2B does not cause the resumption of normal breathing then after a certain amount of time that is dependent on the specific stimulus rate, a third stimulus #3C is being issued. Since the second stimulus #2B did not produce the desired result, the duration for stimulus #3C has been increased by a specific amount, which depends on the type of duration escalation envelope function.

If stimulus #3C does not caused the resumption of normal breathing then after a certain amount of time that is dependent on the specific stimulus rate, a fourth stimulus #4D is being issued. Since the third stimulus #3C did not produce the desired result, the duration for stimulus #4D has been increased by a specific amount, which depends on the type of duration escalation envelope function.

If stimulus #4D does not cause the resumption of normal breathing then after a certain amount of time that is dependent on the specific stimulus rate, a fifth stimulus #5E is being issued. Since the fourth stimulus #4D did not produce the desire result, the duration for stimulus #5E has been increased by a specific amount, which depends on the type of duration escalation envelope function.

It shall be noted that the fifth stimulus in this case #5E has caused the resumption of normal breathing in the sleeping patient. At this point, the method instructs the apparatus to store the value of the duration that caused the resumption of breathing in memory. This value shall be used as a marker so that the first stimulus duration the closed loop neuromodulator selects and issues after detection of the next apnea episode is at least one or more escalation durations below the duration that caused the resumption of breathing during the previous apnea episode experienced by the patient. In this special case duration level #E was the one that caused the resumption of normal breathing, thus the first stimulus duration that shall be issued when the next apnea episode occurs is stimulus level #D.

There is indicated by Roman numeral III. an activity signal of a closed loop neuromodulator depicting an optimized apnea duration at time interval T+1 indicating the next apnea episode following the apnea episode duration at the time interval T. The activity signal is represented by a logic level signal. The logic levels may take on either a logic high state ("1") or a logic low state ("0"). The high state indicates "normal breathing" which means that the patient is not currently experiencing a breathing disorder. The low state indicates "Apnea" which means that the patient is currently experiencing a breathing disorder.

There is indicated by Roman numeral VI. a driver signal of a closed loop neuromodulator. The driver signal is represented by an analog level signal. The analog durations may take on any duration value if instructed to do so between a lowest duration and a highest duration. In this case, the first stimulus being issued after a short delay in response to the next apnea detection is the third duration down from the duration during the previous apnea that caused the resumption of normal breathing in the sleeping patient stimulus duration #1D. Stimulus #1D is preferably of the same type, level and/or rate but may be of any type, level and/or rate. If stimulus #1D does not cause the resumption of normal breathing then after a certain amount of time that is dependent on the specific stimulus rate, second stimulus #2E is being issued. Since the first stimulus #1D did not produce the desired result, the duration for stimulus #2E has been increased by a specific amount, which depends on the type of duration escalation envelope function. In this case, for sake of simplicity, the duration escalation envelope function has been chosen to be linear. This means the next stimulus duration increases with the same factor as the one before. Other duration stimulus escalation envelope functions are possible as discussed in the Stimulus Escalator section included herein.

It shall be noted that the second stimulus this time #2E has caused the resumption of normal breathing in the sleeping patient. At this point, again, the method instructs the apparatus to store the value of the stimulus duration that caused the resumption of breathing in memory. This value shall be used as a marker so that the first stimulus duration the closed loop neuromodulator selects and issues after detection of the next apnea episode is at least one or more escalation durations below the duration that caused the resumption of breathing during the previous apnea episode experienced by the patient. In this special case stimulus duration #E was the one that caused the resumption of normal breathing, thus the first duration that shall be issued when the next apnea episode occurs is stimulus duration #D, because the escalation resumption point has been set to one level down in this case.

The method changing stimuli and patterns of issuing more energy containing stimulus types, levels, durations and rates continues until normal breathing has been detected.

Figure 16C:
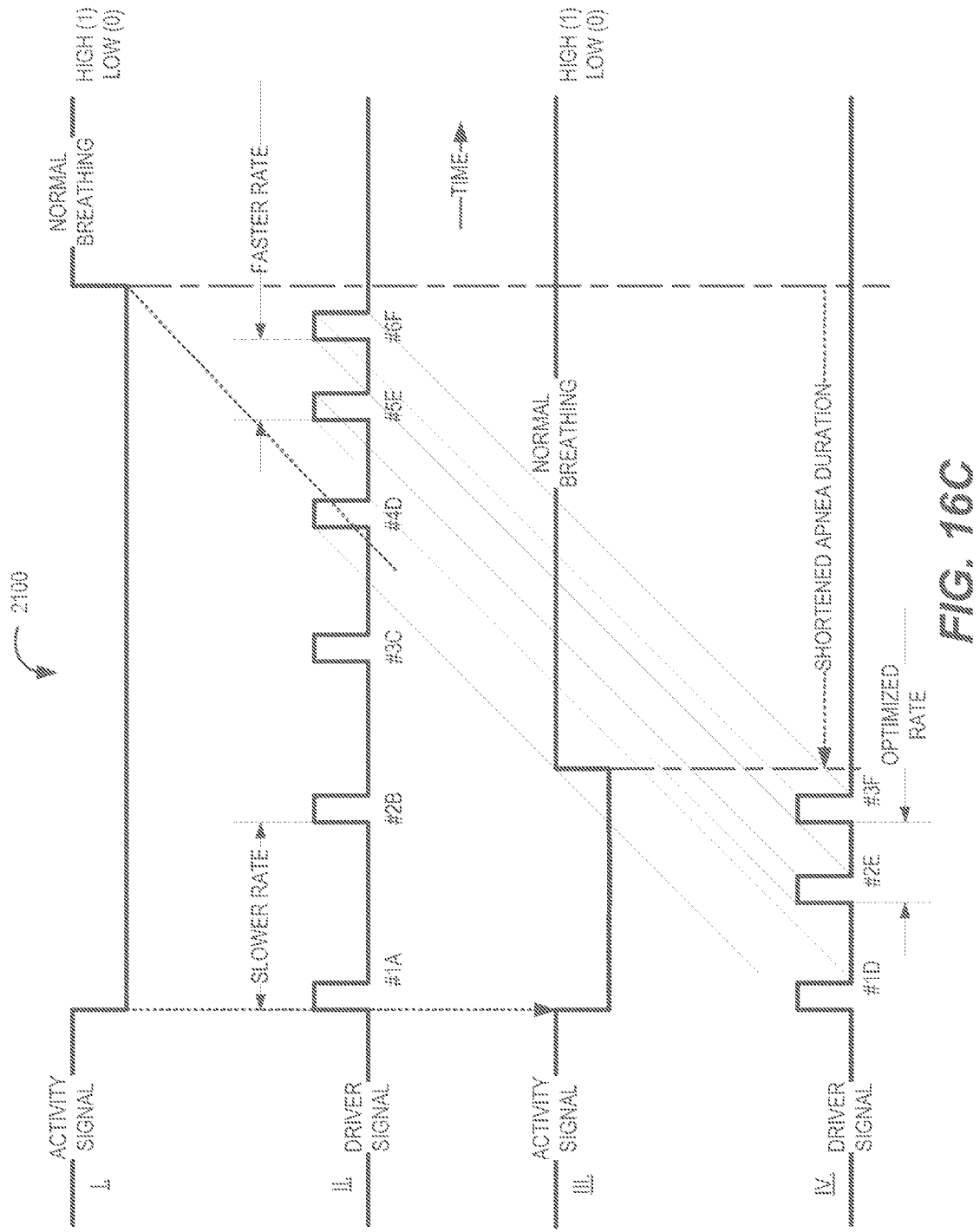
FIG. 16C illustrates generally a timing diagram depicting stimulus rate optimization.

Referring to FIG. 16C, there is indicated more specifically by numeral 2100 a diagram of a CNS stimulus rate optimization method.

There is indicated by Roman numeral I. an activity signal of a closed loop neuromodulator depicting non-optimized apnea duration at time interval T. The activity signal is represented by a logic level signal. The logic levels may take on either a logic high state ("1") or a logic low state ("0"). The high state indicates "normal breathing" which means that the patient is not currently experiencing a breathing disorder. The low state indicates "Apnea" which means that the patient is currently experiencing a breathing disorder.

There is indicated by Roman numeral II. A driver signal of a closed loop neuromodulator. The driver signal is represented by an analog level signal. The analog levels may take on any level value if instructed to do so between a lowest level and a highest level. In this case, the first stimulus being issued after a short delay in response to an apnea detection is the lowest stimulus rate possible (as defined in the default settings) #1A. Stimulus #1A may be of any type, duration or level. If stimulus #1A does not cause the resumption of normal breathing then after a certain amount of time that is dependent on the specific stimulus rate, second stimulus #2B is being issued. Since the first stimulus #1A did not produce the desired result, the rate for stimulus #2B has been increased (sped up) by a specific amount, which depends on the type of rate escalation envelope function. In this case, for sake of simplicity, the rate escalation envelope function has been chosen to be linear. This means the next stimulus level increases with the same factor as the one before. Other rate stimulus escalation envelope functions are possible as discussed in the Stimulus Escalator section included herein. If stimulus #2B does not cause the resumption of normal breathing then after a certain amount of time that is dependent on the specific stimulus rate, a third stimulus #3C is being issued. Since the second stimulus #2B did not produce the desire result, the rate for stimulus #3C has been increased by a specific amount, which depends on the type of rate escalation envelope function.

If stimulus #3C does not cause the resumption of normal breathing then after a certain amount of time that is dependent on the specific stimulus rate, a fourth stimulus #4D is being issued. Since the third stimulus, #3C did not produce the desire result, the rate for stimulus #4D has been increased by a specific amount which depends on the type of rate escalation envelope function.

If stimulus #4D does not cause the resumption of normal breathing then after a certain amount of time that is dependent on the specific stimulus rate, a fifth stimulus #5E is being issued. Since the fourth stimulus #4D did not produce the desire result, the rate for stimulus #5E has been increased by a specific amount which depends on the type of rate escalation envelope function.

If stimulus #5E does not cause the resumption of normal breathing then after a certain amount of time that is dependent on the specific stimulus rate, a sixth stimulus #6F is being issued. Since the fifth stimulus #5E did not produce the desire result, the rate for stimulus #6F has been increased by a specific amount which depends on the type of rate escalation envelope function.

It shall be noted that the seventh stimulus in this case #6F has caused the resumption of normal breathing in the sleeping patient. At this point, the method instructs the apparatus to store the value of the rate that caused the resumption of breathing in memory. This value shall be used as a marker so that the first stimulus rate the closed loop neuromodulator selects and issues after detection of the next apnea episode is at least one or more escalation rates below the rate that caused the resumption of breathing during the previous apnea episode experienced by the patient. In this special case stimulus rate #F was the one that caused the resumption of normal breathing, thus the first rate that shall be issued when the next apnea episode occurs is stimulus rate #D.

There is indicated by Roman numeral III. an activity signal of a closed loop neuromodulator depicting an optimized apnea duration at time interval T+1 indicating the next apnea episode following the apnea episode duration at the time interval T. The activity signal is represented by a logic level signal. The logic levels may take on either a logic high state ("1") or a logic low state ("0"). The high state indicates "normal breathing" which means that the patient is not currently experiencing a breathing disorder. The low state indicates "Apnea" which means that the patient is currently experiencing a breathing disorder.

There is indicated by Roman numeral VI. a driver signal of a closed loop neuromodulator. The driver signal is represented by an analog level signal. The analog levels may take on any level value if instructed to do so between a lowest level and a highest level. In this case, the first stimulus being issued after a short delay in response to the next apnea detection is the third rate down from the rate during the previous apnea that caused the resumption of normal breathing in the sleeping patient stimulus rate #1D. Stimulus #1D is preferably of the same type, duration and/or level but may be of any type, duration or level. If stimulus #1D does not cause the resumption of normal breathing then after a certain amount of time that is dependent on the specific stimulus rate, second stimulus #2E is being issued. Since the first stimulus #1D did not produce the desired result, the rate for stimulus #2E has been increased by a specific amount, which depends on the type of rate escalation envelope function. In this case, for sake of simplicity, the rate escalation envelope function has been chosen to be linear. This means the next stimulus rate increases with the same factor as the one before. Other rate stimulus escalation envelope functions are possible as discussed in the Stimulus Escalator section included herein. If stimulus #2E does not cause the resumption of normal breathing then after a certain amount of time that is dependent on the specific stimulus rate, a third stimulus #3F is being issued. Since the second stimulus #2E did not produce the desire result, the rate for stimulus #3F has been increased by a specific amount, which depends on the type of rate escalation envelope function.

It shall be noted that the third stimulus this time #3F has caused the resumption of normal breathing in the sleeping patient. At this point, again, the method instructs the apparatus to store the value of the rate that caused the resumption of breathing in memory. This value shall be used as a marker so that the first stimulus rate the closed loop neuromodulator selects and issues after detection of the next apnea episode is at least one or more escalation rates below the rate that caused the resumption of breathing during the previous apnea episode experienced by the patient. In this special case stimulus rate #F was the one that caused the resumption of normal breathing, thus the first rate that shall be issued when the next apnea episode occurs is stimulus rate #D.

The method changing stimuli and patterns of issuing more energy containing stimulus types, levels, durations and rates continues until normal breathing has been detected.

Figure 17:
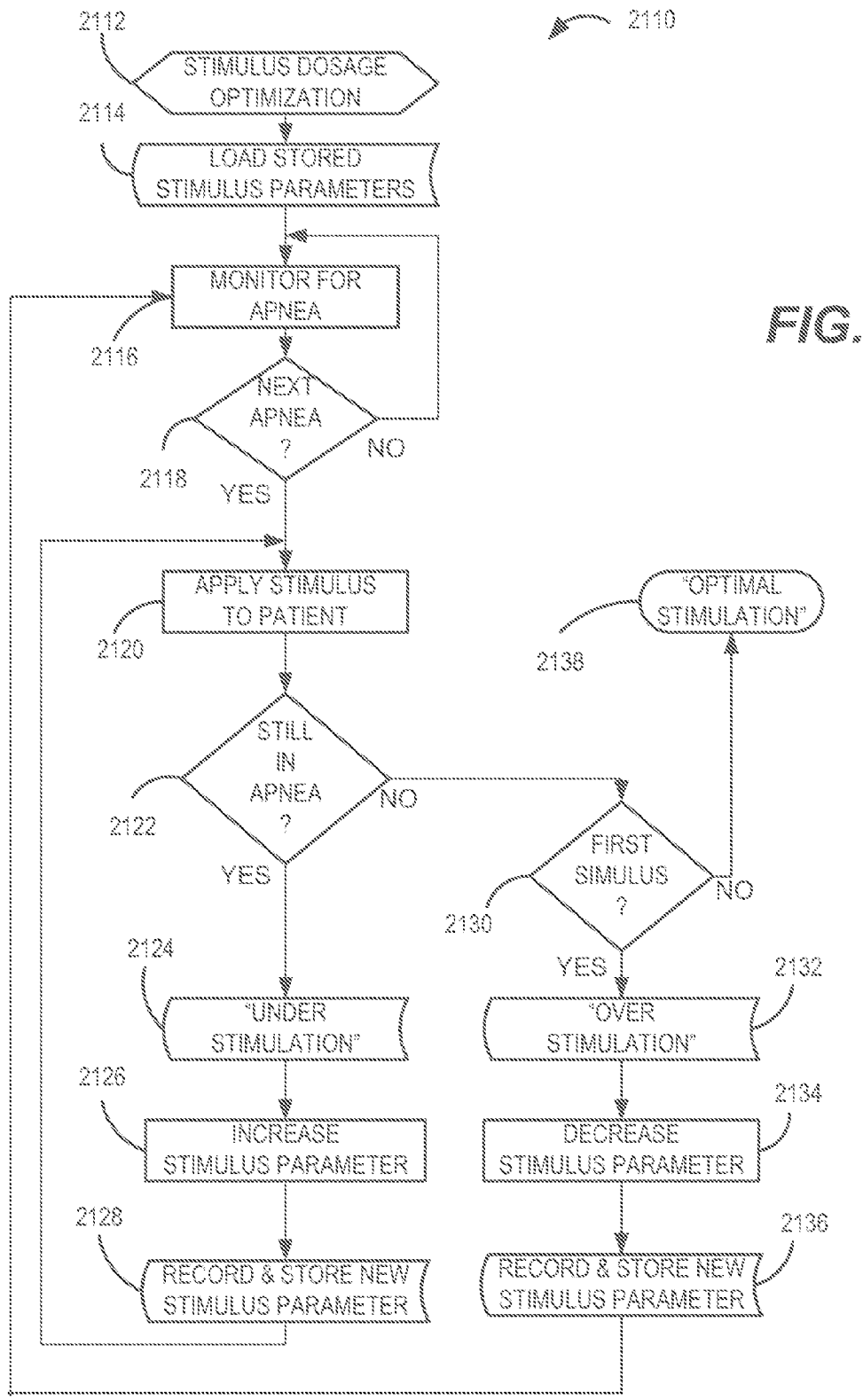
FIG. 17 is a detailed flow-chart for the Stimulus Dosage Optimization of the closed loop neuromodulator according to one example of the present subject matter.

Referring to FIG. 17, there is indicated more specifically by numeral 2110 a flowchart of stimulus dosage optimization routine for a closed loop neuromodulator. The stimulus dosage optimization routine begins with the Stimulus Dosage Optimization start command 2112. The next step after the start command 2112 is the instruction to load the stored stimulus parameters 2114, which at first may be the default values as defined by the outcome of clinical trials or as defined by a sleep practitioner. The next process after loading the stored stimulus parameters is to monitor for Apnea 2116. The next step after monitoring for an apnea is the decision point which asks for the Next Apnea? 2118. If the answer to the decision point question is NO then the routine will continue to monitor for Apnea. If the answer to the decision point question is YES then the next process in the routine is to Apply Stimulus to Patient 2120. During and after the stimulus has been applied to the patient another decision point asks if the patient is still in Apnea? 2122. If the answer to the decision point question is NO then the routine encounters another decision point, which asks if this was the first Stimulus? 2130 in this apnea episode. If the answer to this decision point question is YES, then the routine indicates "Over Stimulation" 2132, which may be subsequently logged, and time stamped for further use and reference. The next step after "Over Stimulation" 2132 which also means that the first stimulus issued to the patient caused the resumption of breathing is to decrease the stimulus parameter 2134 followed by a Record & Store New Stimulus Parameter 2136 instruction. Since the patient is not experiencing an Apnea at this state, the next step is to monitor for Apnea 2116. If the patient experiences another apnea then the answer to the Next Apnea 2118 decision point question is YES then the next process in the routine is to Apply Stimulus to Patient 2120. During and after the stimulus has been applied to the patient another decision point asks if the patient is still in Apnea? 2122. If the answer to the decision point question is YES then the routine indicates "Under Stimulation" 2124, which may be subsequently logged, and time stamped for further use and reference. The next step after "Under Stimulation" 2124 which also means that the stimulus issued to the patient did not cause the resumption of breathing is to increase the stimulus parameter 2126 followed by a Record & Store New Stimulus Parameter 2128 instruction. Since the patient is experiencing an Apnea at this state, the next step is to Apply Stimulus to the Patient 2120. During and after the stimulus has been applied to the patient a decision point asks if the patient is still in Apnea <?> 2122. If the answer to the decision point question is NO then the routine encounters another decision point which asks if this was the first Stimulus <?> 2130 in this apnea episode. If the answer to this decision point question is NO, then the routine indicates "Optimal Stimulation" 2138, which may be subsequently logged, and time stamped for further use and reference. The stimulus dosage optimization routine may at this point be terminated, re-routed to another routine or start all over again.

Diagnostic and Therapy Modes

There is a need for automatic/autonomous mode, so that the sleep patient can operate the unit at home without any manual interaction or intervention. In diagnostic mode the sleep lab practitioner can find the optimum range of stimulus escalation for the individual patient. In various examples, diagnostic mode is used in a sleep lab to setup a closed loop neuromodulator and then the patient is sent home where the closed loop neuromodulator is used in therapy mode to provide sleep therapy. In some examples, a sleep lab only uses diagnostic mode of the neuromodulator.

In therapy mode, the unit executes its operation based on the ranges defined and set by the sleep practitioner.

In therapy mode, the unit is the controller part of a respiratory biofeedback loop.

Delay, rate, duration, period, frequency, range etc. are all variable and manually adjustable by sleep lab practitioner when this invention is used in diagnostic mode or automatically adjustable when used in therapy mode.

Especially ranges or all adjustable parameters are settable by the sleep practitioner in diagnostic mode.

Therapy mode is automatic and is an autonomous operation.

All timing is variable, adjustable, controllable, either manual or automatic.

In therapy mode, the unit can operate under minimum power requirements and highest efficiency, thus, saving battery life and extending time of operation. The use of a digital output drive amplifier like a class D-audio amplifiers that are available from semiconductor manufacturers will allow for efficient use of battery power during the application of therapy stimuli.

A set of subroutines in the diagnostic remote terminal can make calculations based on the registers and values provided by the device. A few examples of such calculations that will give the medical practitioner a better patient picture are listed below:

1. Average Breaths per Minute (or any other time reference)
2. Average Inhale duration over Exhale duration ratio
3. Average Apneas per hour (or any other time reference)
4. Average Stimuli per hour
5. Average Stimuli per Apnea
6. Histograms of inhalation count and durations
7. Histograms of exhalation counts and durations
8. Histograms of inhalations over exhalations ratios
9. Histogram of total Apnea episodes
10. Histogram of total stimuli applied
11. Histogram of Apneas per hour
12. Histogram of Stimuli per hour
13. Histogram of Stimuli per Apnea
14. Standard Deviations for all calculated statistics
15. Detailed time stamped event logs for each apnea episode Closed Loop Neuromodulator Each of the closed loop neuromodulator's 4 internal building block output signals are made available via individual signal output ports for connection to a PSG for further analysis: These building blocks include the digital signal 12 generated by the EMI/ESD hardened sensor Interface 10, activity signal 22 generated by the Activity Detector 20, power-down signal 24 generated by the Activity Detector 20, reset signal 26 generated by the Activity Detector, start signal 32 generated by the stimulus timer, trigger signal 34 generated by the stimulus timer, driver signal 42 generated by the stimulus escalator, transducer output 5 generated by the EMI/ESD hardened transducer driver, stimuli select signal 62 generated by the stimulus sequencer, stimuli signal 66 generated by the stimulus sequencer, and stimuli output signal 72 generated by the stimulus generator.

FIG. 3 is an electrical block diagram of one specific embodiment of the closed loop neuromodulator 4 depicted in FIG. 2 and FIG. 1. There is indicated generally by numeral 4 a block diagram of the closed loop neuromodulator along with a sensor 2 and a transducer 6. Attached to the sensor and closed loop neuromodulator is a pair of wire terminations 3 via which the closed loop neuromodulator receives the sensor output. Attached to the transducer and closed loop neuromodulator is a pair of wire terminations 5 via which the closed loop neuromodulator transmits the transducer input. Furthermore the closed loop neuromodulator indicated generally by numeral 4 contains a mixed signal micro controller (such as a Freescale FireWire processor) or an FPGA based processor (such as a National Instrument, LabVIEW based RIO virtual device development system) with internal processor, read-only memory (ROM), random access memory (RAM), reset manager, power pump, oscillator, analog-to-digital converter (ADC), digital-to-analog converter (DAC) and embedded code.

The present invention is advantageous because it is directed toward precise dosing of specific stimuli, which makes the device universally effective for most sleep patients. This is in contrast to the continuous positive air pressure (CPAP), Bi-level positive air pressure (BPAP), and any other CNS Stimulation controller that arouses or wakes the patient of the prior art.

An additional advantage of the present invention is the precision with which stimulating doses can be given to a person suffering from various kinds of neurological or sleeps disorders.

Another advantage of the present invention relates to the various types of stimuli it can apply in order to avoid patient habituation.

An additional advantage is the device's ability to be used in a clinical, research or laboratory setting in order to diagnose patients and figure out which type of stimuli works optimally for a specific patient, a group of patients or any other setting.

An additional advantage is that upon detection of a no breathing signal, the device sends single stimuli of a certain level, frequency, modulation, and shape for certain duration to the patient. If breathing does not resume after a preset amount of time, then another yet stronger stimuli signal will be issued to the patient.

Another advantage is that the sequence of issuing stimuli and sending them to the patient continues until the resumption of breathing has been detected.

Another advantage is that during low power operation functional blocks may be shut down when not needed for immediate operation. E.g. shut down generators, timers and gain block when breathing is detected. Activate generators, timers and gain block when no breathing is detected.

This further supports the device's ability to interrupt an undesirable behavior while avoiding alteration of a sleep state.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

The description of the various embodiments is merely exemplary in nature and, thus, variations that do not depart from the gist of the examples and detailed description herein are intended to be within the scope of the present disclosure. Such variations are not to be regarded as a departure from the spirit and scope of the present disclosure.

Figure 18A:
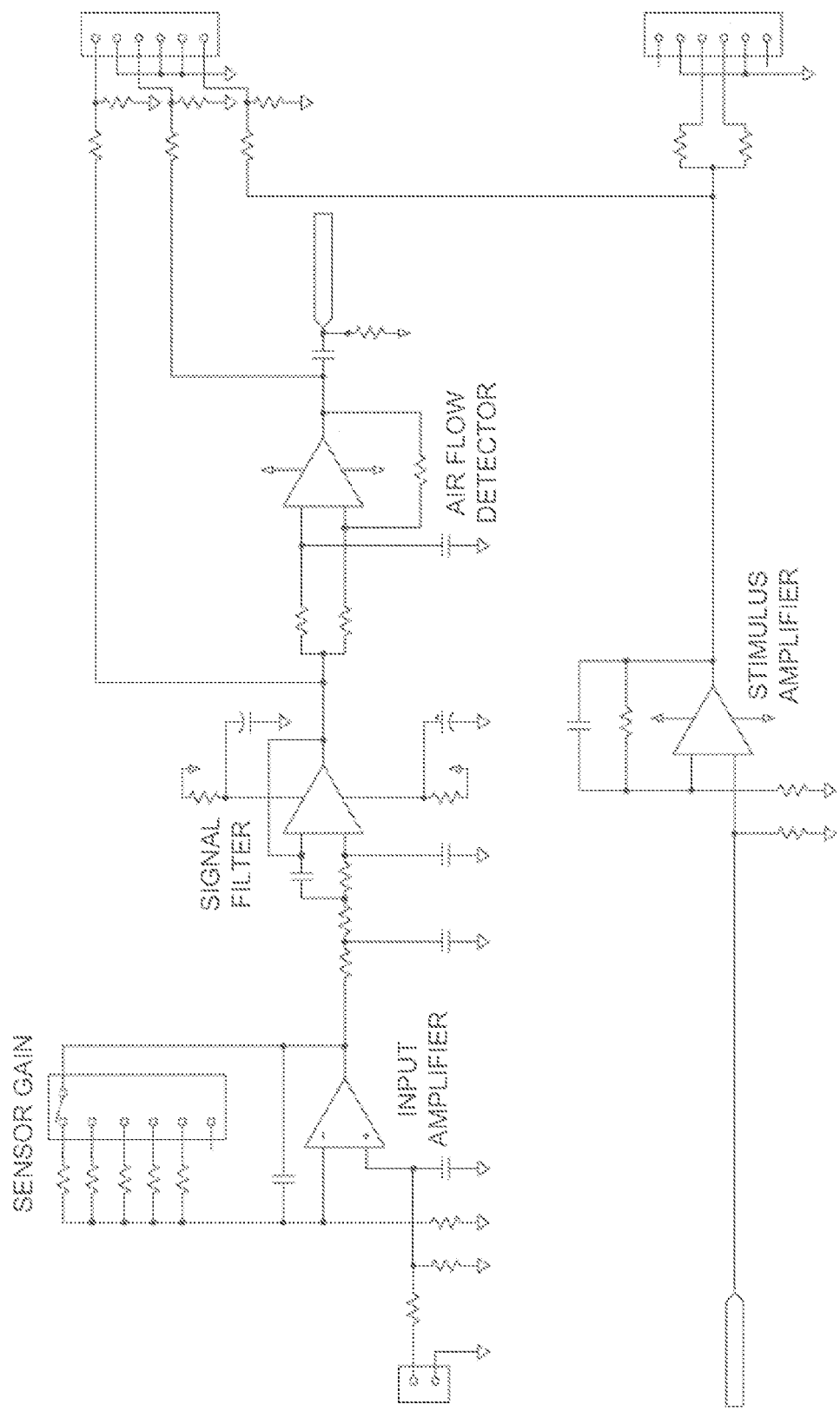
FIG. 18A is a detailed electrical schematic diagram of the analog section of a simplified discrete component embodiment of a closed loop neuromodulator according to one example of the present subject matter.
Figure 18B:
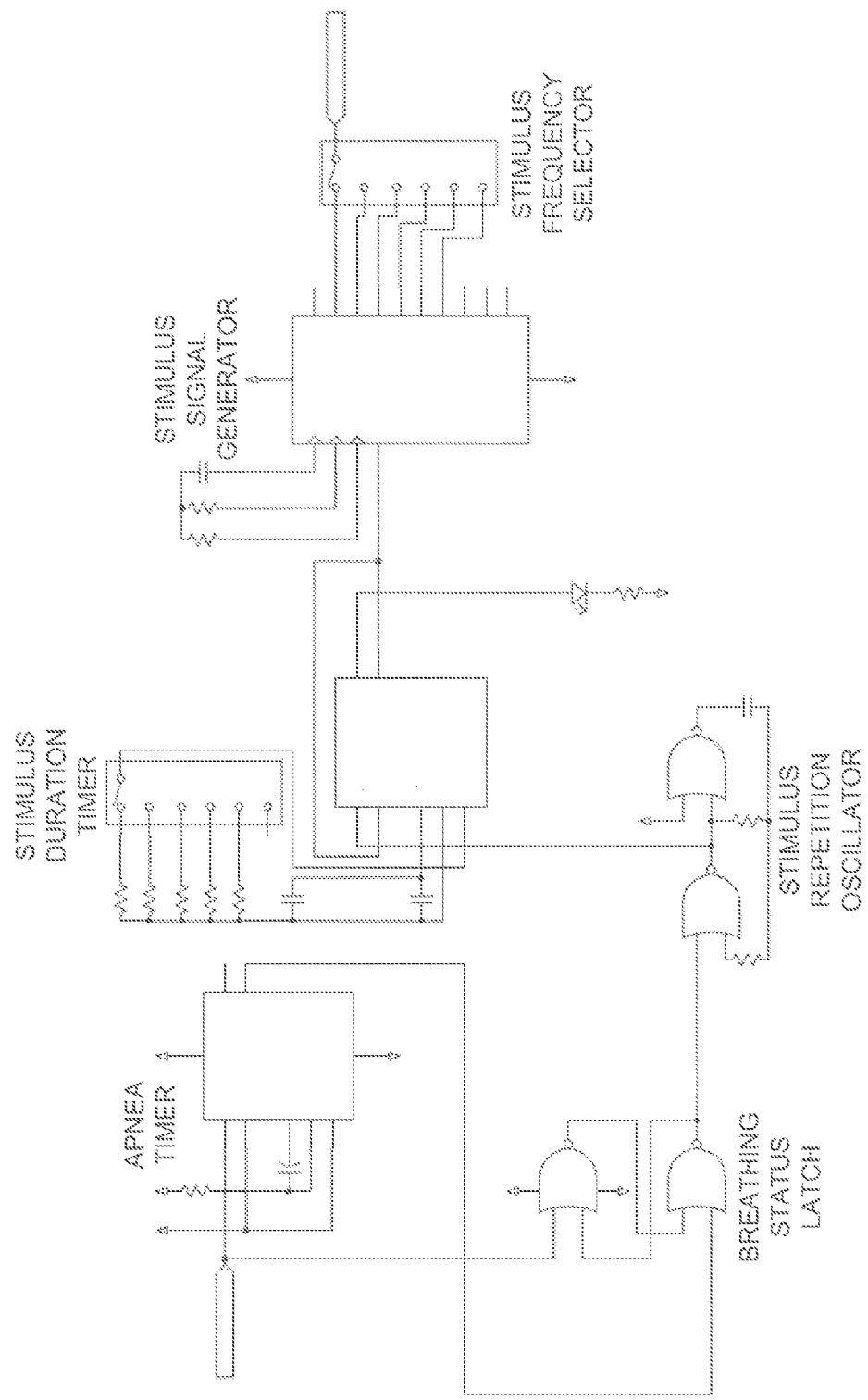
FIG. 18B is a detailed electrical schematic diagram of the digital section of a simplified discrete component embodiment of a closed loop neuromodulator according to one example of the present subject matter.
Figure 18C:
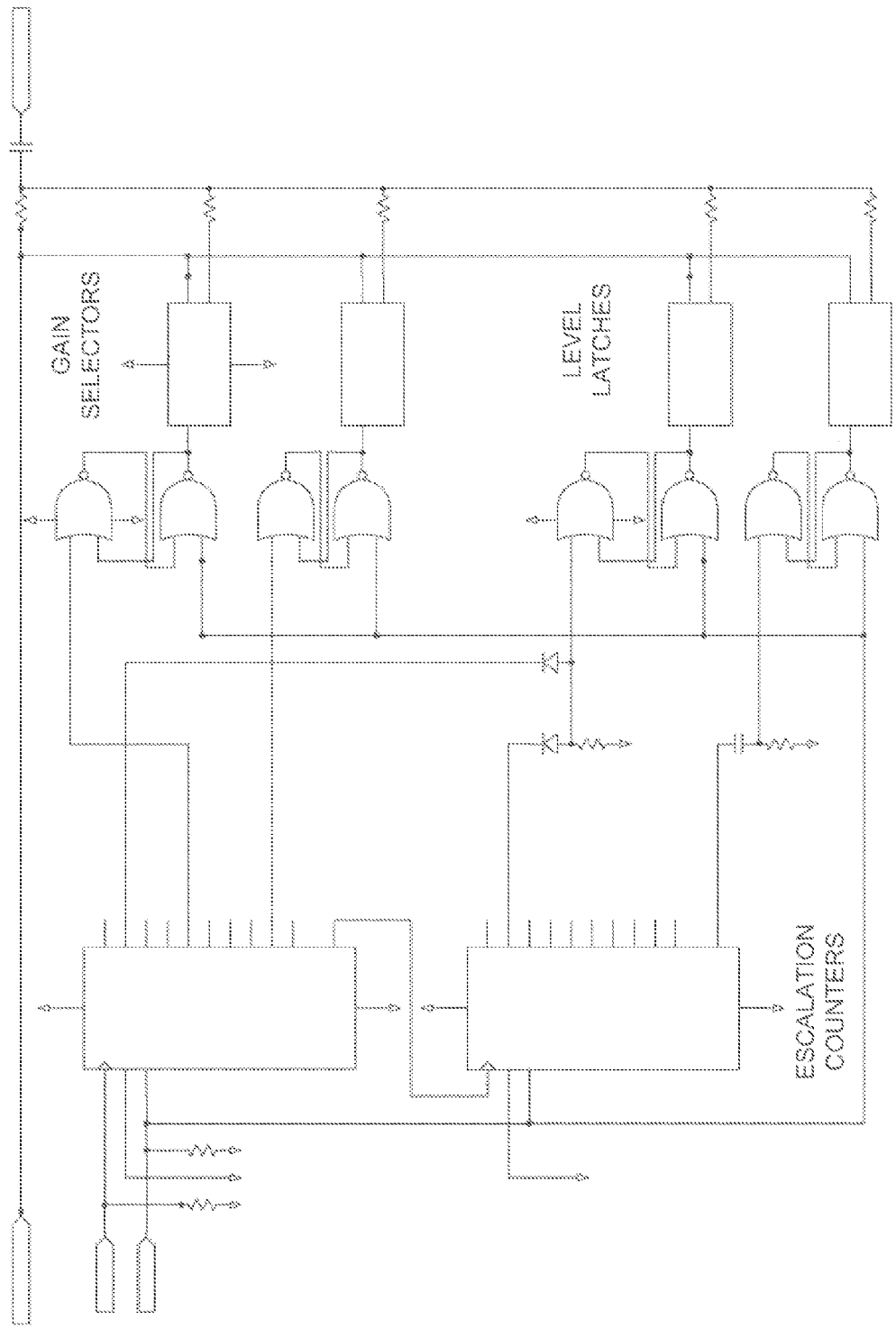
FIG. 18C is a detailed electrical schematic diagram of the level escalation section of a simplified discrete embodiment of a closed loop neuromodulator according to one example of the present subject matter.
Figure 18D:
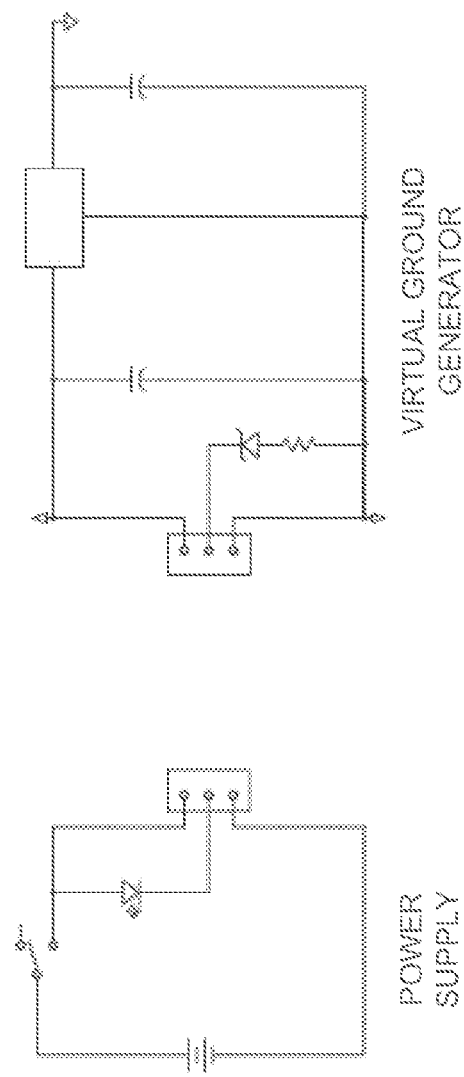
FIG. 18D is a detailed electrical schematic diagram of the power supply section of a simplified discrete component embodiment of a closed loop neuromodulator according to one example of the present subject matter.

FIGS. 18A through 18C depict an embodiment of a sleep therapy device, which formed the basis of a feasibility study and is a device that was used during clinical tests.

Below is a Bill-of-Materials of components for the components depicted in FIGS. 18A through 18C.

| Reference Designator | Value |
| --- | --- |
| B1 | 9 V |
| C1 | 10 uF/Tant |
| C10 | 0.01 uF |
| C11 | 0.039 uF |
| C12 | 10 uF/Tant |
| C13 | 0.39 uF |
| C14 | 1 uF |
| C15 | 0.1 uF |
| C16 | 100 pF |
| C17 | 1 uF |
| C19 | 0.039 uF |
| C2 | 10 uF/Tant |
| C20 | 0.1 uF |
| C21 | 1 uF |
| C3 | 10 uF/Tant |
| C4 | 0.1 uF |
| C5 | 0.1 uF |
| C7 | 0.39 uF |
| C8 | 0.056 uF |
| C9 | 10 uF/Tant |
| D1 | Green |
| D2 | 5.6 V |
| D3 | RED |
| D4 | 1N4148 |
| D5 | 1N4148 |
| J1 | Header, 3-pin, F |
| J2 | Header, 3-pin, M |
| J3 | Header, 2-pin, M |
| J4 | Header, 6-pin, M |
| J5 | Header, 6-pin, M |
| R1 | 1M |
| R10 | 560k |
| R11 | 560k |
| R12 | 560k |
| R13 | 1k |
| R14 | 1.5k |
| R15 | 1k |
| R16 | 100 |
| R17 | 10M |
| R18 | 5.6M |
| R19 | 2.7M |
| R2 | 100 |
| R20 | 100k |
| R21 | 1.35M |
| R22 | 560k |
| R23 | 1k |
| R24 | 270k |
| R25 | 1M |
| R28 | 1M |
| R29 | 10k |
| R3 | 560k |
| R30 | 1M |
| R31 | 220k |
| R32 | 20k |
| R33 | 1M |
| R34 | 1k |
| R35 | 1M |
| R36 | 2.2M |
| R4 | 220k |
| R40 | 10k |
| R41 | 2.2k |
| R43 | 10k |
| R45 | 22k |

-continued

| Reference Designator | Value |
| --- | --- |
| R47 | 22k |
| R48 | 10 |
| R49 | 10k |
| R5 | 56k |
| R50 | 100k |
| R51 | 100k |
| R52 | 10k |
| R53 | 100k |
| R54 | 330k |
| R55 | 220k |
| R56 | 150k |
| R57 | 82k |
| R58 | 47k |
| R6 | 5.6k |
| R7 | 27k |
| R8 | 100k |
| S1 | ON/OFF |
| S2 | 6 pos Rotary Switch |
| S3 | 6 pos Rotary Switch |
| S4 | 6 pos Rotary Switch |
| U1 | TLE2426 |
| U10: A | CD4001 |
| U10: B | CD4001 |
| U10: C | CD4001 |
| U10: D | CD4001 |
| U11: A | CD4001 |
| U11: B | CD4001 |
| U11: C | CD4001 |
| U11: D | CD4001 |
| U12: A | CD4066 |
| U12: B | CD4066 |
| U12: C | CD4066 |
| U12: D | CD4066 |
| U2: A | LMC6482 |
| U2: B | LMC6482 |
| U3: A | CD4098 |
| U3: B | CD4098 |
| U4: A | LMC6482 |
| U4: B | LMC6482 |
| U5: A | CD4001 |
| U5: B | CD4001 |
| U5: C | CD4001 |
| U5: D | CD4001 |
| U6 | CD4060 |
| U7: A | LMC6482 |
| U7: B | LMC6482 |
| U8 | CD4017 |
| U9 | CD4017 |

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventor also contemplates examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A stimulus sequencer for generating a sleep therapy stimulus waveform for a patient, the stimulus sequencer comprising:
   a sequence address generator configured to receive a stimulus start signal from a timer of a closed loop neuromodulator and to provide an address related to a stimulus sequence of the sleep therapy;
   a sequence memory array coupled to the sequence address generator, the sequence memory array configured to receive the address from the sequence address generator and to provide stimulus sequence information related to the address;
   a stimulus generator selector coupled to the sequence memory array, the stimulus generator selector configured to receive the stimulus sequence information from the sequence memory array, to receive a stimulus duration signal from the timer of the closed loop neuromodulator, and to provide a generator select, signal to a stimulus generator of the closed loop neuromodulator using the stimulus sequence information and the stimulus duration signal, the generator select signal including stimulus type information related to stimulus pulses generated using the closed loop neuromodulator; and
   wherein the sleep therapy stimulus waveform includes a sequence of one or more stimulus types.

2. The stimulus sequencer of claim 1, wherein the closed loop neuromodulator is configured to provide, in response to the stimulus start signal, a first, stimulus to the patient using information from the stimulus sequencer, the first stimulus configured to not interrupt a detected sleep disorder event; and wherein the closed loop neuromodulator is configured to provide, following the first stimulus, a second stimulus to the patient using information from the stimulus sequencer, the second stimulus having more energy than the first stimulus and configured to interrupt the detected sleep disorder event.

3. The stimulus sequencer of claim 1, including a sequence address generator register configured to provide programmable count parameter information to the sequence address generator using information from a control bus of the closed loop neuromodulator.

4. The stimulus sequencer of claim 1, including a sequence load control register configured to provide a sequence load control command to the sequence memory array using information from a control bus of the closed loop neuromodulator.

5. The stimulus sequencer of claim 1, including a sequence load address register configured to provide a sequence address load command to the sequence memory array using information from a control bus of the closed loop neuromodulator.

6. The stimulus sequencer of claim 1, including a sequence load data register configured to provide a sequence data load command to the sequence memory array using information from a control bus of the closed loop neuromodulator.

7. The stimulus sequencer of claim 1, wherein the sequence memory array is configured to select the stimulus sequence from a group comprising at least one of a fixed sequence, a sequential sequence, a circular sequence, a random sequence, a periodic sequence, a custom sequence, a patterned sequence, or a continuous sequence.

8. A system for generating a sleep therapy stimulus waveform for a patient, the system comprising:
a sensor configured to detect information indicative of respiration from a patient;
a closed loop neuromodulator configured to optimize sleep therapy for the patient, the closed loop neuromodulator including:
a stimulus sequencer configured to provide a generator select signal to a stimulus generator of the closed loop neuromodulator, the stimulus sequencer including:
a sequence address generator configured to receive a stimulus start signal from a timer of a closed loop neuromodulator and to provide an address related to a stimulus sequence of the sleep therapy;
a sequence memory array coupled to the sequence address generator, the sequence memory array configured to receive the address from the sequence address generator and to provide stimulus sequence information related to the address;
a stimulus generator selector coupled to the sequence memory array, the stimulus generator selector configured to receive the stimulus sequence information from the sequence memory array, to receive a stimulus duration signal from the timer of the closed loop neuromodulator, and to provide a generator select signal to the stimulus generator of the closed loop neuromodulator using the stimulus sequence information and the stimulus duration signal, the generator select signal including stimulus type information related to stimulus pulses generated using the closed loop neuromodulator;
wherein the sleep therapy stimulus waveform includes a sequence of one or more stimulus types; and
a sequence address generator register configured to provide programmable count parameter information to the sequence address generator using information from a control bus of the closed loop neuromodulator;
a sequence load control register configured to provide a sequence load control command to the sequence memory array using information from the control bus of the closed loop neuromodulator,
a sequence load address register configured to provide a sequence address load command to the sequence memory array using information from the control bus of the closed loop neuromodulator; and
a sequence load data register configured to provide a sequence data load command to the sequence memory array using information from the control bus of the closed loop neuromodulator;
wherein the sequence memory array is configured to select a stimulus sequence from a group comprising at least one of a fixed sequence, a sequential sequence, a circular sequence, a random sequence, a periodic sequence, a custom sequence, a patterned sequence, or a continuous sequence;
wherein the closed loop neuromodulator is configured to provide, in response to the stimulus start signal, a first stimulus to a transducer using information from the stimulus sequencer, the first stimulus configured to not interrupt a detected sleep disorder event;
wherein the closed loop neuromodulator is configured to provide, following the first stimulus, a second stimulus to the transducer using information from the stimulus sequencer, the second stimulus having more energy than the first stimulus and configured to interrupt the detected sleep disorder event; and
wherein the transducer is configured to deliver the first and second stimuli to the patient.

9. The system of claim 8, wherein the sensor includes at least one of a thermocouple, a thermistor, an air pressure transducer, an electrode, a respiratory effort belt, or a pyro/piezoelectric sensor; and
wherein the transducer includes at least one of an acoustic transducer, a tactile mechanical agitator, an ocular stimulator, an electrical stimulator, a thermal stimulator, or an ultrasonic stimulator configured to modulate an audible signal onto an ultrasonic sound carrier.

10. A method for generating a sleep therapy stimulus waveform for a patient, the method comprising:
receiving a stimulus start signal from a timer of a closed loop neuromodulator
and providing an address related to a stimulus sequence of the sleep therapy to a sequence memory array using a sequence address generator;
providing stimulus sequence information related to the address to a stimulus generator selector using the sequence memory array;
receiving the stimulus sequence information from the sequence memory array and a stimulus duration signal from the timer of the closed loop neuromodulator at the stimulus generator selector;
providing, using the stimulus generator selector, a generator select signal to a stimulus generator of the closed loop neuromodulator using the stimulus sequence information and the stimulus duration signal, the generator select signal including stimulus type information related to stimulus pulses generated using the closed loop neuromodulator, and
wherein the sleep therapy stimulus waveform includes a sequence of one or more stimulus types.

11. The method of claim 10, including:
provjding, in response to the stimulus start signal, a first stimulus to the patient using the generator select signal, the first stimulus configured to not interrupt a detected sleep disorder event; and
providing, following the first stimulus, a second stimulus to the patient using the generator select signal, the second stimulus having more energy than the first stimulus and configured to interrupt the detected sleep disorder event.

12. The method of claim 10, including providing, using a sequence address generator register, programmable count parameter information to the sequence address generator using information from a control bus of the closed loop neuromodulator.

13. The method of claim 10, including providing, using a sequence load control register, a sequence load control command to the sequence memory array using information from a control bus of the closed loop neuromodulator.

14. The method of claim 10, including providing, using a sequence load address register, a sequence address load command to the sequence memory array using information from a control bus of the closed loop neuromodulator.

15. The method of claim 10, including providing, using a sequence load data register, a sequence data load command to the sequence memory array using information from a control bus of the closed loop neuromodulator.

16. The method of claim 10, wherein the providing stimulus sequence information related to the address includes selecting the stimulus sequence from a group comprising at least one of a fixed sequence, a sequential sequence, a circular sequence, a random sequence, a periodic sequence, a custom sequence, a patterned sequence, or a continuous sequence.

* * * * *